(12) United States Patent
Boiteau et al.

(10) Patent No.: US 8,383,652 B2
(45) Date of Patent: *Feb. 26, 2013

(54) BIAROMATIC COMPOUNDS THAT MODULATE PPAR-RECEPTORS

(75) Inventors: Jean-Guy Boiteau, Saint-Aunes (FR); Laurence Clary, La Colle sur Loop (FR); Laurent Chantalat, Grasse (FR); Michel Rivier, Nice (FR)

(73) Assignee: Galderma Research & Development, Biot (FR)

( * ) Notice: Subject to any disclaimer, the term of this patent is extended or adjusted under 35 U.S.C. 154(b) by 1271 days.

This patent is subject to a terminal disclaimer.

(21) Appl. No.: 12/110,815

(22) Filed: Apr. 28, 2008

(65) Prior Publication Data

US 2009/0012129 A1 Jan. 8, 2009

Related U.S. Application Data

(63) Continuation of application No. PCT/IB2006/003956, filed on Oct. 19, 2006.

(60) Provisional application No. 60/734,758, filed on Nov. 9, 2005.

(30) Foreign Application Priority Data

Oct. 26, 2005 (FR) .................... 05 10948

(51) Int. Cl.
  *A01N 43/40* (2006.01)
  *A01N 47/28* (2006.01)
  *A61K 31/44* (2006.01)
  *A61K 31/17* (2006.01)
  *C07D 213/22* (2006.01)
  *C07C 335/00* (2006.01)

(52) U.S. Cl. ........ 514/334; 514/596; 514/585; 546/257; 564/26

(58) Field of Classification Search .................. 514/334, 514/596, 585; 546/257; 564/26
See application file for complete search history.

(56) References Cited

U.S. PATENT DOCUMENTS

| 5,162,345 | A | * | 11/1992 | Semeraro et al. | 514/356 |
| 6,927,228 | B2 | | 8/2005 | Bernardon et al. | |
| 7,294,639 | B2 | | 11/2007 | Bernardon et al. | |
| 7,863,332 | B2 | * | 1/2011 | Clary et al. | 514/598 |
| 2007/0207175 | A1 | | 9/2007 | Clary et al. | |
| 2008/0027077 | A1 | * | 1/2008 | Boiteau et al. | 514/256 |

FOREIGN PATENT DOCUMENTS

| EP | 1067109 A1 | 1/2001 |
| WO | WO 02/12210 A1 | 2/2002 |
| WO | WO 03/055867 A1 | 7/2003 |
| WO | WO 2006/018326 A1 | 2/2006 |
| WO | WO 2006/053791 A2 | 5/2006 |

OTHER PUBLICATIONS

Morissette et al. "High-throughput crystallization: polymorphs, salts, co-crystals and solvates of pharmaceutical solids" Advanced Drug Delivery Reviews, 2004, vol. 56, pp. 275-300.*
International Search Report corresponding to PCT/IB/2006/003956.

* cited by examiner

*Primary Examiner* — Sreeni Padmanabhan
*Assistant Examiner* — Kendra D Carter
(74) *Attorney, Agent, or Firm* — SNR Denton US LLP

(57) ABSTRACT

Novel biaromatic compounds that modulate peroxisome proliferator-activator receptors, known as PPAR, having the formula (I):

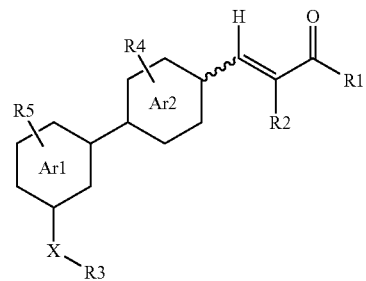

are formulated into pharmaceutical compositions useful in human or veterinary medicine, or alternatively, in cosmetic compositions.

34 Claims, 5 Drawing Sheets

BIAROMATIC COMPOUNDS THAT MODULATE PPAR-RECEPTORS

CROSS-REFERENCE TO EARLIER APPLICATIONS

This application is a continuation of PCT/IB 2006/003956, filed Oct. 19, 2006, and designating the United States, published in the English language as WO 2007/049158 A2 on May 3, 2007, which claims benefit of U.S. Provisional Application No. 60/734,758, filed Nov. 9, 2005 and also claims foreign priority under 35 U.S.C. §119 of FR 0510948, filed Oct. 26, 2005, each hereby expressly incorporated by reference in its entirety and each assigned to the assignee hereof.

BACKGROUND OF THE INVENTION

1. Technical Field of the Invention:

The present invention relates to novel biaromatic compounds, which are modulators of peroxisome proliferator-activated receptors, known as PPAR. This invention also relates to processes for the preparation thereof and to their formulation into pharmaceutical compositions for administration in human or veterinary medicine, or alternatively for inclusion in cosmetic compositions.

2. Description of Background and/or Related and/or Prior Art:

Peroxisome proliferator-activated receptors (PPAR) belong to the superfamily of hormonal nuclear receptors (Mangelsdorf, D. J. et al. *Cell*, 1995, 83, 841-850). After activation by a ligand, these proteins act as transcription factors and regulate many physiological phenomena, such as reproduction, growth, differentiation, development, metabolic energy and homeostasis. The PPAR subfamily (Kliewer, S. A. et al. *Nature*, 1992, 358, 771-774; Hertz, R. et al. *J. Eur. J. Biochem.*, 1996, 235, 242-247; Devchand, P. R. et al. *Nature* 1996, 384, 39-43; Spiegelman, B. M. *Cell* 1998, 93, 153-155; Kliewer, S. A. et al. *Science* 1999, 284, 757-760; Willson, T. M. et al., 2000, 43, 527-550) comprises three isoforms (α, γ and δ), which have different tissue distributions and exert different physiological functions, and serve as food lipid sensors for controlling carbohydrate and fatty acid metabolism (Willson, T. M. et al. *J. Med. Chem.*, 2000, 43, 527-550). The PPARα receptors are mainly expressed in the liver, and, after binding with one of their ligands, for example a fibrate, stimulate lipid metabolization.

The PPARγ receptors are strongly expressed in adipocyte tissue, and activate adipogenesis, when they are bound to their natural ligands [(S)-15-deoxy-$\Delta^{12,14}$-PGJ$_2$] or synthetic ligands (thiazolidinediones or glitazones). Among these two, the α and γ isoforms regulate the balance from the catabolism and the storage of the long chains of fatty acids. Interestingly, the PPARδ isoform, which is widely expressed in the brain, the colon and the skin, is a potential transcription repressor (Oliver, W. R. et al. *Proc. Natl. Acad. Sci., USA* 2001, 98, 5306-5311), which inhibits the transcriptional activity induced by the α and γ isoforms. The role of the PPARδ receptors on anti-lipid oxidation and anti-adipogenesis opens important and promising perspectives for the therapeutic control of obesity and type II diabetes.

One series of fatty acids and of eicosanoids binds to and activates the PPARγ receptors at micromolar concentrations. In contrast with the PPARα receptor, the PPARγ receptor preferentially binds to polyunsaturated fatty acids, such as linoleic acid, linolenic acid, arachidonic acid and eicosapentaenoic acid (EPA).

It has especially been described in WO 96/33724 that PPARγ-selective compounds, such as a prostaglandin-J2 or -D2, are potential active agents for the treatment of obesity and diabetes.

Moreover, the assignee hereof has already described in WO 02/12210 and WO 03/055867 the use of biaromatic compounds that activate PPARγ type receptors in the preparation of a pharmaceutical composition, the composition being intended for treating skin disorders associated with an anomaly of epidermal cell differentiation.

Nevertheless, need continues to exist for such novel compounds that have good activity and advantageous pharmaceutical properties.

SUMMARY OF THE INVENTION

Novel PPAR-modulating compounds, preferably agonists or antagonists, advantageously containing an achiral prop-2-enoyl chain, have now been developed whose synthesis is easier due to the fact that these compounds do not contain any asymmetric carbons. Furthermore, these compounds also have the advantage of simplifying the steps of the development: the steps for measuring the bioconversion and the toxicity of the enantiomer are not necessary, and likewise for the measurement of the enantiomeric purity (using a chiral column) on the synthetic intermediates and the final product.

Thus, the present invention features compounds corresponding to the general formula (I) below:

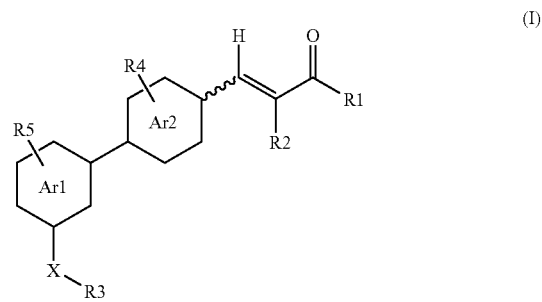

(I)

in which:

R1 is a radical —OR6, a radical —NR6OR6, or a radical NR6R6; wherein R6 is as defined below, R2 is a halogen atom, an alkyl radical having from 1 to 12 carbon atoms, a radical —OR7, a radical —NHR7, or an aralkyl radical; wherein R7 is as defined below;

R3 is an alkyl radical having from 1 to 12 carbon atoms, a cycloalkyl radical having from 3 to 12 carbon atoms, or a sequence —(CH$_2$)$_m$R8; wherein m and R8 are as defined below;

X is the following sequence:

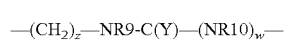

—(CH$_2$)$_z$—NR9-C(Y)—(NR10)$_w$— w, z, R9, R10 and Y are as defined below, m is an integer ranging from 0 to 4 and may have the values 0, 1, 2, 3 or 4;

Y is an oxygen or sulfur atom;

z and w are each the values 0 or 1;

Ar1 and Ar2 are each an aromatic ring having the following formula, optionally substituted with a radical R4 or R5 as defined below):

for Ar1:

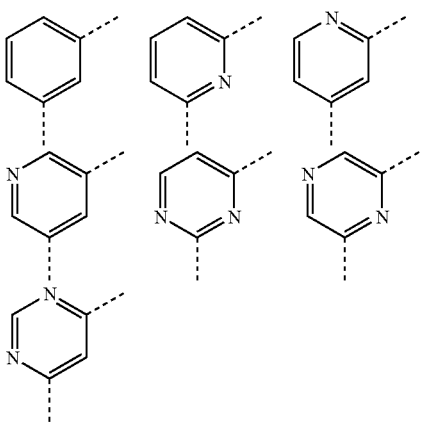

for Ar2:

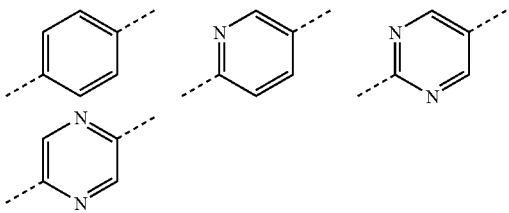

the groups Ar2 and XR3 are in a meta arrangement on the aromatic ring Ar1 and the groups Ar1 and CH=CR2-CO—R1 are in a para arrangement on the aromatic ring Ar2;

R4 and R5, which may be identical or different, are each a hydrogen atom, a halogen atom, an alkyl radical of 1 to 12 carbon atoms, a hydroxyl radical, an alkoxy radical, a polyether radical, an aralkyl radical, an aryl radical, an amino radical that may be substituted with one or two radicals, which may be identical or different, selected from an alkyl radical having from 1 to 12 carbon atoms or an aralkyl radical;

R6 is a hydrogen atom, an alkyl radical having from 1 to 7 carbon atoms, an aryl or an aralkyl radical;

R7 is a hydrogen atom, an alkyl radical having from 1 to 7 carbon atoms, an aryl or an aralkyl radical;

R8 is an alkyl radical having from 1 to 7 carbon atoms, a cycloalkyl radical, an aryl, aralkyl, heteroaryl or heterocycloalkyl radical, a radical —OR11, a substituted or unsubstituted amine function;

R9, R10, which may be identical or different, are each a hydrogen atom or a lower alkyl radical;

R11 is a hydrogen atom, an alkyl radical having from 1 to 7 carbon atoms, an aryl or an aralkyl radical;

and also the pharmaceutically acceptable salts and solvates thereof and/or hydrates thereof.

In particular, X is the following sequence:

—(CH$_2$)$_z$—NR9-C(Y)—(NR10)$_w$— and —(CH$_2$)$_z$— is bonded to Ar1.

In particular, when the compounds according to the invention are in the form of salts, they are salts of an alkali metal, in particular a sodium or potassium salt, or an alkaline-earth metal salt (magnesium or calcium), or salts of organic amines, more particularly of amino acids such as arginine or lysine.

When the compounds according to the invention contain an amine function and are in the form of salts of this amine, these are salts of a mineral acid, for instance hydrochloric acid, sulfuric acid or hydrobromic acid, or salts of an organic acid, for instance acetic acid, triflic acid, tartaric acid, oxalic acid, citric acid or trifluoroacetic acid.

According to the present invention, the term "alkyl radical having from 1 to 12 carbon atoms" means a linear or branched carbon-based chain that may be interrupted with a hetero atom and that may be substituted with one or more radicals selected from a halogen atom, a hydroxyl radical, an alkoxy radical and a heterocyclic radical, and preferably the alkyl radicals are methyl, ethyl, propyl, isopropyl, butyl, tert-butyl, isoamyl, pentyl, hexyl, heptyl, octyl or decyl radicals.

The term "lower alkyl radical" means a radical of 1 to 4 carbon atoms. Lower alkyl radicals will preferably be methyl, ethyl, propyl, cyclopropylmethyl, isopropyl, tert-butyl or n-butyl radicals.

The term "cycloalkyl" means a cyclic alkyl radical having from 3 to 12, preferably from 3 to 10 and more preferably from 3 to 6 carbon atoms, which is unsubstituted or substituted with a halogen atom or an alkyl radical as defined above and preferably, for example, a cyclopropyl, cyclobutyl, cyclopentyl, cyclohexyl, cyclopropylmethyl, cyclobutylmethyl, cyclopentylmethyl or cyclohexylmethyl radical, or a bridged cycloalkyl radical such an adamantyl or a bicyclo[3.2.1]octanyl radical.

The term "aryl radical" means mono-, bi- or polycyclic carbocycles preferably having from 6 to 12 carbon atoms, comprising at least one aromatic radical, for example a phenyl, biphenyl, cinnamyl or naphthyl radical that may be mono- or disubstituted with a halogen atom, a CF$_3$ radical, an alkyl radical of 1 to 12 carbon atoms, an alkoxy radical having from 1 to 7 carbon atoms, a nitro function, a polyether radical, a benzoyl radical, an alkyl ester radical, a carboxylic acid, a hydroxyl function optionally protected with an acetyl or benzoyl radical or an amino function optionally protected with an acetyl or benzoyl radical or optionally substituted with at least one alkyl having from 1 to 12 carbon atoms, an aralkoxy radical, a phenoxy radical or an amide function H2NCO.

The term "aralkyl radical" means an alkyl radical of 1 to 12 carbon atoms, preferably of 1 to 6 carbon atoms and more preferably of 1 to 4 carbon atoms, substituted with an aryl radical or with a heteroaryl radical as defined herein below. The aralkyl radicals that are preferred in the context of the invention are benzyl, phenethyl and 2-naphthylmethyl radicals, a 3-phenylpropyl radical optionally being mono- or disubstituted with a halogen atom, a radical CF$_3$, an alkyl radical having from 1 to 12 carbon atoms, an alkoxy radical having from 1 to 7 carbon atoms, a nitro function, a polyether radical, an aryl radical, a benzoyl radical, an alkyl ester radical, a carboxylic acid, a hydroxyl function optionally protected with an acetyl or benzoyl radical or an amino function optionally protected with an acetyl or benzoyl radical or optionally substituted with at least one alkyl having from 1 to 12 carbon atoms.

The term "halogen atom" means a fluorine, chlorine, bromine or iodine atom.

The term "alkoxy radical having from 1 to 12 carbon atoms" means an oxygen atom substituted with an alkyl radical of 1 to 12 carbon atoms and the alkoxy radicals are preferably methoxy, ethoxy, isopropoxy, tert-butoxy, n-propoxy, n-butoxy, n-pentyloxy, n-hexyloxy, cyclopropylmethoxy, cyclobutylmethoxy, cyclopentylmethoxy or cyclohexylmethoxy.

The term "aralkoxy" means an oxygen atom substituted with an aralkyl radical as defined above. The preferred aralkoxy radical is an optionally substituted benzyloxy radical.

The term "polyether radical" means a radical having from 1 to 7 carbon atoms interrupted with at least two oxygen atoms, and preferably methoxymethoxy, methoxyethoxy, ethoxymethoxy, ethoxyethoxy or methoxyethoxymethoxy radicals.

The term "heteroaryl radical" means an aryl radical interrupted with one or more hetero atoms, such as a pyridyl, furyl, thienyl, isoxazolyl, oxadiazolyl, oxazolyl, isothiazolyl, quinazolinyl, benzothiadiazolyl, benzimidazole, indolyl or benzofuran radical, optionally substituted with at least one halogen, an alkyl radical having from 1 to 12 carbon atoms, an alkoxy radical having from 1 to 7 carbon atoms, an aryl radical, a nitro function, a polyether radical, a benzoyl radical, an alkyl ester radical, a carboxylic acid, a hydroxyl optionally protected with an acetyl or benzoyl radical or an amino function optionally protected with an acetyl or benzoyl radical or optionally substituted with at least one alkyl having from 1 to 12 carbon atoms.

The term "heterocyclic radical" preferably means a morpholinyl, pyrrolidinyl, piperidyl, piperazinyl, 2-oxopiperid-1-yl or 2-oxopyrrolidin-1-yl radical, optionally substituted with at least one alkyl radical having from 1 to 12 carbon atoms, an alkoxy radical having from 1 to 7 carbon atoms, an aryl radical, a nitro function, a polyether radical, a heteroaryl radical, a benzoyl radical, an alkyl ester radical, a carboxylic acid, a hydroxyl optionally protected with an acetyl or benzoyl radical or an amino function optionally protected with an acetyl or benzoyl radical or optionally substituted with at least one alkyl having from 1 to 12 carbon atoms.

The term "alkyl ester radical" means a carboxylate function substituted with an alkyl radical having from 1 to 6 carbon atoms.

Figure 1:
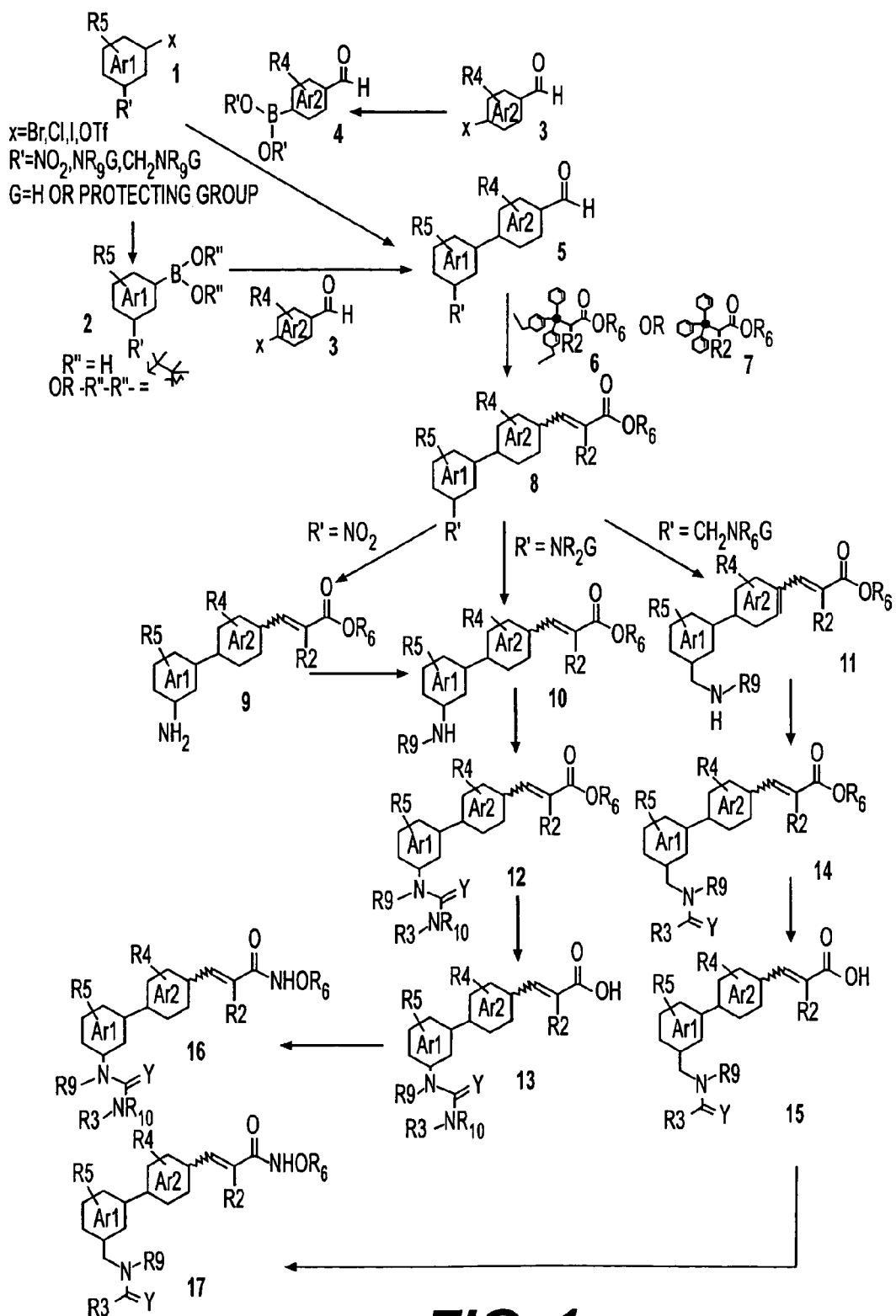
FIGS. 1-5 are reaction schemes illustrating the preparation of the novel biaromatic compounds of the present invention.

DETAILED DESCRIPTION OF BEST MODE AND SPECIFIC/PREFERRED EMBODIMENTS OF THE INVENTION

According to the present invention, the preferred compounds corresponding to the general formula (I) are those having at least one of the following characteristics:

R1 is a radical —OR6, wherein R6 is as defined above;

R2 is an alkyl radical having from 1 to 7 carbon atoms or a radical —OR7, wherein R7 is as defined above;

R3 is an alkyl radical having from 1 to 12 carbon atoms, a cycloalkyl radical or a sequence —(CH$_2$)$_m$R8 with m=0, 1 or 2 and R8 is an aryl or heteroaryl radical;

R4 and R5 are each a hydrogen atom or an alkoxy radical having from 1 to 7 carbon atoms, or a polyether radical;

X is a sequence —NR9-C(Y)—NR10- or a sequence —CH$_2$—NR9C(Y)—;

R9 is preferentially a hydrogen atom or a lower alkyl radical, wherein R10 and Y are as defined above;

Ar1 and Ar2 are each an aromatic ring selected from a phenyl radical and a pyridyl radical.

Also according to the present invention, the particularly preferred compounds corresponding to the general formula (I) are those for which:

R1 is a radical —OR6, wherein R6 is a hydrogen atom;

R2 is a lower alkyl radical, a radical —OR7-, wherein R7 is a lower alkyl radical;

R3 is an alkyl radical having from 3 to 8 carbon atoms, a cyclohexyl radical; a sequence —(CH$_2$)$_m$—R8, wherein R8 is a phenyl radical optionally substituted with a methyl radical, a methoxy radical or a trifluoromethyl radical;

m is equal to 0, 1 or 2;

X is a sequence —NR9-C(Y)—NR10- or a sequence —CH$_2$—NR9C(Y)—, wherein R9 is a hydrogen atom, a methyl radical, wherein R10 is a hydrogen atom and Y is an oxygen atom;

R4 is a hydrogen atom, an alkoxy radical having from 1 to 7 carbon atoms, or a polyether radical;

R5 is a hydrogen atom;

Ar1 and Ar2 are each an aromatic ring selected from a phenyl radical and a pyridyl radical;

and also the pharmaceutically acceptable salts and solvates thereof and/or hydrates thereof.

The compounds of formula (I), and also the pharmaceutically acceptable salts and solvates thereof and/or hydrates thereof, selected from among the compounds below, are more particularly preferred:

1. (Z)-2-Ethoxy-3-{3'-[(methyloctanoylamino)methyl]biphenyl-4-yl}acrylic acid;
2. (Z)-2-Ethoxy-3-{4-[6-(3-heptyl-1-methylureido)pyrid-2-yl]phenyl}acrylic acid;
3. (Z)-2-Ethoxy-3-{4-[6-(1-methyl-3-pentylureido)pyrid-2-yl]phenyl}acrylic acid;
4. (Z)-2-Ethoxy-3-{6-[3-(3-heptyl-1-methylureido)phenyl]pyrid-3-yl}acrylic acid hydrochloride;
5. (E)-3-[3'-(3-Heptyl-1-methylureido)biphenyl-4-yl]-2-methylacrylic acid;
6. (Z)-2-Fluoro-3-[3'-(3-heptyl-1-methylureido)biphenyl-4-yl]acrylic acid;
7. 2-[1-[3'-(3-Heptyl-1-methylureido)biphenyl-4-yl]meth-(E)-ylidene]butyric acid;
8. 2-[1-[3'-(1-Methyl-3-pentylureido)biphenyl-4-yl]meth-(E)-ylidene]pentanoic acid;
9. 2-[1-[3'-(1-Methyl-3-pentylureido)biphenyl-4-yl]meth-(E)-ylidene]butyric acid;
10. (Z)-2-Ethoxy-3-[3'-(1-methyl-3-phenethylureido)biphenyl-4-yl]acrylic acid;
11. (Z)-3-[3'-(3-Butyl-1-methylureido)biphenyl-4-yl]-2-methoxyacrylic acid;
12. Methyl (Z)-3-[3'-(3-butyl-1-methylureido)biphenyl-4-yl]-2-methoxyacrylate;
13. (Z)-2-Methoxy-3-[3'-(1-methyl-3-pentylureido)biphenyl-4-yl]acrylic acid;
14. Methyl (Z)-3-[3'-(3-cyclohexyl-1-methylureido)biphenyl-4-yl]-2-methoxyacrylate;
15. (Z)-3-[3'-(3-Cyclohexyl-1-methylureido)biphenyl-4-yl]-2-methoxyacrylic acid;
16. (Z)-2-Methoxy-3-[3'-(1-methyl-3-phenethylureido)biphenyl-4-yl]acrylic acid;
17. Methyl (Z)-2-methoxy-3-[3'-(1-methyl-3-phenylureido)biphenyl-4-yl]acrylate;
18. (Z)-2-Methoxy-3-[3'-(1-methyl-3-phenylureido)biphenyl-4-yl]acrylic acid;
19. (E)-3-{3'-[(Benzoylmethylamino)methyl]-2-butoxybiphenyl-4-yl}-2-methylacrylic acid;
20. (E)-3-(2-Butoxy-3'-{[(4-methoxybenzoyl)methylamino]methyl}biphenyl-4-yl)-2-methylacrylic acid;
21. (E)-3-(2-Butoxy-3'-{[(3-methoxybenzoyl)methylamino]methyl}biphenyl-4-yl)-2-methylacrylic acid;
22. 2-[1-{3'-[(Benzoylmethylamino)methyl]-2-butoxybiphenyl-4-yl}meth-(E)-ylidene]butyric acid;
23. (Z)-3-[2-Butoxy-3'-(1-methyl-3-phenethylureido)biphenyl-4-yl]-2-ethoxyacrylic acid;
24. (Z)-3-[2-Butoxy-3'-(1-methyl-3-pentylureido)biphenyl-4-yl]-2-methoxyacrylic acid;

25. (Z)-3-[2-Butoxy-3'-(3-heptyl-1-methylureido)biphenyl-4-yl]-2-methoxyacrylic acid;
26. (Z)-3-[2-Butoxy-3'-(1-methyl-3-pentylureido)biphenyl-4-yl]-2-ethoxyacrylic acid;
27. (Z)-3-[2-Butoxy-3'-(3-heptyl-1-methylureido)biphenyl-4-yl]-2-ethoxyacrylic acid;
28. (Z)-3-[2-Butoxy-3'-(3-butyl-1-methylureido)biphenyl-4-yl]-2-methoxyacrylic acid;
29. (Z)-3-[2-Butoxy-3'-(3-butyl-1-methylureido)biphenyl-4-yl]-2-ethoxyacrylic acid;
30. (Z)-3-[2-Butoxy-3'-(3-cyclohexyl-1-methylureido)biphenyl-4-yl]-2-ethoxyacrylic acid;
31. (E)-3-[3'-(3-Heptyl-1-methylureido)-2-propoxybiphenyl-4-yl]-2-methylacrylic acid;
32. (E)-3-[2-Ethoxy-3'-(3-heptyl-1-methylureido)biphenyl-4-yl]-2-methylacrylic acid);
33. 2-[1-[2-Ethoxy-3'-(3-heptyl-1-methylureido)biphenyl-4-yl]meth-(E)-ylidene]butyric acid;
34. (E)-3-[2-Butoxy-3'-(1-methyl-3-pentylureido)biphenyl-4-yl]-2-methylacrylic acid;
35. (E)-3-[2-Butoxy-3'-(3-heptyl-1-methylureido)biphenyl-4-yl]-2-methylacrylic acid;
36. 2-[1-[2-Butoxy-3'-(1-methyl-3-pentylureido)biphenyl-4-yl]meth-(E)-ylidene]butyric acid;
37. 2-[1-[2-Butoxy-3'-(3-heptyl-1-methylureido)biphenyl-4-yl]meth-(E)-ylidene]butyric acid;
38. (Z)-2-Ethoxy-3-[2-(2-ethoxyethoxy)-3'-(1-methyl-3-pentylureido)biphenyl-4-yl]acrylic acid;
39. (Z)-3-[2-(2-Ethoxyethoxy)-3'-(1-methyl-3-pentylureido)biphenyl-4-yl]-2-methoxyacrylic acid;
40. (E)-3-[2-Butoxy-3'-(3-heptyl-1-methylureido)biphenyl-4-yl]-2-methoxyacrylic acid;
41. L-Arginine salt of (Z)-2-ethoxy-3-[3'-(3-heptyl-1-methylureido)biphenyl-4-yl]acrylic acid;
42. L-Arginine salt of (Z)-2-ethoxy-3-[3'-(1-methyl-3-pentylureido)biphenyl-4-yl]acrylic acid;
43. (Z)-3-[3'-(3-Butyl-1-methylureido)biphenyl-4-yl]-2-ethoxyacrylic acid;
44. (Z)-3-[3'-(3-Cyclohexyl-1-methylureido)biphenyl-4-yl]-2-ethoxyacrylic acid;
45. (Z)-2-Ethoxy-3-(3'-{3-[2-(4-methoxyphenyl)ethyl]-1-methylureido}biphenyl-4-yl)acrylic acid;
46. (Z)-2-Ethoxy-3-[3'-(1-methyl-3-phenylureido)biphenyl-4-yl]acrylic acid;
47. (Z)-2-Ethoxy-3-[3'-(1-methyl-3-p-tolylureido)biphenyl-4-yl]acrylic acid;
48. (Z)-2-Ethoxy-3-{3'-[1-methyl-3-(4-trifluoromethylphenyl)ureido]biphenyl-4-yl}acrylic acid;
49. (Z)-3-[3'-(3-Heptyl-1-methylureido)biphenyl-4-yl]-2-methoxyacrylic acid;
50. 2-[1-[3'-(3-Heptyl-1-methylureido)biphenyl-4-yl]meth-(E)-ylidene]pentanoic acid;
51. (Z)-3-[2-Butoxy-3'-(3-heptylureido)biphenyl-4-yl]-2-methoxyacrylic acid;
52. (Z)-2-Ethoxy-3-[3'-(3-hexyl-1-methylureido)biphenyl-4-yl]acrylic acid;
53. (Z)-3-{3'-[3-(4-Butylphenyl)-1-methylureido]biphenyl-4-yl}-2-ethoxyacrylic acid;
54. (Z)-2-Ethoxy-3-{3'-[3-(4-ethylphenyl)-1-methylureido]biphenyl-4-yl}acrylic acid;
55. (Z)-2-Ethoxy-3-{3'-[3-(4-ethoxyphenyl)-1-methylureido]biphenyl-4-yl}acrylic acid;
56. (Z)-3-{3'-[3-(4-Butoxyphenyl)-1-methylureido]biphenyl-4-yl}-2-ethoxyacrylic acid;
57. (E)-2-Methyl-3-[3'-(1-methyl-3-pentylureido)biphenyl-4-yl]acrylic acid;
58. (E)-3-[3'-(3-Heptyl-1-methylthioureido)biphenyl-4-yl]-2-methylacrylic acid;
59. (Z)-2-Ethoxy-3-{3'-[1-methyl-3-(3-phenylpropyl)ureido]biphenyl-4-yl}acrylic acid;
60. (Z)-2-Ethoxy-3-(3'-{[(3-1H-indol-3-ylpropionyl)methylamino]methyl}biphenyl-4-yl)acrylic acid;
61. (Z)-2-Benzyloxy-3-[3'-(3-heptyl-1-methylureido)biphenyl-4-yl]acrylic acid;
62. Methyl (Z)-2-ethoxy-3-[3'-(3-heptyl-1-methylureido)biphenyl-4-yl]acrylate;
63. Benzyl (Z)-2-ethoxy-3-[3'-(3-heptyl-1-methylureido)biphenyl-4-yl]acrylate;
64. Phenyl (Z)-2-ethoxy-3-[3'-(3-heptyl-1-methylureido)biphenyl-4-yl]acrylate;
65. (Z)-3-[3'-(3-Heptyl-1-methylureido)biphenyl-4-yl]-2-propoxyacrylic acid;
66. (Z)-2-Ethoxy-3-[3'-(1-methyl-3-naphthalen-2-ylureido)biphenyl-4-yl]acrylic acid;
67. (Z)-3-{3'-[3-(4-Dimethylaminophenyl)-1-methylureido]biphenyl-4-yl}-2-ethoxyacrylic acid;
68. (Z)-3-[3'-(3-Benzo[1.2.5]thiadiazol-5-yl-1-methylureido)biphenyl-4-yl]-2-ethoxyacrylic acid;
69. (Z)-2-Ethoxy-3-(3'-{[methyl-(1-methylpiperidine-3-carbonyl)amino]methyl}biphenyl-4-yl)acrylic acid;
70. (Z)-2-Ethoxy-3-[3'-(3-heptyl-1-methylureido)biphenyl-4-yl]acrylic acid;
71. (Z)-2-Ethoxy-3-[3'-(1-methyl-3-pentylureido)biphenyl-4-yl]acrylic acid;
72. (Z)-3-[3'-(3-Hexyl-1-methylureido)biphenyl-4-yl]-2-methoxyacrylic acid;
73. (E)-3-{3'-[(Benzoylmethylamino)methyl]biphenyl-4-yl}-2-methylacrylic acid;
74. Ethyl (Z)-2-Ethoxy-3-{3'-[(methyloctanoylamino)methyl]biphenyl-4-yl}acrylate;
75. Ethyl (Z)-2-Ethoxy-3-[3'-(3-heptyl-1-methylureido)biphenyl-4-yl]acrylate;
76. Ethyl (Z)-2-Ethoxy-3-[3'-(1-methyl-3-pentylureido)biphenyl-4-yl]acrylate;
77. Ethyl (E)-3-[3'-(3-Heptyl-1-methylureido)biphenyl-4-yl]-2-methylacrylate;
78. (Z)-2-Ethoxy-3-(3'-{3-[2-(4-methoxyphenyl)ethyl]-1-methylureido}biphenyl-4-yl)acrylic acid;
79. (Z)-2-Ethoxy-3-{3'-[1-methyl-3-(4-trifluoromethylphenyl)ureido]biphenyl-4-yl}acrylic acid;
80. (Z)-2-Ethoxy-3-[3-fluoro-3'-(3-hexyl-1-methylureido)biphenyl-4-yl]acrylic acid;
81. (Z)-2-Methoxy-3-[3-fluoro-3'-(3-pentyl-1-methylureido)biphenyl-4-yl]acrylic acid;
82. (Z)-2-Ethoxy-3-[2-fluoro-3'-(3-hexyl-1-methylureido)biphenyl-4-yl]acrylic acid;
83. (Z)-2-Methoxy-3-[2-fluoro-3'-(3-pentyl-1-methylureido)biphenyl-4-yl]acrylic acid;
84. (Z)-2-Ethoxy-3-[2'-methyl-5'-(1-methyl-3-pentylureido)biphenyl-4-yl]acrylic acid;
85. (Z)-2-Methoxy-3-[2'-methyl-5'-(1-methyl-3-pentylureido)biphenyl-4-yl]acrylic acid;
86. (Z)-2-Ethoxy-3-[2-methyl-3'-(3-pentyl-1-methylureido)biphenyl-4-yl]acrylic acid;
87. (Z)-2-Methoxy-3-[2-methyl-3'-(3-pentyl-1-methylureido)biphenyl-4-yl]acrylic acid;
88. (Z)-2-Ethoxy-3-(3'-{[(4-methoxybenzoyl)methylamino]methyl}-2-methylbiphenyl-4-yl)acrylic acid;
89. (Z)-2-Methoxy-3-(3'-{[(4-methoxybenzoyl)methylamino]methyl}-2-methylbiphenyl-4-yl)acrylic acid;
90. (Z)-2-Ethoxy-3-(2-methoxy-3'-{[methyl-(4-trifluoromethylbenzoyl)amino]methyl}biphenyl-4-yl)acrylic acid;

91. (Z)-2-Methoxy-3-(2-methoxy-3'-{[methyl-(4-trifluoromethylbenzoyl)amino]methyl}biphenyl-4-yl)acrylic acid;
92. (Z)-3-(4-{6-[3-(4-Butoxyphenyl)-1-methylureido]pyrid-2-yl}phenyl)-2-ethoxyacrylic acid;
93. (E)-2-Methyl-3-{4-[6-(1-methyl-3-pentylureido)pyrid-2-yl]phenyl}acrylic acid;
94. (E)-3-{4-[6-(3-Heptyl-1-methylureido)pyrid-2-yl]phenyl}-2-methylacrylic acid;
95. 2-[1-{6-[3-(3-Heptyl-1-methylureido)phenyl]pyrid-3-yl}meth-(E)-ylidene]pentanoic acid;
96. (Z)-2-Fluoro-3-{4-[4-(3-heptyl-1-methylureido)pyrid-2-yl]phenyl}acrylic acid;
97. (Z)-2-Ethoxy-3-{4-[4-(3-heptyl-1-methylureido)pyrimidin-2-yl]phenyl}acrylic acid;
98. (Z)-2-Methoxy-3-{4-[6-(1-methyl-3-pentylureido)pyrid-2-yl]phenyl}acrylic acid;
99. (E)-2-{4-[6-(1-Methyl-3-pentylureido)pyrid-2-yl]benzylidene}butyric acid;
100. (Z)-2-Ethoxy-3-{6-[3-(1-methyl-3-pentylureido)phenyl]pyrid-3-yl}acrylic acid;
101. Ethyl (Z)-2-ethoxy-3-{4-[6-(3-heptyl-1-methylureido)pyrid-2-yl]phenyl}acrylate;
102. Ethyl (Z)-2-ethoxy-3-{4-[6-(1-methyl-3-pentylureido)pyrid-2-yl]phenyl}acrylate;
103. Ethyl (Z)-2-ethoxy-3-{6-[3-(3-heptyl-1-methylureido)phenyl]pyrid-3-yl}acrylate;
104. (E)-2-Methyl-3-{5-[3-(1-methyl-3-pentylureido)phenyl]pyrazin-2-yl}acrylic acid;
105. (Z)-2-Ethoxy-3-{4-[2-(3-heptyl-1-methylureido)pyrimidin-4-yl]phenyl}acrylic acid;
106. (Z)-2-Ethoxy-3-{6-[3-(3-heptyl-1-methylureido)phenyl]pyrid-3-yl}-N-hydroxyacrylamide;
107. (Z)-2-Ethoxy-3-{6-[3-(3-heptyl-1-methylureido)phenyl]pyrid-3-yl}-N-methoxyacrylamide;
108. (Z)-3-{6-[3-(3-Butyl-1-methylureido)phenyl]pyrid-3-yl}-2-methoxyacrylic acid;
109. (Z)-3-{6-[3-(3-Heptyl-1-methylureido)phenyl]pyrid-3-yl}-2-methoxyacrylic acid;
110. (Z)-2-Methoxy-3-{6-[3-(1-methyl-3-pentylureido)phenyl]pyrid-3-yl}acrylic acid;
111. (Z)-2-Ethoxy-3-[3'-(3-heptyl-1-methylureido)biphenyl-4-yl]-N-hydroxyacrylamide;
112. (Z)-2-Ethoxy-3-[3'-(3-heptyl-1-methylureido)biphenyl-4-yl]-N-methoxyacrylamide;
113. (Z)-3-[3'-(3-Butyl-1-methylureidomethyl)biphenyl-4-yl]-2-ethoxyacrylic acid;
114. (Z)-2-Ethoxy-3-(4-{6-[3-(4-methoxyphenyl)-1-ethylureido]pyrid-2-yl}phenyl)acrylic acid; and
115. (Z)-2-Ethylamino-3-{3'-[1-methyl-3-(3-phenylpropyl)ureido]biphenyl-4-yl}acrylic acid.

The general description of methods for preparing the compounds of formula (I) is given below, with reference to the reaction schemes in FIGS. 1, 2, 3, 4 and 5, in which the aromatic rings Ar1 and Ar2 are represented in the form of a 6-membered ring. In these schemes and in the description of the process that follows, unless otherwise specified, all the substituents are as defined for the compounds of formula (I).

As illustrated in the scheme of FIG. 1, compounds 12, 13, 14, 15, 16 and 17 corresponding to the general formula (I) may be obtained from compound 8 of formula:

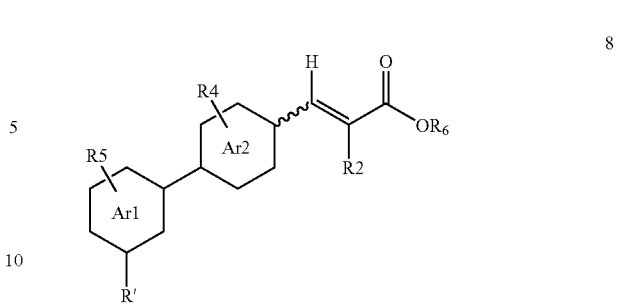

in which R2, R4, R5, R6, Ar1, Ar2 are as defined for the compounds of formula (I) and R' is —NO₂, —NR9G, —CH2-NR9G, with R9 as defined for the compounds of formula (I) and g being an amine-protecting group or a hydrogen atom.

After reducing the nitro group of 8 to an amine group or after deprotecting the amine of 8, the process comprises the following steps:

a) either an addition to an isocyanate or a thioisocyanate, or alternatively a reaction with nitrophenyl chloroformate followed by a reaction with an amine for compounds in which R' is —NHR9; or an addition to a carboxylic acid halide or a thiocarboxylic acid halide for the compounds for which R' is —CH2-NHR9;

b) optionally, a saponification reaction of the compounds obtained in a) in the presence of sodium hydroxide, for example, in a mixture of tetrahydrofuran, methanol and water, c) optionally, a reaction of the compounds obtained in b) with oxalyl chloride followed by a reaction with hydroxylamine or the O-substituted hydroxylamine.

The production of compound 8 may be according to various synthetic routes, which are specified in the schemes of FIGS. 1, 2, 3 and 4.

According to the scheme of FIG. 1, compound 1 with R' equal to NR9G may be obtained from the commercial amine derivative by monoprotection with a protecting group G, for example of "Boc", "Fmoc" or acetyl type, followed by an alkylation with an alkyl halide in the presence of a base, for instance sodium hydride. Compound 1 for which R' is equal to CH₂NR₉ g may be prepared, for example, by a reductive amination reaction on an aldehyde function. The compounds 1 for which R' is a nitro function are commercially available.

The boronic acid 2 may be obtained from compound 1 by using standard conditions, for example by reaction with butyllithium followed by an addition to trimethyl borate. Compound 2 may also be a pinacol borane ester prepared by reacting compound 1 and bis-pinacolatodiborane in the presence of a palladium catalyst.

The boronic acid 4 is commercially available or is obtained after protecting the aldehyde 3 in the form of a dioxolane, for example, by reaction with butyllithium followed by an addition to trimethyl borate. Compound 4 may also be a pinacol borane ester prepared by reacting compound 3 and bis-pinacolatodiborane in the presence of a palladium catalyst.

Compound 5 is obtained via a Suzuki coupling from compound 2 and compound 3 prepared beforehand or commercially available, or alternatively via Suzuki coupling from compound 4 and compound 1.

Compound 8 is prepared via a Wittig or Horner-Emmons reaction from the aldehyde 5 and the triphenylphosphanylidene derivative 7 or the phosphonate 6, commercially available or prepared beforehand from the corresponding chloro derivative.

In the case of a radical R' equal to a nitro function, the amine derivative 9 is obtained via reduction in the presence of a mixture of iron in hydrochloric acid or acetic acid, for example. The intermediate 10 may then be obtained by alkylation with an alkyl halide in the presence of a base such as sodium hydride, the amine being protected with a protecting group, if necessary.

Compounds 12 and 14 correspond to the compounds (I) in which R1=—OR6. After deprotection of the amine 8, the compounds 12 may be prepared by reacting the compounds 10 with an isocyanate or a thioisocyanate, or alternatively by reacting the compounds 10 with 4-nitrophenyl chloroformate followed by a reaction with an amine. Similarly, after deprotection of the amine 8, the compounds 14 may be prepared by addition of the compounds 11 to a carboxylic acid halide or to a thiocarboxylic acid halide.

By saponification reaction of compounds 12 and 14 in the presence of sodium hydroxide in a mixture of tetrahydrofuran, methanol and water, compounds 13 and 15 corresponding to the compounds of formula (I) in which R1=—OH, are respectively obtained.

Compounds 16 and 17 corresponding to the compounds of formula (I) in which R1=—NHOR6 may be obtained from the acids 13 and 15 by reaction with oxalyl chloride followed by a reaction with hydroxylamine or with the O-substituted hydroxylamine, which is preferably commercially available.

Figure 2:
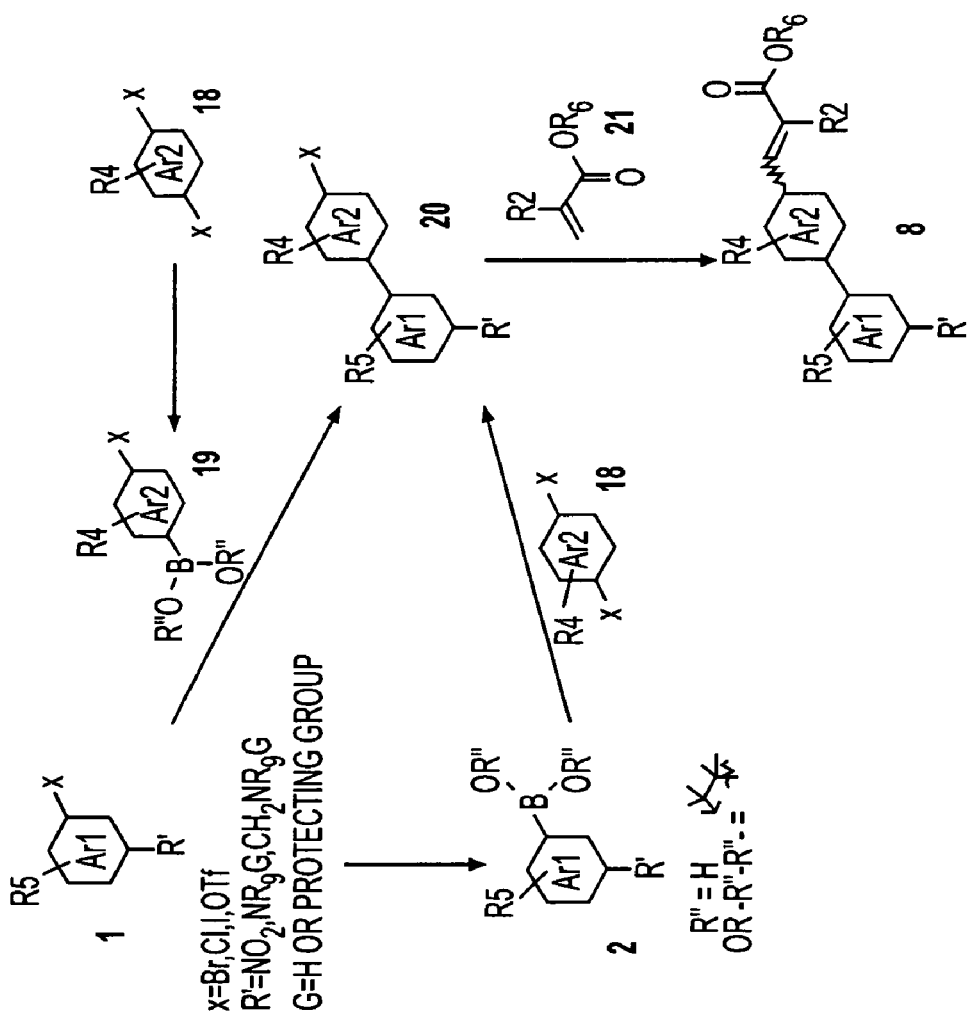

The reaction scheme of FIG. 2 describes another method for obtaining compound 8.

A coupling of Suzuki type from compound 2 and the commercially available compound 18 or from compound 1 and compound 19 prepared beforehand from compound 18 leads to the intermediate 20. The intermediate 8 is then obtained via a coupling of Heck type from compound 20 and the commercial acrylate 21, in the presence of a palladium catalyst.

Figure 3:
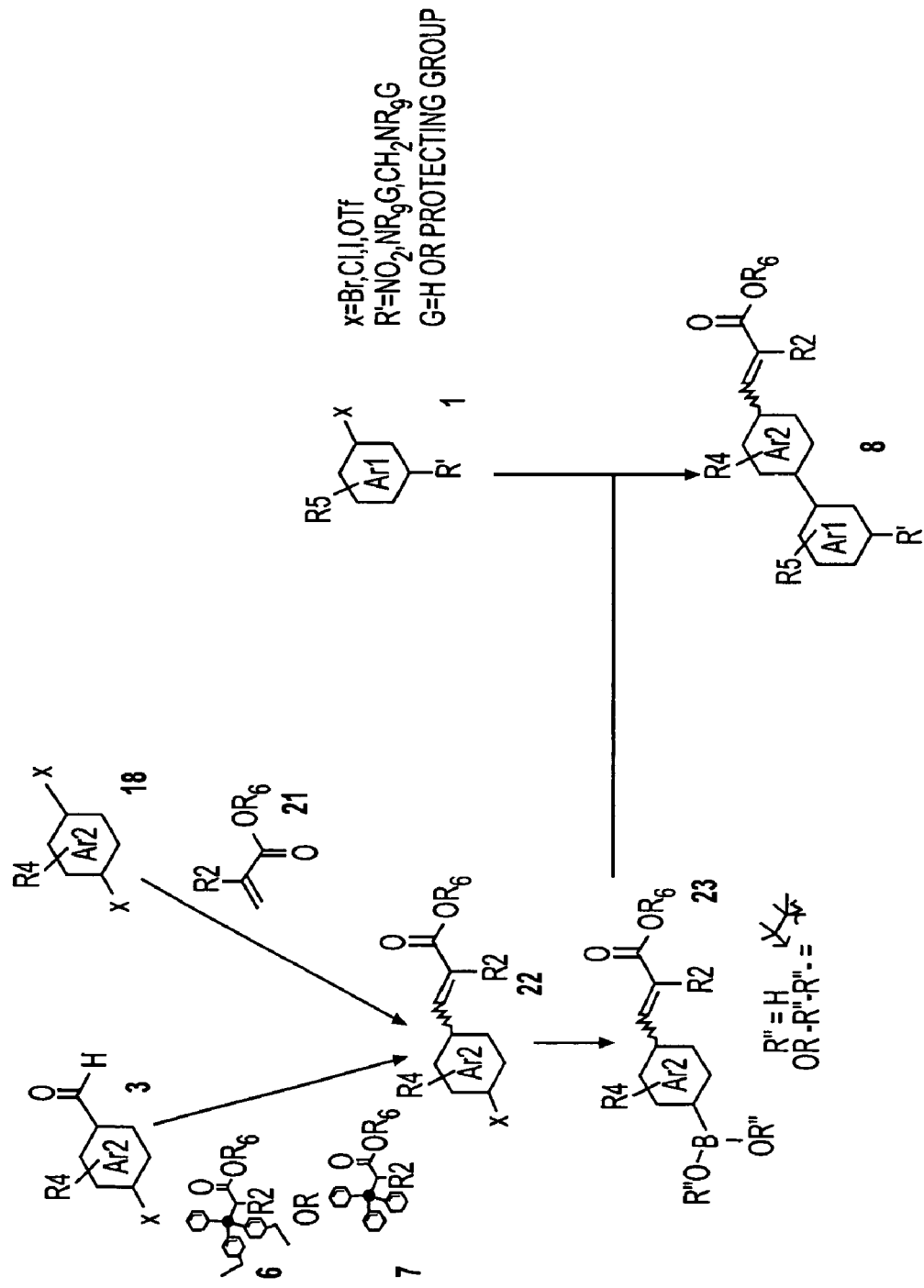

Another method for obtaining compound 8 is described in the reaction scheme of FIG. 3.

Via a Horner-Emmons or Wittig reaction from the aldehyde 3 and the phosphonate 6 or the triphenylphosphanylidene derivative 7, compound 22 is obtained. This intermediate 22 may also be obtained via a coupling of Heck type from compound 18 and the commercial acrylate 21, in the presence of a palladium catalyst. The intermediate 23 in the form of a pinacol borane ester is prepared by reacting compound 22 and bis-pinacolatodiborane in the presence of a palladium catalyst. Compound 8 is then obtained via Suzuki coupling from compound 23 and compound 1.

Figure 4:
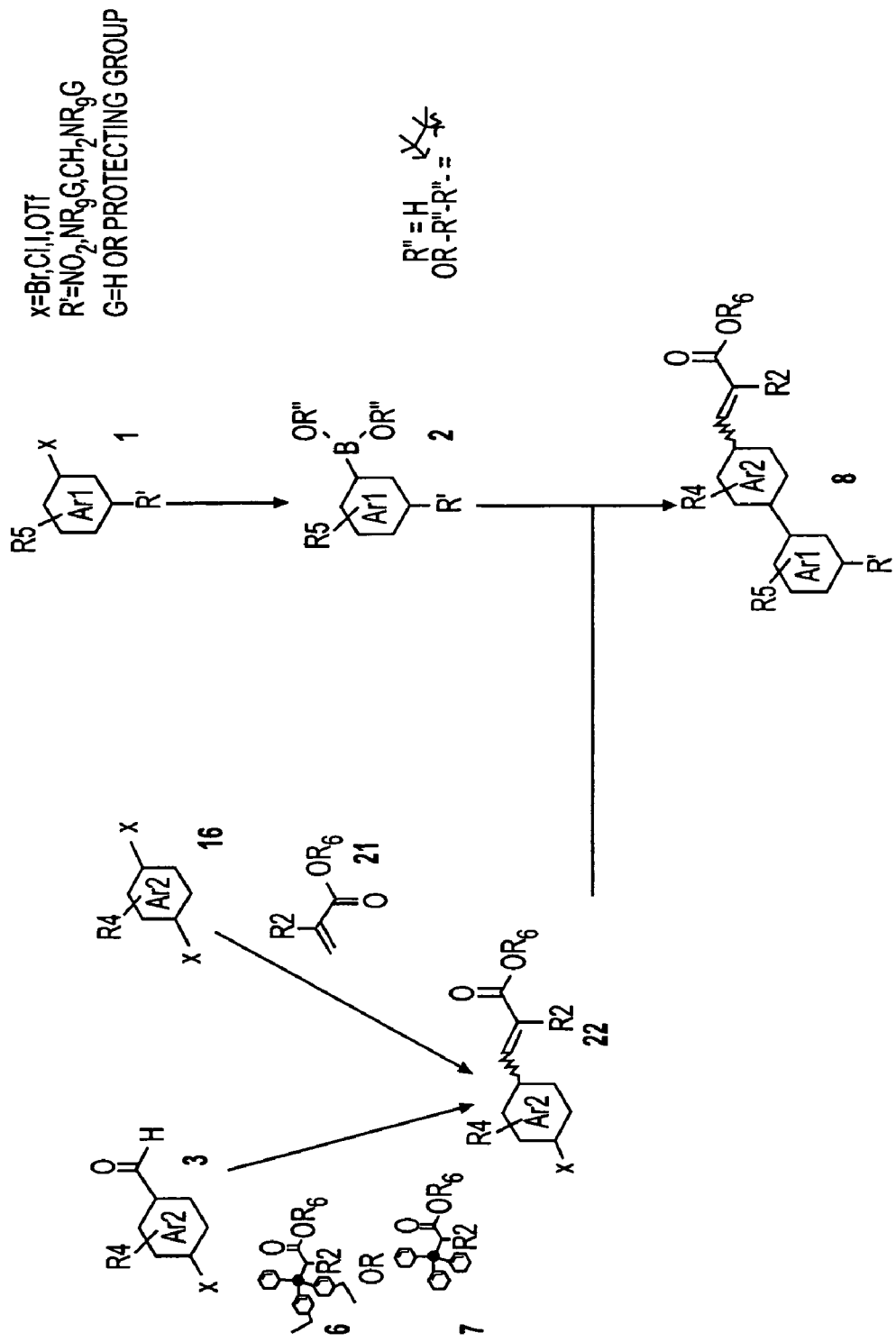

The intermediate 8 may also be obtained via a coupling of Suzuki type from compound 22 and compound 2, as illustrated in the reaction scheme of FIG. 4.

Figure 5:
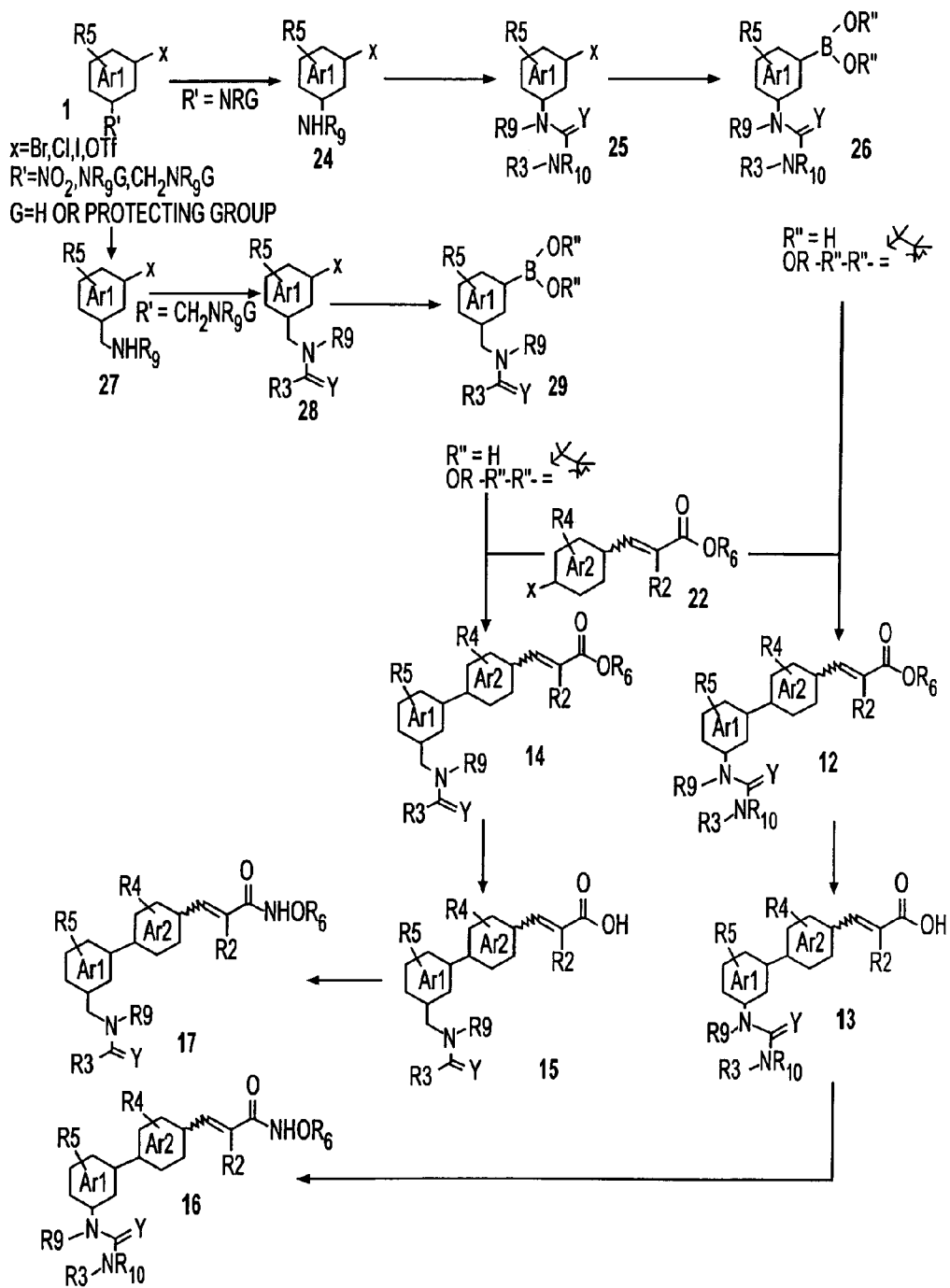

Compounds 12, 13, 14, 15, 16 and 17 corresponding to the general formula (I) may also be obtained according to the reaction scheme of FIG. 5.

After deprotection of the amine 1, compound 25 may be obtained by addition of compound 24 to an isocyanate or to a thioisocyanate. Compound 28 may be obtained after deprotection of the amine 1 by reacting compound 27 with a carboxylic acid halide or with a thiocarboxylic acid halide.

The boronic acids 26 and 29 may be obtained from compounds 25 and 28, respectively, using standard conditions, for example by reaction with butyllithium followed by an addition to trimethyl borate or triisopropyl borate. Compounds 26 and 29 may also be pinacol borane esters prepared, respectively, by reacting compounds 25 and 28 with bis-pinacolatodiborane in the presence of a palladium catalyst.

Compounds 12 and 14 are obtained via a Suzuki coupling from compound 22 prepared beforehand as described in Scheme 3 and, respectively, compounds 26 and 29. The production of compounds 13, 15, 16 and 17 is identical to that described in Scheme 1.

The functional groups that may be present in the reaction intermediates used in the process may be protected, either in permanent form or in temporary form, with protecting groups that ensure an unequivocal synthesis of the expected compounds. The protection and deprotection reactions are performed according to techniques that are well known to those skilled in the art. The term "temporary protecting group for amines, alcohols or carboxylic acids" means protecting groups such as those described in "Protective Groups in Organic Chemistry", published by McOmie J. W. F., Plenum Press, 1973, in "Protective Groups in Organic Synthesis", 2nd edition, Greene T. W. and Wuts P. G. M., published by John Wiley and Sons, 1991 and in "Protecting Groups", Kocienski P. J., 1994, Georg Thieme Verlag.

The compounds (I) according to the invention, and also the salts, solvates and/or hydrates thereof, have modulatory properties on receptors of PPAR type.

The term "modulate" refers to the regulation of the receptors of PPAR type and to the biological activities associated with the PPAR signaling pathway.

The modulation may be an over-regulation (activation, stimulation, action of agonists) or an under-regulation (inhibition, suppression, action of antagonists).

The mode of action of the modulators may be direct, for example by binding of ligand type to a PPAR receptor, or indirect, for example by binding and/or modification of another molecule, which is itself a ligand or activator of a PPAR receptor, or alternatively by stimulating the synthesis of PPAR receptor ligands.

The modulation also includes a change in the bioactivity of the agonist ligand with respect to the PPAR receptors (for example binding and/or activation of the receptor) and also changes of ligand at the cellular level.

This modulatory activity on the PPARα, δ and γ receptors is measured in a transactivation test and quantified by means of the dissociation constant Kdapp (apparent Kd), as described herein below. The preferred compounds of the present invention have a dissociation constant of less than or equal to 500 nM and advantageously less than or equal to 100 nM.

Preferably, the compounds are modulators of receptors of specific PPARγ type, i.e., they have a ratio from the Kdapp for the PPARα or PPARδ receptors, and the Kdapp for the PPARγ receptors, of greater than or equal to 10. Preferably, this ratio PPARα/PPARγ or PPARδ/PPARγ is greater than or equal to 50 and more advantageously greater than or equal to 100.

The present invention also features, as medicaments, the compounds of formula (I) as described above, and also the pharmaceutically acceptable salts and solvates thereof and/or hydrates thereof.

The present invention also features formulation of the compounds of formula (I) into compositions for regulating and/or restoring skin lipid metabolism.

The compounds according to the invention are particularly useful in the following fields of treatment:

1) for treating dermatological complaints, disorders and afflictions associated with a keratinization disorder relating to cell differentiation and proliferation, especially for treating common acne, comedones, polymorphs, acne rosacea, nodulocystic acne, acne conglobata, senile acne, and secondary acnes such as solar acne, medication-related acne or occupational acne;

2) for treating other types of keratinization disorders, especially ichthyosis, ichthyosiform conditions, Darier's disease, palmoplantar keratoderma, leukoplakia and leukoplakiform conditions, and cutaneous or mucous (buccal) lichen;

3) for treating other dermatological complaints/afflictions with an inflammatory immunoallergic component, with or without cell proliferation disorder, and especially all forms of psoriasis, whether cutaneous, mucous or ungual, and even psoriatic rheumatism, or cutaneous atopy, such as eczema, or respiratory atopy, or alternatively gingival hypertrophy;

4) for treating all dermal or epidermal proliferations, whether benign or malignant, and whether of viral origin or otherwise, such as common warts, flat warts and verruciform epidermodysplasia, oral or florid papillomatoses, T lymphoma, and proliferations that may be induced by ultraviolet radiation, especially in the case of basal cell and spinal cell epithelioma, and also any precancerous skin lesion such as keratoacanthomas;

5) for treating other dermatological disorders such as immune dermatoses, such as lupus erythematosus, immune bullous diseases and collagen diseases, such as scleroderma;

6) in the treatment of dermatological or general complaints/afflictions with an immunological component;

7) in the treatment of skin disorders caused by exposure to UV radiation, and also for repairing or combating aging of the skin, whether photoinduced or chronological aging, or for reducing actinic pigmentations and keratosis, or any pathology associated with chronological or actinic aging, such as xerosis;

8) for combating sebaceous function disorders, such as the hyperseborrhoea of acne, simple seborrhoea or seborrhoeic dermatitis;

9) for preventing or treating cicatrization disorders, or for preventing or repairing stretchmarks;

10) in the treatment of pigmentation disorders, such as hyperpigmentation, melasma, hypopigmentation or vitiligo;

11) in the treatment of lipid metabolism complaints/conditions, such as obesity, hyperlipidaemia, non-insulin-dependent diabetes or syndrome X;

12) in the treatment of inflammatory complaints/afflictions, such as arthritis;

13) in the treatment or prevention of cancerous or precancerous conditions;

14) in the prevention or treatment of alopecia of various origins, especially alopecia caused by chemotherapy or radiation;

15) in the treatment of disorders of the immune system, such as asthma, type I sugar diabetes, multiple sclerosis or other selective dysfunctions of the immune system; and 16) complaints/disorders of the cardiovascular system, such as arteriosclerosis or hypertension.

The present invention also features pharmaceutical or cosmetic compositions comprising, in a physiologically acceptable medium, at least one compound of formula (I) as defined above. The compositions according to the invention thus comprise a physiologically acceptable support or at least one pharmaceutically acceptable excipient, selected according to the desired cosmetic or pharmaceutical form and the selected mode of administration, whether regime or regimen.

The compositions according to the invention may be administered enterally, parenterally, topically or ocularly. The pharmaceutical composition is preferably packaged in a form that is suitable for topical application.

Via the enteral route, the composition, more particularly the pharmaceutical composition, may be in the form of tablets, gel capsules, dragees, syrups, suspensions, solutions, powders, granules, emulsions, lipid or polymeric microspheres, nanospheres or vesicles allowing a controlled release. Via the parenteral route, the composition may be in the form of solutions or suspensions for infusion or for injection.

The compositions according to the invention contain a compound according to the invention, in an amount that is sufficient to obtain the desired cosmetic, prophylactic or therapeutic effect. The compounds according to the invention are generally administered at a daily dose of about 0.001 mg/kg to 100 mg/kg of body weight, in 1 to 3 dosage intakes. The compounds are used systemically, at a concentration generally of from 0.001% to 10% by weight and preferably from 0.01% to 1% by weight, relative to the weight of the composition.

Via the topical route, the pharmaceutical composition according to the invention is more particularly useful for treating the skin and mucous membranes and may be in the form of ointments, creams, milks, pomades, powders, impregnated pads, syndets, solutions, gels, sprays, mousses, suspensions, lotions, sticks, shampoos or washing bases. It may also be in the form of lipid or polymeric microspheres, nanospheres or vesicles or polymer patches and hydrogels allowing a controlled release. This topical composition may be in anhydrous form, in aqueous form or in the form of an emulsion.

The compounds are applied topically at a concentration generally of from 0.001% to 10% by weight and preferably from 0.01% to 1% by weight, relative to the total weight of the composition.

The compounds of formula (I) according to the invention, and also the physiologically acceptable salts and solvates thereof, and/or hydrates thereof, also find application in cosmetics, in particular in body and hair hygiene and more particularly for regulating and/or restoring skin lipid metabolism.

This invention thus also features the cosmetic use of a composition comprising, in a physiologically acceptable support, at least one of the compounds of formula (I), optionally in the form of a physiologically acceptable salt or solvate and/or hydrate, for body or hair hygiene.

The cosmetic composition according to the invention containing, in a cosmetically acceptable support, at least one compound of formula (I) or a physiologically acceptable salt or solvates thereof, and/or hydrate thereof, may especially be in the form of a cream, a milk, a lotion, a gel, a suspension, lipid or polymeric microspheres, nanospheres or vesicles, impregnated pads, solutions, sprays, mousses, sticks, soaps, shampoos or washing bases.

The concentration of compound of formula (I) in the cosmetic composition advantageously ranges from 0.001% to 3% by weight relative to the total weight of the composition.

The pharmaceutical and cosmetic compositions as described above may also contain inert additives, and especially:

wetting agents;
flavor enhancers;
preservatives such as para-hydroxybenzoic acid esters;
stabilizers;
humidity regulators;
pH regulators;
osmotic pressure modifiers;
emulsifiers;
UV-A and UV-B screening agents.

Of course, one skilled in the art will take care to select the optional compound(s) to be added to these compositions such that the advantageous properties intrinsically associated with the present invention are not, or are not substantially, adversely affected by the envisaged addition.

Moreover, in general, the same preferences as those indicated previously for the compounds of formula (I) apply mutatis mutandis to the medicaments, cosmetic and pharmaceutical compositions and administration using the compounds of the invention.

In order to further illustrate the present invention and the advantages thereof, the following specific examples of active compounds are given, as well as specific formulations and biological activities thereof, it being understood that same are intended only as illustrative and in nowise limitative. In said examples to follow, all parts and percentages are given by weight, unless otherwise indicated.

EXAMPLE 1

Synthesis of (Z)-2-ethoxy-3-{3'-[(methyloctanoylamino)methyl]biphenyl-4-yl}acrylic acid

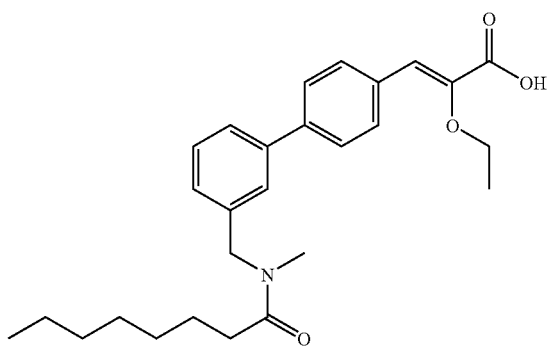 [SMILES: CCCCCCCC(=O)N(C)Cc1cccc(-c2ccc(/C=C(\OCC)C(=O)O)cc2)c1]

a-Ethyl chloroethoxyacetate 20 mL (112 mmol) of ethyl diethoxyacetate, 16 mL (224 mmol) of acetyl chloride and 60 mg (0.2 mmol) of iodine are placed in a round-bottomed flask and heated at 50° C. for 24 hours. The reaction progress is monitored by NMR. The excess acetyl chloride is removed by evaporation under vacuum. 19 g (100%) of ethyl chloroethoxyacetate are obtained in the form of a liquid colored brown by the residual iodine.

b-Ethyl (diethoxyphosphoryl)ethoxyacetate 18.5 g (112 mmol) of ethyl chloroethoxyacetate and 19.2 mL (112 mmol) of triethyl phosphite are placed in a round-bottomed flask and heated at 150° C. for 5 hours. The reaction progress is monitored by NMR. 34 g (100%) of ethyl (diethoxyphosphoryl)ethoxyacetate are obtained directly in the form of a colorless liquid.

c-Ethyl (Z)-3-(4-bromophenyl)-2-ethoxyacrylate 1.7 g (42.5 mmol) of sodium hydride are added portionwise to a solution at 0° C. of 11.4 g (42.5 mmol) of ethyl (diethoxyphosphoryl)ethoxyacetate in 120 mL of tetrahydrofuran. The reaction mixture is stirred for 45 minutes at room temperature, followed by dropwise addition of 6 g (32.7 mmol) of 4-bromobenzaldehyde in 60 mL of tetrahydrofuran. The reaction is slightly exothermic and the reaction mixture is maintained at a temperature of 25-27° C. with an ice bath. When the temperature has stabilized, the reaction mixture is stirred for 20 hours at room temperature.

The reaction is worked up by addition of 100 mL of water and extraction with ethyl acetate. The organic phases are combined, washed with saturated sodium chloride solution and then dried over magnesium sulfate. After filtration, the solvents are evaporated off.

NMR analysis of the crude product obtained shows the presence of 70% of the expected (Z) isomer.

The crude product obtained is purified by chromatography on a column of silica eluted with a 95/5 heptane/ethyl acetate mixture to give 4 g (41%) of the pure (Z) isomer of ethyl 3-(4-bromophenyl)-2-ethoxyacrylate and 3.1 g of a Z/E mixture in the form of yellow oils.

d-N-methyloctanoylcarboxylamide

To a solution of 25 g (0.37 mol) of methylamine hydrochloride in 250 mL of dichloromethane precooled to 0° C. are added dropwise 115 mL (0.81 mol) of triethylamine followed by 70 mL (0.41 mol) of octanoyl chloride. After stirring from 0° C. to room temperature over 2 hours 30 minutes, the triethylammonium chloride precipitate is filtered off and rinsed with dichloromethane. The filtrate is washed with water and the phases are allowed to separate by settling. The organic phase obtained is dried over sodium sulfate, filtered and evaporated under vacuum. 60 g (100%) of N-methyloctanoylcarboxylamide are obtained in the form of a pale yellow solid.

e-Methyl-N-(3-bromobenzyl)octanoylcarboxylamide

A solution of 45 g (0.29 mol) of N-methyloctanoylcarboxylamide in 180 mL of tetrahydrofuran is added dropwise to a suspension of 12.7 g (0.32 mol) of 60% sodium hydride in 90 mL of tetrahydrofuran precooled to 0° C. At the end of the addition, the reaction medium is stirred for about 30 minutes at 0° C. and 75 g (0.29 mol) of 3-bromobenzyl bromide in 180 mL of tetrahydrofuran are then added dropwise. The reaction medium is then stirred at room temperature for 17 hours. After addition of water and ethyl acetate, the reaction medium is extracted with ethyl acetate. The organic phase is washed with water, with saturated aqueous sodium chloride solution, dried over sodium sulfate, filtered and evaporated. The residue obtained is purified by chromatography on a column of silica eluted with a 75/25 heptane/ethyl acetate mixture. 74 g (77%) of N-methyl-N-(3-bromobenzyl)octanoylcarboxylamide are obtained.

f-N-Methyl-N-[3-(4,4,5,5-tetramethyl[1.3.2]dioxaborolan-2-yl)benzyl]octanoylcarboxylamide A mixture of 74 g (0.23 mol) of N-methyl-N-(3-bromobenzyl)octanoylcarboxylamide, 67 g (0.68 mol) of potassium acetate and 61 g (0.24 mol) of bis-pinacoldiborane in 740 mL of dimethylformamide is degassed with nitrogen for 15 minutes, 7.4 g (9.1 mmol) of dichloro[111'-bis(diphenylphosphino)ferrocene]palladium are then added and the reaction medium is heated at 100-110° C. for 3 hours. After addition of water and ethyl acetate, the reaction medium is extracted with ethyl acetate. The organic phase is washed with water and then with saturated sodium chloride solution, dried over sodium sulfate, filtered and evaporated. The residue obtained is purified by chromatography on a column of silica eluted with an 80/20 heptane/ethyl acetate mixture. 64 g (76%) of N-methyl-N-[3-(4,4,5,5-tetramethyl[1.3.2]dioxaborolan-2-yl)benzyl]octanoylcarboxylamide are obtained.

g-Ethyl (Z)-2-ethoxy-3-{3'-[(methyloctanoylamino) methyl]biphenyl-4-yl}acrylate 0.7 g (2.4 mmol) of ethyl (Z)-3-(4-bromophenyl)-2-ethoxyacrylate, 1.3 g (3.5 mmol) of N-methyl-N-[3-(4,4,5,5-tetramethyl[1.3.2]dioxaborolan-2-yl)benzyl]octanoylcarboxylamide and 1.1 g (7.2 mmol) of caesium fluoride are dissolved in 70 mL of diethylene glycol dimethyl ether. After bubbling nitrogen through the reaction mixture for 15 minutes, 0.12 g (0.14 mmol) of dichloro[1,1'-bis(diphenylphosphino)ferrocene]palladium is added. The reaction mixture is heated at 70° C. for 18 hours with vigorous stirring. After cooling, the reaction is worked up by addition of 60 mL of water and extraction with ethyl acetate. The organic phases are combined, washed with saturated aqueous sodium chloride solution and then dried over sodium sulfate. After filtration, the solvents are evaporated off. The crude product obtained is purified by chromatography on a column of silica eluted with an 80/20 heptane/ethyl acetate mixture to give 0.64 g (58%) of ethyl (Z) 2-ethoxy-3-{3'-[(methyloctanoylamino)methyl]biphenyl-4-yl}acrylate in the form of a colorless oil.

h-(Z)-2-ethoxy-3-{3'-[(methyloctanoylamino)methyl]biphenyl-4-yl}acrylic acid 2.10 mL (2.1 mmol) of aqueous 1 M lithium hydroxide solution are added to a solution of 0.64 g (1.4 mmol) of ethyl 2-ethoxy-3-{3'-[(methyloctanoylamino)methyl]biphenyl-4-yl}acrylate in 15 mL of tetrahydrofuran. The reaction mixture is stirred at 68° C. for 24 hours. After cooling, the reaction is worked up by addition of 2.1 mL (2.1 mmol) of aqueous 1 M acetic acid solution and 10 mL of water and extraction with ethyl acetate. The organic phases are combined, washed with saturated aqueous sodium chloride solution and then dried over magnesium sulfate. After filtration, the solvents are evaporated off.

The crude product obtained is purified by chromatography on a column of silica eluted with a 98/2 dichloromethane/methanol mixture to give 0.48 g (80%) of (Z)-2-ethoxy-3-{3'-[(methyloctanoylamino)methyl]biphenyl-4-yl}acrylic acid in the form of a colorless oil.

$^1$H NMR (CDCl$_3$, 400 MHz): 0.90 (t, 3H); 1.26-1.34 (m, 8H); 1.41-1.45 (t, 3H); 1.71-1.77 (m, 2H); 2.44 (t, J=7.3-Hz, 2H); 3.00+3.04 (m, 3H); 4.07-4.16 (m, 2H); 4.65+4.70 (m, 2H); 7.17-7.92 (m, 8H).

EXAMPLE 2

Synthesis of (Z)-2-ethoxy-3-{4-[6-(3-heptyl-1-methylureido)pyrid-2-yl]phenyl}acrylic acid

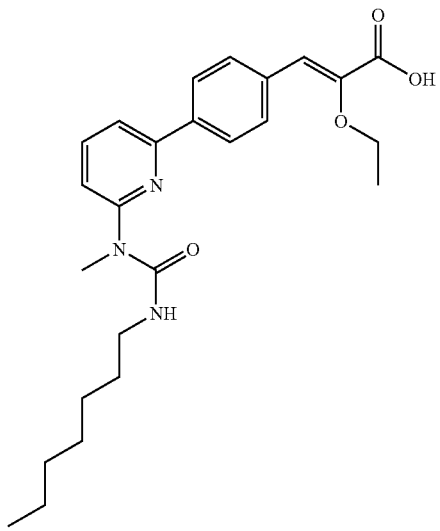 [SMILES: CCCCCCCNC(=O)N(C)c1cccc(-c2ccc(/C=C(\OCC)C(=O)O)cc2)n1]

a-Ethyl (Z)-2-ethoxy-3-[4-(4,4,5,5-tetramethyl[11.3] dioxaborolan-2-yl)phenyl]acrylate 4.0 g (40.1 mmol) of potassium acetate and 5.1 g (20.1 mmol) of bis-pinacoldiborane are added to a solution of 4 g (13.4 mmol) of ethyl (Z)-3-(4-bromophenyl)-2-ethoxyacrylate in 150 mL of dimethylformamide. After bubbling nitrogen through the reaction mixture for 20 minutes, 0.44 g (0.54 mmol) of dichloro[1,1'-bis(diphenylphosphino)ferrocene] palladium is added. The reaction mixture is heated at 80° C. for 18 hours with vigorous stirring.

After cooling, the reaction mixture is worked up by addition of 100 mL of water and extraction with ethyl acetate. The organic phases are combined, washed with saturated sodium chloride solution and then dried over magnesium sulfate. The solvents are evaporated off. The crude product obtained is purified by chromatography on a column of silica eluted with an 80/20 heptane/ethyl acetate mixture to give 2.8 g (61%) of ethyl (Z)-2-ethoxy-3-[4-(4,4,5,5-tetramethyl[1.3]dioxaborolan-2-yl)phenyl]acrylate.

b-6-Methylamino-2-bromopyridine 30 g (0.13 mol) of 2,6-dibromopyridine are added to a solution of 225 mL (2.39 mol) of methylamine in ethanol (33% by weight, Aldrich), precooled to 0° C. The reaction mixture is heated at 80° C., with stirring, for 20 hours, in a glass system, equipped with a manometer. The reaction is monitored by TLC. The reaction medium is cooled to 0° C., and the system is opened. The slightly brown solution thus obtained is concentrated under vacuum to a volume of 60 mL, and water (240 mL) is then added, followed by addition of aqueous sodium carbonate solution (2 N, 240 mL). The beige-colored precipitate formed is filtered off, washed with water and dissolved in dichloromethane (200 mL). The solution is dried over magnesium sulfate and the solvent is evaporated off. Addition of heptane allows the precipitation of 17.5 g (74%) of 6-methylamino-2-bromopyridine in the form of a beige-colored powder.

c-Ethyl (Z)-2-ethoxy-3-[4-(6-methylaminopyrid-2-yl)phenyl]acrylate 1.0 g (2.9 mmol) of ethyl (Z)-2-ethoxy-3-[4-(4,4,5,5-tetramethyl[1.3]dioxaborolan-2-yl)phenyl]acrylate, 0.4 g (2.4 mmol) of 6-methylamino-2-bromopyridine and 1.1 g (7.2 mmol) of caesium fluoride are dissolved in 60 mL of diethylene glycol dimethyl ether. After bubbling nitrogen through the reaction mixture for 20 minutes, 0.1 g (0.15 mmol) of dichloro[1,1'-bis(diphenylphosphino)ferrocene]palladium is added. The reaction mixture is heated at 80° C. for 18 hours with vigorous stirring. After cooling, the reaction is worked up by addition of 60 mL of water and extraction with ethyl acetate. The organic phases are combined, washed with saturated aqueous sodium chloride solution and then dried over magnesium sulfate. After filtration, the solvents are evaporated off. The crude product obtained is purified by chromatography on a column of silica eluted with a 90/10 heptane/ethyl acetate mixture to give 0.6 g (76%) of ethyl (Z)-2-ethoxy-3-[4-(6-methylaminopyrid-2-yl)phenyl]acrylate.

d-Ethyl (Z)-2-ethoxy-3-(4-{6-[methyl-(4-nitrophenoxycarbonyl)amino]pyrid-2-yl}phenyl)acrylate 0.55 g (2.75 mmol) of 4-nitrophenyl chloroformate and then 0.48 mL (2.75 mmol) of diisopropylethylamine are added to a solution of 0.6 g (1.84 mmol) of ethyl (Z)-2-ethoxy-3-[4-(6-methylaminopyrid-2-yl)phenyl]acrylate in 15 mL of dichloromethane. The reaction mixture is stirred for 1 hour 30 minutes at room temperature. The reaction is worked up by addition of 10 mL of water and extraction with dichloromethane. The organic phases are combined and then dried over magnesium sulfate, filtered and the solvent is evaporated off. 1 g (100%) of ethyl (Z)-2-ethoxy-3-(4-{6-[methyl-(4-nitrophenoxycarbonyl)amino]pyrid-2-yl}phenyl)acrylate is obtained in the form of a yellow oil.

e-Ethyl (Z)-2-ethoxy-3-{4-[6-(3-heptyl-1-methylureido)pyrid-2-yl]phenyl}acrylate 0.27 mL (1.84 mmol) of n-heptylamine is added to a solution of 0.45 g (0.92 mmol) of ethyl (Z)-2-ethoxy-3-(4-{6-[methyl-(4-nitrophenoxycarbonyl)amino]pyrid-2-yl}phenyl)acrylate in 15 mL of dimethylformamide. The tube is sealed and rapidly placed in an oil bath preheated to 80° C. The reaction mixture is stirred at 80° C. for 1 hour 30 minutes. After cooling, the reaction is worked up by addition of 10 mL of water and extraction with ethyl acetate. The organic phases are combined, washed with saturated aqueous sodium chloride solution and then dried over magnesium sulfate. After filtration, the solvents are evaporated off. The crude product obtained is purified by chromatography on a column of silica eluted with a 70/30 heptane/ethyl acetate mixture to give 0.29 g (67%) of ethyl (Z)-2-ethoxy-3-{4-[6-(3-heptyl-1-methylureido)pyrid-2-yl]phenyl}acrylate in the form of a pale yellow solid.

f-(Z)-2-ethoxy-3-{4-[6-(3-heptyl-1-methylureido)pyrid-2-yl]phenyl}acrylic acid 0.93 mL (0.93 mmol) of aqueous 1 M lithium hydroxide solution is added to a solution of 0.29 g (0.62 mmol) of ethyl (Z)-2-ethoxy-3-{4-[6-(3-heptyl-1-methylureido)pyrid-2-yl]phenyl}acrylate in 8 mL of tetrahydrofuran. The reaction mixture is stirred at 68° C. for 18 hours. After cooling, the reaction is worked up by addition of 0.93 mL (0.93 mmol) of aqueous 1 M acetic acid solution and 10 mL of water and extraction with ethyl acetate. The organic phases are combined, washed with saturated sodium chloride solution and then dried over magnesium sulfate. After filtration, the solvents are evaporated off. The crude product obtained is purified by chromatography on a column of silica eluted with a 60/40 heptane/ethyl acetate mixture to give 0.10 g (37%) of (Z)-2-ethoxy-3-{4-[6-(3-heptyl-1-methylureido)pyrid-2-yl]phenyl}acrylic acid in the form of a white solid.

$^1$H NMR (DMSO, 400 MHz): 0.86 (t, J=6.8-Hz, 3H); 1.21-1.33 (m, 8H); 1.44 (t, J=7.0-Hz, 3H); 1.62 (m, 2H); 3.42 (3, 2H); 3.49 (s, 3H); 4.12 (q, J=7.0-Hz, 2H); 6.98 (d, J=8.4-Hz, 1H); 7.21 (s, 1H); 7.41 (d, J=7.6-Hz, 1H); 7.80 (t, J=8.2-Hz, 1H); 7.92 (m, 4H).

EXAMPLE 3

Synthesis of (Z)-2-ethoxy-3-{4-[6-(1-methyl-3-pentylureido)pyrid-2-yl]phenyl}acrylic acid

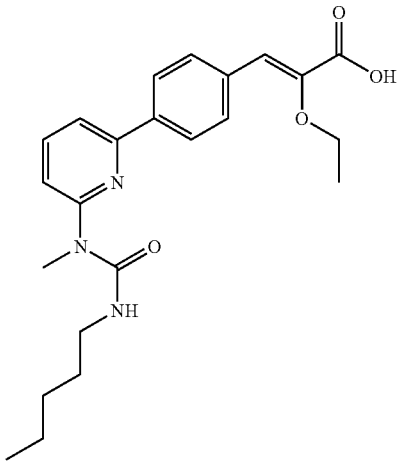 [SMILES: CCCCCNC(=O)N(C)c1cccc(-c2ccc(/C=C(\OCC)C(=O)O)cc2)n1]

a-Ethyl (Z)-2-ethoxy-3-{4-[6-(1-methyl-3-pentylureido)pyrid-2-yl]phenyl}acrylate 0.21 mL (1.8 mmol) of n-pentylamine is added to a solution of 0.45 g (0.9 mmol) of ethyl (Z)-2-ethoxy-3-(4-{6-[methyl-(4-nitrophenoxycarbonyl)amino]pyrid-2-yl}phenyl)acrylate (prepared according to Example 2d) in 15 mL of dimethylformamide. The tube is sealed and rapidly placed in an oil bath preheated to 80° C. The reaction mixture is stirred at 80° C. for 1 hour 30 minutes. After cooling, the reaction is worked up by addition of 10 mL of water and extraction with ethyl acetate. The organic phases are combined, washed with saturated aqueous sodium chloride solution and then dried over magnesium sulfate. The solvents are evaporated off. The crude product obtained is purified by chromatography on a column of silica eluted with a 70/30 heptane/ethyl acetate mixture to give 0.2 g (57%) of ethyl (Z)-2-ethoxy-3-{4-[6-(1-methyl-3-pentylureido)pyrid-2-yl]phenyl}acrylate in the form of a pale yellow solid.

b-(Z)-2-ethoxy-3-{4-[6-(1-methyl-3-pentylureido)pyrid-2-yl]phenyl}acrylic acid 0.68 mL (0.68 mmol) of aqueous 1 M lithium hydroxide solution is added to a solution of 0.20 g (0.45 mmol) of ethyl (Z)-2-ethoxy-3-{4-[6-(1-methyl-3-pentylureido)pyrid-2-yl]phenyl}acrylate in 6 mL of tetrahydrofuran. The reaction mixture is stirred at 68° C. for 18 hours. After cooling, the reaction is worked up by addition of 0.68 mL (0.68 mmol) of aqueous 1 M acetic acid solution and 10 mL of water and extraction with ethyl acetate. The organic phases are combined, washed with saturated aqueous sodium chloride solution and then dried over magnesium sulfate. After filtration, the solvents are evaporated off.

The crude product obtained is purified by chromatography on a column of silica eluted with a 98/2 dichloromethane/methanol mixture to give 100 mg (54%) of (Z)-2-ethoxy-3-{4-[6-(1-methyl-3-pentylureido)pyrid-2-yl]phenyl}acrylic acid in the form of a white solid with a melting point of 162° C.

$^1$H NMR (CDCl$_3$, 400 MHz): 0.82 (t, J=7.0-Hz, 3H); 1.17-1.21 (m, 4H); 1.37 (t, J=7.0-Hz, 3H); 1.56-1.61 (m, 2H); 3.36 (m, 2H); 3.44 (s, 3H); 4.08 (q, J=7.0-Hz, 2H); 6.93 (d, J=8.4-Hz, 1H); 7.05 (s, 1H); 7.36 (d, J=7.6-Hz, 1H); 7.75 (t, J=7.6-Hz, 1H); 7.75 (t, J=7.6-Hz, 1H); 7.83-7.90 (m, 4H).

EXAMPLE 4

Synthesis of (Z)-2-ethoxy-3-{6-[3-(3-heptyl-1-methylureido)phenyl]pyrid-3-yl}acrylic acid hydrochloride

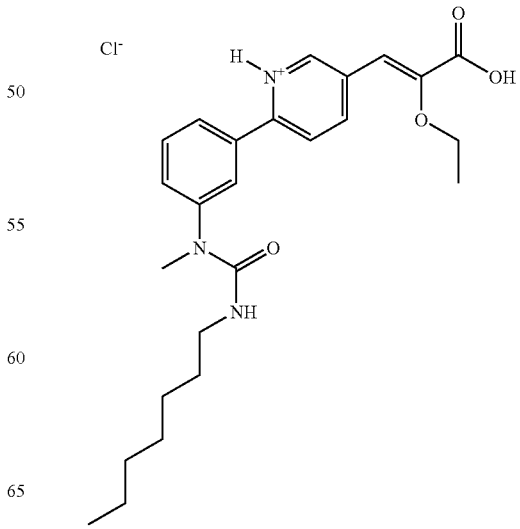

a-tert-Butyl (3-bromophenyl)carbamate

To a mixture of 94 g (549 mmol) of 3-bromoaniline and 1 l of dichloromethane are added portionwise 120 g (549 mmol) of di-tert-butyl dicarbonate, at room temperature. After stirring for 18 hours, the reaction medium is poured into ice-cold water and extracted with dichloromethane. The organic phase is separated out after settling of the phases, dried over magnesium sulfate and evaporated. 138 g (98%) of tert-butyl (3-bromophenyl)carbamate are obtained.

b-tert-Butyl (3-bromophenyl)-N-methylcarbamate

To a solution of 129 g (475 mmol) of tert-butyl (3-bromophenyl)carbamate in 800 mL of dimethylformamide are added portionwise 19 g (475 mmol) of sodium hydride (60% in oil) and the reaction medium is stirred until the evolution of gas has ceased. 29 mL (470 mmol) of methyl iodide are added dropwise and stirring is continued for 18 hours. The reaction medium is poured into ice-cold water and extracted with ethyl acetate. The organic phase is separated out after settling of the phases, dried over magnesium sulfate, filtered and evaporated. 115 g (95%) of tert-butyl (3-bromophenyl)-N-methylcarbamate are obtained.

c-tert-Butyl methyl[3-(4,4,5,5-tetramethyl[1.3.2]dioxaborolan-2-yl)phenyl]carbamate 10.1 g (102.6 mmol) of potassium acetate and 13.1 g (51.4 mmol) of bis-pinacoldiborane are added to a solution of 9.8 g (34.2 mmol) of tert-butyl (3-bromophenyl)-N-methylcarbamate in 300 mL of dimethylformamide. After bubbling nitrogen through the reaction mixture for 15 minutes, 1.1 g (1.4 mmol) of dichloro[1,1'-bis(diphenylphosphino)ferrocene]palladium are added. The reaction mixture is heated at 80° C. for 6 hours with vigorous stirring. After cooling, the reaction is worked up by addition of 300 mL of water and extraction with ethyl acetate. The organic phases are combined, washed with saturated sodium chloride solution and then dried over magnesium sulfate. The solvents are evaporated off. The crude product obtained is purified by chromatography on a column of silica eluted with a 95/5 heptane/ethyl acetate mixture to give 11.2 g (98%) of tert-butyl methyl [3-(4,4,5,5-tetramethyl[1.3.2]dioxaborolan-2-yl)phenyl]carbamate in the form of a colorless oil that crystallizes.

d-(6-Iodopyrid-3-yl)methanol 40 g (145 mmol) of ethyl 6-iodonicotinate diluted in 400 mL of ethanol are added dropwise to a solution at 0° C. of 27.3 g (~722 mmol) of sodium borohydride in 270 mL of ethanol. For the addition, the temperature of the reaction mixture is maintained from 2 and 6° C., and then at 0° C. for 1 hour and at room temperature for 20 hours. The reaction is worked up by addition of 200 mL of water, and a white precipitate forms. The reaction mixture is filtered off; the filtrate is evaporated under vacuum to give the product in the form of a yellow paste. The product is placed in 300 mL of diethyl ether and then filtered to give 23.2 g (68%) of (6-iodopyrid-3-yl)methanol in the form of a pale yellow solid.

e-Ethyl chloroethoxyacetate 40 mL (224 mmol) of ethyl diethoxyacetate, 38 mL (536 mmol) of acetyl chloride and 0.11 g (0.45 mmol) of iodine are placed in a round-bottomed flask and heated at 50° C. for 24 hours. The reaction progress is monitored by NMR. The excess acetyl chloride is removed by evaporation under vacuum. 36.3 g (100%) of ethyl chloroethoxyacetate are obtained in the form of a liquid colored brown by the residual iodine.

f-Ethyl (diethoxyphosphoryl)ethoxyacetate 36.3 g (218 mmol) of ethyl chloroethoxyacetate and 37.4 mL (218 mmol) of triethyl phosphite are placed in a round-bottomed flask and heated at 150° C. for 3 hours. The reaction progress is monitored by NMR. 59 g (100%) of ethyl (diethoxyphosphoryl)ethoxyacetate are obtained directly in the form of a colorless liquid.

g-6-Iodopyridine-3-carbaldehyde 86 g (987 mol) of manganese (II) oxide are added to a solution of 23.2 g (98.7 mmol) of (6-iodopyrid-3-yl)methanol in 800 mL of dichloromethane. The reaction mixture is stirred at room temperature for 22 hours. The reaction mixture is filtered through Celite and rinsed with dichloromethane. The filtrate is evaporated under vacuum to give 17 g (74%) of 6-iodopyridine-3-carbaldehyde in the form of a yellow solid.

h-tert-Butyl [3-(5-formylpyrid-2-yl)phenyl]methylcarbamate 11.2 g (33.6 mmol) of tert-butyl methyl[3-(4,4,5,5-tetramethyl[1.3.2]dioxaborolan-2-yl)phenyl]carbamate, 5.2 g (22.4 mmol) of 6-iodopyridine-3-carbaldehyde and 10.3 g (67.2 mmol) of caesium fluoride are dissolved in 400 mL of diethylene glycol dimethyl ether. After bubbling nitrogen through the reaction mixture for 15 minutes, 1.1 g (1.3 mmol) of dichloro[1,1'-bis(diphenylphosphino)ferrocene]palladium are added. The reaction mixture is heated at 80° C. for 4 hours with vigorous stirring. After cooling, the reaction is worked up by addition of 300 mL of water and extraction with ethyl acetate. The organic phases are combined, washed with saturated sodium chloride solution and then dried over sodium sulfate. The solvents are evaporated off. The crude product obtained is purified by chromatography on a column of silica eluted with a 75/25 heptane/ethyl acetate mixture to give 3.7 g (53%) of tert-butyl[3-(5-formylpyrid-2-yl)phenyl]methylcarbamate in the form of a yellow oil.

i-Ethyl 3-{6-[3-(tert-butoxycarbonylmethylamino)phenyl]pyrid-3-yl}-2-ethoxyacrylate 0.6 g (14.2 mmol) of sodium hydride is added portionwise to a solution at 0° C. of 3.8 g (14.2 mmol) of ethyl (diethoxyphosphoryl)ethoxyacetate in 40 mL of tetrahydrofuran. The reaction mixture is stirred for 1 hour at room temperature, followed by dropwise addition of 3.7 g (11.8 mmol) of tert-butyl[3-(5-formylpyrid-2-yl)phenyl]methylcarbamate diluted in 40 mL of tetrahydrofuran. The reaction is slightly exothermic and the reaction mixture is maintained at a temperature of 25-27° C. with an ice bath. When the temperature has stabilized, the reaction mixture is stirred for 18 hours at room temperature. The reaction is worked up by addition of 60 mL of water and extraction with ethyl acetate. The organic phases are combined, washed with saturated aqueous sodium chloride solution and then dried over magnesium sulfate. After filtration, the solvents are evaporated off. NMR analysis of the crude product obtained shows the presence of 70% of the expected (Z) isomer. The crude product obtained is purified by chromatography on a column of silica eluted with an 80/20 heptane/ethyl acetate mixture to give 300 mg of the pure (Z) isomer of ethyl 3-{6-[3-(tert-butoxycarbonylmethylamino)phenyl]pyrid-3-yl}-2-ethoxyacrylate and 4.0 g of the Z/E mixture in the form of colorless oils. Overall yield: 86% (Z/E 70/30).

j-Ethyl (Z)-2-ethoxy-3-[6-(3-methylaminophenyl)pyrid-3-yl]acrylate 0.62 mL (7.0 mmol) of trifluoroacetic acid is added to a solution of 0.30 g (0.7 mmol) of ethyl (Z)-3-{6-[3-(tert-butoxycarbonylmethylamino)phenyl]pyrid-3-yl}-2-ethoxyacrylate in 10 mL of dichloromethane. The reaction mixture is stirred at room temperature for 20 hours. The reaction is stopped by addition of 10 mL of water and extraction with dichloromethane. The organic phases are combined and then dried over magnesium sulfate. After filtration, the solvents are evaporated off. The crude product obtained is purified by chromatography on a column of silica eluted with an 80/20 heptane/ethyl acetate mixture to give 0.19 g (86%) of ethyl (Z)-2-ethoxy-3-[6-(3-methylaminophenyl)pyrid-3-yl]acrylate in the form of a yellow solid.

k-Ethyl (Z)-2-ethoxy-3-(6-{3-[methyl-(4-nitrophenoxycarbonyl)amino]phenyl}pyrid-3-yl)acrylate 0.17 g (0.83 mmol) of 4-nitrophenyl chloroformate and then 0.14 mL (0.83 mmol) of diisopropylethylamine are added to a solution of 0.18 g (0.55 mmol) of ethyl (Z)-2-ethoxy-3-[6-(3-methylaminophenyl)pyrid-3-yl]acrylate in 5 mL of dichloromethane. The reaction mixture is stirred for 1 hour 30 minutes at room temperature. The reaction is stopped by addition of 5 mL of water and extraction with dichloromethane. The organic phases are combined and then dried over magnesium sulfate. The solvents are evaporated off. 0.32 g (100%) of ethyl (Z)-2-ethoxy-3-(6-{3-[methyl-(4-nitrophenoxycarbonyl)amino]phenyl}pyrid-3-yl)acrylate is obtained in the form of a yellow oil. The crude product obtained is used directly in the following step.

l-Ethyl (Z)-2-ethoxy-3-{6-[3-(3-heptyl-1-methylureido)phenyl]pyrid-3-yl}acrylate 0.16 mL (1.1 mmol) of n-heptylamine is added to a solution of 0.32 g (0.55 mmol) of ethyl (Z)-2-ethoxy-3-(6-{3-[methyl-(4-nitrophenoxycarbonyl)amino]phenyl}pyrid-3-yl)acrylate in 10 mL of dimethylformamide. The tube is sealed and rapidly placed in an oil bath preheated to 80° C. The reaction mixture is stirred at 80° C. for 1 hour 30 minutes. After cooling, the reaction is worked up by addition of 10 mL of water and extraction with ethyl acetate. The organic phases are combined, washed with saturated sodium chloride solution and then dried over magnesium sulfate. The solvents are evaporated off. The crude product obtained is purified by chromatography on a column of silica eluted with a 70/30 heptane/ethyl acetate mixture to give 0.14 g (54%) of ethyl (Z)-2-ethoxy-3-{6-[3-(3-heptyl-1-methylureido)phenyl]pyrid-3-yl}acrylate in the form of a colorless oil.

m-(Z)-2-ethoxy-3-{6-[3-(3-heptyl-1-methylureido)phenyl]pyrid-3-yl}acrylic acid 0.4 mL (0.45 mmol) of aqueous 1 M lithium hydroxide solution is added to a solution of 0.14 g (0.3 mmol) of ethyl (Z)-2-ethoxy-3-{6-[3-(3-heptyl-1-methylureido)phenyl]pyrid-3-yl}acrylate in 6 mL of tetrahydrofuran. The reaction mixture is stirred at 68° C. for 24 hours. After cooling, the reaction is worked up by addition of 0.45 mL (0.45 mmol) of aqueous 1 M acetic acid solution and 10 mL of water and extraction with ethyl acetate. The organic phases are combined, washed with saturated sodium chloride solution and then dried over magnesium sulfate. The solvents are evaporated off. The crude product obtained is purified by chromatography on a column of silica eluted with a 90/10 dichloromethane/methanol mixture to give 60 mg (46%) of (Z)-2-ethoxy-3-{6-[3-(3-heptyl-1-methylureido)phenyl]pyrid-3-yl}acrylic acid in the form of a yellow oil.

n-(Z)-2-ethoxy-3-{6-[3-(3-heptyl-1-methylureido)phenyl]pyrid-3-yl}acrylic acid hydrochloride 0.3 mL (0.3 mmol) of a 1 N ethanolic hydrogen chloride solution is added to a solution of 0.12 g (0.3 mmol) of (Z)-2-ethoxy-3-{6-[3-(3-heptyl-1-methylureido)phenyl]pyrid-3-yl}acrylic acid in 1 mL of ethanol, precooled to 0° C. The ethanol is evaporated off under a flow of nitrogen and 6 mL of diethyl ether are added. The hydrochloride precipitates; the reaction medium is filtered off and the solid obtained is rinsed thoroughly with diethyl ether. The solid obtained is recrystallized from a hot mixture of acetone and a minimum amount of water. 100 mg (77%) of (Z)-2-ethoxy-3-{6-[3-(3-heptyl-1-methylureido)phenyl]pyrid-3-yl}acrylic acid hydrochloride are obtained in the form of a yellow solid with a melting point of 170° C.

$^1$H NMR (CDCl$_3$, 400 MHz): 0.85 (t, J=6.8-Hz, 3H); 1.26 (m, 8H); 1.45 (t, J=7.1-Hz, 3H); 1.46 (m, 2H); 3.22 (t, J=7.2-Hz, 2H); 3.38 (s, 3H); 4.33 (q, J=7.1-Hz, 2H); 4.80 (m, 1H); 6.85 (s, 1H); 7.51 (d, J=8.1-Hz, 1H); 7.64 (t, J=8-Hz, 1H); 7.97-8.03 (m, 3H); 8.64 (d, J=8.1-Hz, 1H); 9.24 (s, 1H); 10.7 (s, 1H).

EXAMPLE 5

Synthesis of (E)-3-[3'-(3-heptyl-1-methylureido)biphenyl-4-yl]-2-methylacrylic acid

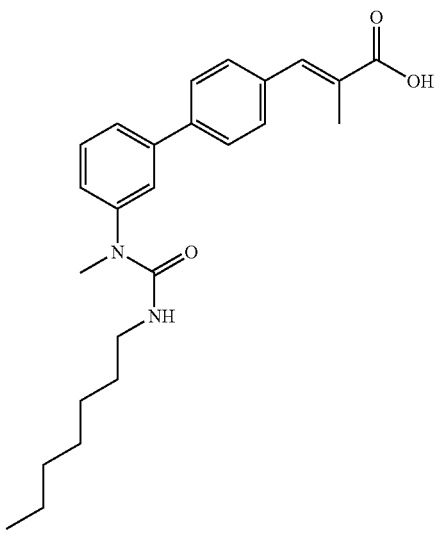 [SMILES: CCCCCCCNC(=O)N(C)c1cccc(-c2ccc(/C=C(\C)C(=O)O)cc2)c1]

a-(3-bromophenyl)methylamine 3.6 g (12.7 mmol) of tert-butyl 3-bromophenyl-N-methylcarbamate, prepared in a manner similar to that of Example 4b, are dissolved in 15 mL of dichloromethane. 5 mL of trifluoroacetic acid are added and the reaction mixture is stirred for 1 hour at room temperature. The reaction is worked up by addition of 50 mL of saturated sodium hydrogen carbonate solution and extraction with ethyl acetate. The organic phases are combined and dried over sodium sulfate. The solvents are evaporated off and the residue is then purified by chromatography on a column of silica eluted with a 50/50 heptane/ethyl acetate mixture. 2.14 g (90%) of (3-bromophenyl)methylamine are obtained in the form of an oil.

b-3'-Methylaminobiphenyl-4-carbaldehyde 5 g (26.8 mmol) of 3-bromophenylmethylamine and 4 g (26.8 mmol) of commercial 4-formylbenzeneboronic acid are dissolved in 50 mL of an aqueous 6/1 mixture of dimethylformamide/aqueous 2 M potassium phosphate. 1.5 g (1.3 mmol, 5 mol %) of tetrakis(triphenylphosphine)palladium are added. The mixture is stirred for 2 hours at 90° C. The reaction is worked up by addition of 50 mL of water and extraction with ethyl acetate. The organic phases are washed with sodium chloride solution and dried over magnesium sulfate. The solvents are evaporated off, and the residue is then purified by chromatography on a column of silica eluted with a 7/3 heptane/ethyl acetate mixture. 4.3 g (76%) of 3'-methylaminobiphenyl-4-carbaldehyde are obtained.

c-Ethyl (E)-2-methyl-3-(3'-methylaminobiphenyl-4-yl)acrylate

At 0° C., a solution of 1.6 mL (9.5 mmol) of triethyl phosphonopropionate in 5 mL of tetrahydrofuran is added to a suspension of 379 mg (9.5 mmol) of sodium hydride in 5 mL of tetrahydrofuran. The mixture is stirred for 15 minutes at 0° C. and a solution of 800 mg (3.8 mmol) of 3'-methylaminobiphenyl-4-carbaldehyde in 5 mL of tetrahydrofuran is then added. The reaction mixture is stirred for 12 hours at room temperature. The reaction is worked up by addition of 50 mL of saturated ammonium chloride solution and extraction with ethyl acetate. The organic phases are washed with sodium chloride solution and dried over magnesium sulfate. The solvents are evaporated off, and the residue is then purified by chromatography on a column of silica eluted with a 7/3 heptane/ethyl acetate mixture. 750 mg (67%) of ethyl 2-methyl-3-(3'-methylaminobiphenyl-4-yl)acrylate, (E) isomer, are obtained.

d-Ethyl (E)-[3'-(3-heptyl-1-methylureido)biphenyl-4-yl]-2-methylacrylate

618 µL (3.8 mmol) of heptyl isocyanate are added to a solution of 750 mg (2.5 mmol) of ethyl 2-methyl-3-(3'-methylaminobiphenyl-4-yl)acrylate in 10 mL of dichloromethane in the presence of 2 mL of triethylamine. The reaction mixture is stirred for 12 hours at 50° C. The reaction is stopped by addition of 50 mL of water and extraction with ethyl acetate. The organic phases are washed with sodium chloride solution and dried over magnesium sulfate. The solvents are evaporated off, and the residue is then purified by chromatography on a column of silica eluted with a 7/3 heptane/ethyl acetate mixture. 860 mg (78%) of ethyl (E)-3-[3'-(3-heptyl-1-methylureido)biphenyl-4-yl]-2-methylacrylate are obtained.

e-(E)-3-[3'-(3-heptyl-1-methylureido)biphenyl-4-yl]-2-methylacrylic acid 400 mg of sodium hydroxide are added to a solution of 860 mg (2 mmol) of ethyl (E)-3-[3'-(3-heptyl-1-methylureido) biphenyl-4-yl]-2-methylacrylate in 15 mL of tetrahydrofuran in the presence of 5 mL of methanol. The reaction mixture is stirred for 12 hours at room temperature. The reaction is worked up by addition of 20 mL of water and 1 mL of acetic acid and extraction with ethyl acetate. The organic phases are washed with sodium chloride solution and dried over magnesium sulfate. The solvents are evaporated off, and the residue is then purified by chromatography on a column of silica eluted with a 7/3 heptane/ethyl acetate mixture. The oil obtained is crystallized from pentane, 550 mg (69%) of solid (E)-3-[3'-(3-heptyl-1-methylureido)biphenyl-4-yl]-2-methylacrylic acid are obtained.

$^1$H NMR (CDCl$_3$, 400 MHz): 0.85 (t, J=7.2-Hz, 3H); 1.12-1.23 (m, 8H); 1.42 (m, 2H); 2.20 (s, 3H); 3.18 (m, 2H), 3.27 (s, 3H); 4.39 (t, J=5.4-Hz, 1H); 7.24 (m, 1H); 7.49-7.65 (m, 7H); 7.85 (s, 1H).

EXAMPLE 6

Synthesis of (Z)-2-fluoro-3-[3'-(3-heptyl-1-methylureido)biphenyl-4-yl]acrylic acid

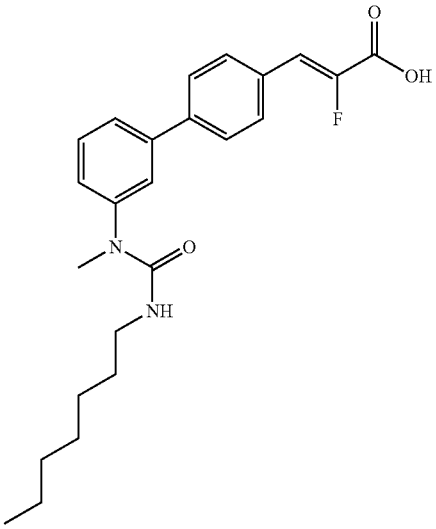

a-Ethyl 2-fluoro-3-(3'-methylaminobiphenyl-4-yl)acrylate 382 mg (9.5 mmol) of sodium hydride are added to a solution of 1.9 mL (9.5 mmol) of commercial triethyl 2-fluoro-2-phosphonoacetate in 10 mL of tetrahydrofuran. The reaction mixture is stirred at room temperature for 40 minutes. A solution of 803 mg of 3'-methylaminobiphenyl-4-carbaldehyde prepared as described in Example 5b (3.8 mmol) in 8 mL of tetrahydrofuran is then added dropwise. The reaction mixture is stirred at room temperature overnight. The reaction medium is poured into saturated ammonium chloride solution and extracted with ethyl acetate. The organic phases are combined, washed with water and dried over sodium sulfate. The solvent is evaporated off and the residue (2.2 g) is purified by chromatography on a column of silica eluted with an 85/15 heptane/ethyl acetate mixture. 936 mg (82%) of ethyl 2-fluoro-3-(3'-methylaminobiphenyl-4-yl)acrylate are obtained in the form of a yellow oil.

b-Ethyl 2-fluoro-3-[3'-(3-heptyl-1-methylureido)biphenyl-4-yl]acrylate

740 µL (4.6 mmol) of heptyl isocyanate are added to a solution of 915 mg (3.1 mmol) of ethyl 2-fluoro-3-(3'-methylaminobiphenyl-4-yl)acrylate in 10 mL of dichloromethane/triethylamine (4/1). The reaction mixture is heated at 50° C. for 24 hours. The reaction medium is evaporated and the residue (1.7 g) is then purified by chromatography on a column of silica eluted with an 80/20 heptane/ethyl acetate mixture.

1.4 g (100%) of ethyl 2-fluoro-3-[3'-(3-heptyl-1-methylureido)biphenyl-4-yl]acrylate are obtained in the form of a paste.

c-(Z)-2-Fluoro-3-[3'-(3-heptyl-1-methylureido)biphenyl-4-yl]acrylic acid 860 mg (21.5 mmol) of sodium hydroxide are added to a solution of 948 mg (2.15 mmol) of ethyl 2-fluoro-3-[3'-(3-heptyl-1-methylureido)biphenyl-4-yl]acrylate in 25 mL of ethanol and 2.5 mL of tetrahydrofuran. The reaction mixture is heated at 50° C. overnight. The reaction medium is evaporated to dryness, taken up in water, acidified with aqueous 1 N hydrochloric acid solution and extracted with ethyl acetate. The organic phases are combined, washed with water and dried over sodium sulfate. The solvent is evaporated off and the orange oil obtained (1.1 g) is purified by chromatography on a column of silica eluted with a 95/5 dichloromethane/methanol mixture and then on another column of silica eluted with a 50/50/1 heptane/ethyl acetate/acetic acid mixture.

122 mg (14%) of (Z)-2-fluoro-3-[3'-(3-heptyl-1-methylureido)biphenyl-4-yl]acrylic acid are obtained in the form of white crystals (m.p.=142-144° C.) and 176 mg (20%) of (E)-2-fluoro-3-[3'-(3-heptyl-1-methylureido)biphenyl-4-yl] acrylic acid are obtained in the form of white crystals with a melting point of 118-120° C.

$^1$H NMR (CDCl$_3$, 400 MHz): 0.85 (t, 3H); 1.23 (m, 8H); 1.40 (m, 2H); 3.02 (q, 2H); 3.20 (s, 3H); 6.10 (t, 1H); 7.13 (d, J=24-Hz, 1H); 7.25 (d, 1H); 7.48 (t, 1H); 7.55 (d, 2H); 7.79 (s, 4H).

EXAMPLE 7

Synthesis of 2-[1-[3'-(3-heptyl-1-methylureido)biphenyl-4-yl]meth-(E)-ylidene]butyric acid

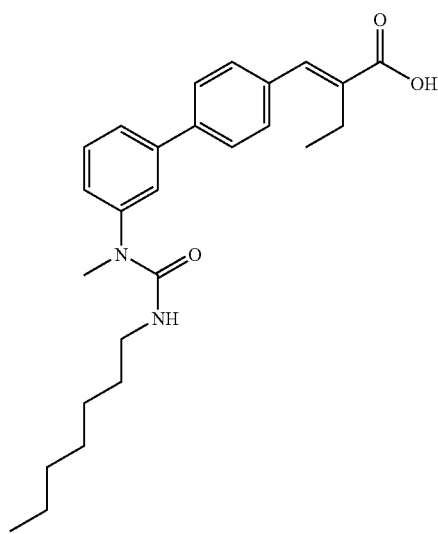 [SMILES: CCCCCCCNC(=O)N(C)c1cccc(-c2ccc(/C=C(\CC)C(=O)O)cc2)c1]

a-Ethyl 2-[1-(3'-methylaminobiphenyl-4-yl)meth-(E)-ylidene]butyrate 197 mg (4.9 mmol) of sodium hydride are added to a mixture of 1.2 mL (4.9 mmol) of triethyl 2-phosphonobutyrate and 415 mg of 3'-methylaminobiphenyl-4-carbaldehyde (2.0 mmol) in 10 mL of tetrahydrofuran. The reaction mixture is stirred at room temperature overnight, poured into saturated aqueous ammonium chloride solution and extracted with ethyl acetate. The organic phases are combined, washed with water and dried over sodium sulfate. The solvent is evaporated off and the residue (1.1 g) is purified by chromatography on a column of silica eluted with a 90/10 heptane/ethyl acetate mixture. 438 mg (72%) of ethyl 2-[1-(3'-methylaminobiphenyl-4-yl)meth-(E)-ylidene]butyrate are obtained in the form of off-white crystals.

b-Ethyl 2-[1-[3'-(3-heptyl-1-methylureido)biphenyl-4-yl]meth-(E)-ylidene]butyrate 172 µL (1 mmol) of heptyl isocyanate are added to 214 mg (0.7 mmol) of ethyl 2-[1-(3'-methylaminobiphenyl-4-yl) meth-(E)-ylidene]butyrate. The reaction mixture is heated at 100° C. in an Emrys Optimizer microwave oven for 20 minutes. The residue is purified by chromatography on a column of silica eluted with a 70/30 heptane/ethyl acetate mixture. 306 mg (98%) of ethyl 2-[1-[3'-(3-heptyl-1-methylureido) biphenyl-4-yl]meth-(E)-ylidene]butyrate are obtained in the form of yellowish crystals.

c-2-[1-[3'-(3-heptyl-1-methylureido)biphenyl-4-yl]meth-(E)-ylidene]butyric acid 261 mg (6.5 mmol) of sodium hydroxide are added to a solution of 294 mg (0.65 mmol) of ethyl 2-[1-[3'-(3-heptyl-1-methylureido)biphenyl-4-yl]meth-(E)-ylidene]butyrate in 10 mL of ethanol. The reaction mixture is heated at 50° C. for 15 hours. The reaction medium is evaporated to dryness, taken up in water, acidified with aqueous 2N hydrochloric acid solution and extracted with ethyl acetate. The organic phases are combined, washed with water and dried over magnesium sulfate. The solvent is evaporated off and the solid obtained is taken up in a mixture of ethyl ether and heptane, filtered off and dried.

242 mg (88%) of 2-[1-[3'-(3-heptyl-1-methylureido)biphenyl-4-yl]meth-(E)-ylidene]butyric acid are obtained in the form of a cream-colored powder with a melting point of 102-104° C.

$^1$H NMR (DMSO-d6, 400 MHz): 0.74 (t, 3H); 1.04 (t, 3H); 1.13 (m, 8H); 1.29 (m, 2H); 2.92 (q, 2H); 3.10 (s, 3H); 6.00 (t, 1H); 7.15 (d, 1H); 7.37 (t, 1H); 7.41-7.48 (m, 5H); 7.65 (d, 2H); 12.5 (1H).

EXAMPLE 8

Synthesis of 2-[1-[3'-(1-methyl-3-pentylureido)biphenyl-4-yl]meth-(E)-ylidene]pentanoic acid

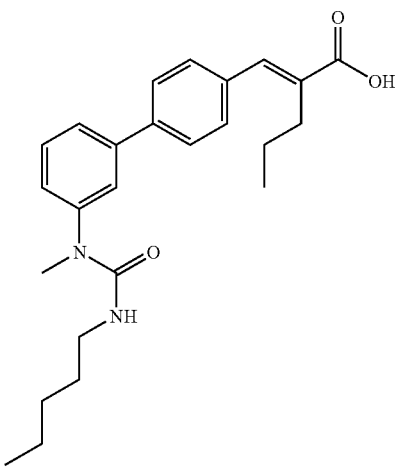 [SMILES: CCCCCNC(=O)N(C)c1cccc(-c2ccc(/C=C(\CCC)C(=O)O)cc2)c1]

a-Ethyl 2-[1-(3'-methylaminobiphenyl-4-yl)meth-(E)-ylidene]pentanoate 197 mg (4.9 mmol) of sodium hydride are added to a mixture of 1.2 mL (4.9 mmol) of triethyl 2-phosphonopentanoate and 415 mg of 3'-methylaminobiphenyl-4-carbaldehyde prepared as described in Example 9b (2.0 mmol) in 10 mL of tetrahydrofuran. The reaction mixture is stirred at room temperature overnight. The reaction medium is poured into saturated ammonium chloride solution and extracted with ethyl acetate. The organic phases are combined, washed with water and dried over sodium sulfate. The solvent is evaporated off and the residue (1 g) is purified by chromatography on a column of silica eluted with a 90/10 heptane/ethyl acetate mixture. 511 mg (81%) of ethyl 2-[1-(3'-methylaminobiphenyl-4-yl)meth-(E)-ylidene]pentanoate are obtained in the form of a yellow oil.

b-Ethyl 2-[1-[3'-(1-methyl-3-pentylureido)biphenyl-4-yl]meth-(E)-ylidene]pentanoate 154 µL (1 mmol) of pentyl isocyanate are added to 253 mg (0.8 mmol) of ethyl 2-[1-(3'-methylaminobiphenyl-4-yl)meth-(E)-ylidene]pentanoate. The reaction mixture is heated at 100° C. in an Emrys Optimizer microwave oven for 20 minutes. The residue is purified by chromatography on a column of silica eluted with a 70/30 heptane/ethyl acetate mixture.

361 mg (59%) of ethyl 2-[1-[3'-(1-methyl-3-pentylureido)biphenyl-4-yl]meth-(E)-ylidene]pentanoate are obtained in the form of a yellowish oil.

c-2-[1-[3'-(1-Methyl-3-pentylureido)biphenyl-4-yl]meth-(E)-ylidene]pentanoic acid 176 mg (4.4 mmol) of sodium hydroxide are added to a solution of 192 mg (0.44 mmol) of ethyl 2-[1-[3'-(1-methyl-3-pentylureido)biphenyl-4-yl]meth-(E)-ylidene]pentanoate in 8 mL of ethanol. The reaction mixture is heated at 50° C. for 15 hours. The reaction medium is evaporated to dryness, taken up in water, acidified with 2 N hydrochloric acid solution and extracted with ethyl acetate. The organic phases are combined, washed with water and dried over magnesium sulfate. The solvent is evaporated off and the solid obtained is purified by chromatography on a column of silica eluted with a 50/50 heptane/ethyl acetate mixture. The solvents are evaporated off and the oil obtained is crystallized from ethyl ether, filtered and dried. 133 mg (74%) of 2-[1-[3'-(1-methyl-3-pentylureido)biphenyl-4-yl]meth-(E)-ylidene]pentanoic acid are obtained in the form of a white powder with a melting point of 118-119° C.

$^1$H NMR (CDCl$_3$, 400 MHz): 0.85 (t, 3H); 1.02 (t, 3H); 1.21-1.41 (m, 4H); 1.43 (m, 2H); 1.64 (m, 2H); 2.55-2.59 (m, 2H); 3.18 (q, 2H); 3.33 (s, 3H); 4.40 (t, 1H); 7.24 (d, 1H); 7.50 (m, 4H); 7.56 (t, 1H); 7.63 (d, 2H); 7.83 (s, 1H).

EXAMPLE 9

Synthesis of 2-[1-[3'-(1-methyl-3-pentylureido)biphenyl-4-yl]meth-(E)-ylidene]butyric acid

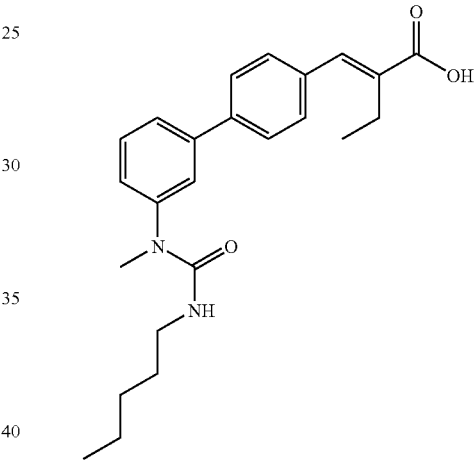

a-Ethyl 2-[1-[3'-(3-pentyl-1-methylureido)biphenyl-4-yl]meth-(E)-ylidene]butyrate 136 µL (1.0 mmol) of pentyl isocyanate are added to 213 mg (0.7 mmol) of ethyl 2-[1-(3'-methylaminobiphenyl-4-yl)meth-(E)-ylidene]butyrate. The reaction mixture is heated at 100° C. in an Emrys Optimizer microwave oven for 20 minutes. The residue is purified by chromatography on a column of silica eluted with a 70/30 heptane/ethyl acetate mixture. 291 mg (100%) of ethyl 2-[1-[3'-(3-pentyl-1-methylureido)biphenyl-4-yl]meth-(E)-ylidene]butyrate are obtained in the form of a yellowish oil.

b-2-[1-[3'-(1-methyl-3-pentylureido)biphenyl-4-yl]meth-(E)-ylidene]butyric acid 268 mg (6.7 mmol) of sodium hydroxide are added to a solution of 284 mg (0.67 mmol) of ethyl 2-[1-[3'-(1-methyl-3-pentylureido)biphenyl-4-yl]meth-(E)-ylidene]butyrate in 10 mL of ethanol. The reaction mixture is heated at 50° C. for 15 hours. The reaction medium is evaporated to dryness, taken up in water, acidified with 2 N hydrochloric acid solution and extracted with ethyl acetate. The organic phases are combined, washed with water and dried over magnesium sulfate. After filtration, the solvent is evaporated off and the solid obtained is taken up in ethyl ether, filtered off and dried. 222 mg (84%) of 2-[1-[3'-(1-methyl-3-pentylureido)biphenyl-4-yl]meth-(E)-ylidene]butyric acid are obtained in the form of a white powder with a melting point of 150-152° C.

¹H NMR (DMSO-d6, 400 MHz): 0.61 (t, 3H); 0.90 (t, 3H); 0.94-1.04 (m, 4H); 1.16 (m, 2H); 2.78 (q, 2H); 2.97 (s, 3H); 5.89 (t, 1H); 7.01 (d, 1H); 7.23 (t, 1H); 7.28-7.34 (m, 5H); 7.51 (d, 2H); 12.3 (1H).

EXAMPLE 10

Synthesis of (Z)-2-ethoxy-3-[3'-(1-methyl-3-phenethylureido)biphenyl-4-yl]acrylic acid

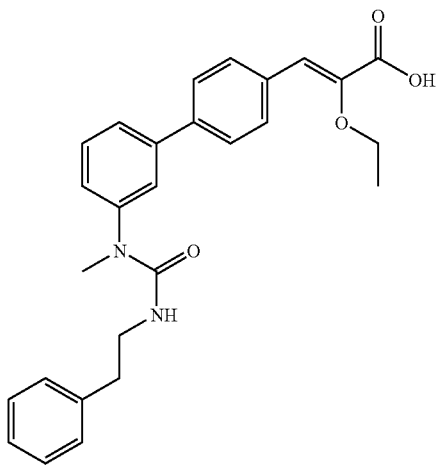 [SMILES: CCO/C(=C\c1ccc(-c2cccc(N(C)C(=O)NCCc3ccccc3)c2)cc1)C(=O)O]

a-Methyl[3-(4,4,5,5-tetramethyl[1.3.2]dioxaborolan-2-yl)phenyl]amine

To a solution of 10.9 g (59 mmol) of (3-bromophenyl)methylamine and 15 g (59 mmol) of bis-pinacoldiborane in 110 mL of dimethylformamide are added 17.4 g (177 mmol) of potassium acetate and 2.4 g (3 mmol) of dichloro[111'-bis(diphenylphosphino)ferrocene]palladium. The reaction medium is heated at 85° C. for 3 hours, cooled and extracted with dichloromethane. The organic phase is washed with water, dried over magnesium sulfate, filtered and evaporated. The residue obtained is purified by chromatography on a column of silica eluted with an 80/20 heptane/ethyl acetate mixture. 12.7 g (92%) of methyl[3-(4,4,5,5-tetramethyl[1.3.2]dioxaborolan-2-yl)phenyl]amine are obtained.

b-Ethyl (Z)-2-ethoxy-3-(3'-methylaminobiphenyl-4-yl)acrylate

To a solution of 10.8 g (36.1 mmol) of ethyl (Z)-3-(4-bromophenyl)-2-ethoxyacrylate, 108 mL (217 mmol) in 120 mL of toluene, aqueous 2 M sodium carbonate solution and 1.5 g (1.8 mmol) of dichloro[11'-bis(diphenylphosphino)ferrocene]palladium are added. The reaction medium is stirred and 9.25 g (39.7 mmol) of methyl[3-(4,4,5,5-tetramethyl[1.3.2]dioxaborolan-2-yl)phenyl]amine are then added. After stirring at 80° C. for 2 hours, the reaction medium is hydrolyzed and diluted with ethyl acetate. After separation of the phases by settling, the ethyl acetate phase is washed with saturated sodium chloride solution, dried over magnesium sulfate, filtered and evaporated. The residue obtained is purified by chromatography on a column of silica eluted with a 90/10 and then 80/20 heptane/ethyl acetate mixture. 10.5 g (94%) of ethyl (Z)-2-ethoxy-3-(3'-methylaminobiphenyl-4-yl)acrylate are obtained in the form of a yellow oil. After taking up the product in pentane, 9.5 g (85%) of ethyl (Z)-2-ethoxy-3-(3'-methylaminobiphenyl-4-yl)acrylate are obtained in the form of a pale yellow solid with a melting point of 52° C.

c-Ethyl (Z)-2-ethoxy-3-{3'-[methyl-(4-nitrophenoxycarbonyl)amino]biphenyl-4-yl}acrylate To a solution of 4 g (12.3 mmol) of ethyl (Z)-2-ethoxy-3-(3'-methylaminobiphenyl-4-yl)acrylate in 80 mL of dichloromethane, cooled to 0° C., 3 g (14.7 mmol) of 4-nitrophenyl chloroformate and then 2.6 mL (14.7 mmol) of diisopropylethylamine are successively added dropwise. The reaction medium is then stirred at room temperature for 2 hours. After addition of water, the medium is extracted with dichloromethane. The organic phase is washed with water, dried over magnesium sulfate, filtered and evaporated. 7 g (100%) of crude residue are obtained and used without further purification in the following step.

d-Ethyl (Z)-2-ethoxy-3-[3'-(1-methyl-3-phenethylureido)biphenyl-4-yl]acrylate

A solution of 1.75 g (3 mmol) of ethyl (Z)-2-ethoxy-3-{3'-[methyl-(4-nitrophenoxycarbonyl)amino]biphenyl-4-yl}acrylate, 0.46 mL (3.7 mmol) of phenethylamine, in 20 mL of dimethylformamide is heated at 80° C. for 2 hours. After addition of water, the reaction medium is extracted with ethyl acetate, washed with water, dried over magnesium sulfate, filtered and evaporated. The residue obtained is purified by chromatography on a column of silica eluted with a 70/30 heptane/ethyl acetate mixture. 0.7 g (50%) of ethyl (Z)-2-ethoxy-3-[3'-(1-methyl-3-phenethylureido)biphenyl-4-yl]acrylate is obtained.

e-(Z)-2-ethoxy-3-[3'-(1-methyl-3-phenethylureido)biphenyl-4-yl]acrylic acid

In a manner similar to that of Example 1h, starting with 0.7 g (1.64 mmol) of ethyl (Z)-2-ethoxy-3-[3'-(1-methyl-3-phenethylureido)biphenyl-4-yl]acrylate, 0.6 g (83%) of (Z)-2-ethoxy-3-[3'-(1-methyl-3-phenethylureido)biphenyl-4-yl]acrylic acid is obtained in the form of a pale yellow solid with a melting point of 70° C.

¹H NMR (CDCl₃, 400 MHz): 1.42 (t, J=7-Hz, 3H); 2.77 (t, J=6.7-Hz, 2H); 3.32 (s, 3H); 3.45 (m, 2H); 4.12 (q, J=7-Hz, 2H); 4.41 (t, J=5.7-Hz, 1H); 7.07-7.19 (m, 6H); 7.41-7.45 (m, 2H); 7.52 (m, 1H); 7.54 (d, J=8.3-Hz, 2H); 7.90 (d, J=8.3-Hz, 2H).

EXAMPLE 11

Synthesis of (Z)-3-[3'-(3-butyl-1-methylureido)biphenyl-4-yl]-2-methoxyacrylic acid

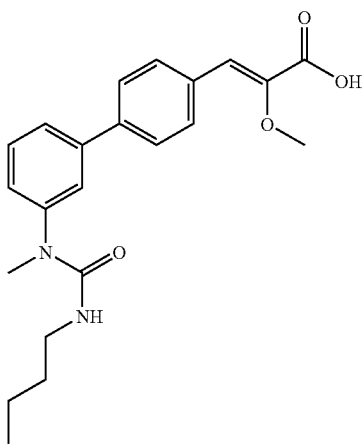 [SMILES: CCCCNC(=O)N(C)c1cccc(-c2ccc(/C=C(\OC)C(=O)O)cc2)c1]

a-Methyl chloromethoxyacetate 25 g (186 mmol) of methyl dimethoxyacetate, 26.5 mL (373 mmol) of acetyl chloride and 95 mg (0.4 mmol) of iodine are placed in a round-bottomed flask and heated at 50° C. for 18 hours. The reaction progress is monitored by NMR. The excess acetyl chloride is removed by evaporation under vacuum. 26 g (100%) of methyl chloromethoxyacetate are obtained in the form of a liquid colored brown by the residual iodine.

b-Methyl (diethoxyphosphoryl)methoxyacetate:

26 g (186 mmol) of methyl chloromethoxyacetate and 32 mL (186 mmol) of triethyl phosphite are placed in a round-bottomed flask and heated at 150° C. for 3 hours. The reaction progress is monitored by NMR. The reaction medium is concentrated under vacuum. 45 g (100%) of methyl (diethoxyphosphoryl)methoxyacetate are obtained directly in the form of a colorless liquid.

c-Methyl (Z)-3-(4-bromophenyl)-2-methoxyacrylate 3.3 g (83 mmol) of sodium hydride are added portionwise to a solution at 0° C. of 20 g (83 mmol) of methyl (diethoxyphosphoryl)methoxyacetate in 200 mL of tetrahydrofuran. The reaction mixture is stirred for 45 minutes at room temperature, followed by dropwise addition of 12.8 g (69 mmol) of 4-bromobenzaldehyde in 130 mL of tetrahydrofuran. The reaction is slightly exothermic and the reaction mixture is maintained at a temperature of 25-27° C. with an ice-water bath. When the temperature has stabilized, the reaction mixture is stirred for 20 hours at room temperature.

The reaction medium is hydrolyzed and then extracted with ethyl acetate. The organic phases are combined, washed with saturated sodium chloride solution and then dried over magnesium sulfate. The solvents are evaporated off.

NMR analysis of the crude product obtained shows the presence of 70% of the expected (Z) isomer.

The crude product obtained is purified by chromatography on a column of silica eluted with a 98/2 heptane/ethyl acetate mixture to give 4 g of the pure (E) isomer of methyl 3-(4-bromophenyl)-2-methoxyacrylate and 7.1 g of the pure (Z) isomer of methyl 3-(4-bromophenyl)-2-methoxyacrylate.

d-Methyl (Z)-2-methoxy-3-(3'-methylaminobiphenyl-4-yl)acrylate

In a manner similar to that of Example 10b, starting with 7.1 g (26 mmol) of methyl (Z)-3-(4-bromophenyl)-2-methoxyacrylate and 6.7 g (29 mmol) of methyl[3-(4,4,5,5-tetramethyl[1.3.2]dioxaborolan-2-yl)phenyl]amine, 7.8 g (80%) of methyl (Z)-2-methoxy-3-(3'-methylaminobiphenyl-4-yl)acrylate are obtained in the form of a pale yellow solid.

e-Methyl (Z)-2-methoxy-3-{3'-[methyl-(4-nitrophenoxycarbonyl)amino]biphenyl-4-yl}acrylate 3.9 g (19.4 mmol) of 4-nitrophenyl chloroformate and then 3.4 mL (19.4 mmol) of diisopropylethylamine are added to a solution of 4.8 g (16.1 mmol) of methyl (Z)-2-methoxy-3-(3'-methylaminobiphenyl-4-yl)acrylate. The reaction medium is stirred at room temperature for 2 hours. The reaction medium is hydrolyzed and then extracted with dichloromethane. The organic phase is washed with water, dried over magnesium sulfate, filtered and evaporated. 7.4 g (100%) of methyl (Z)-2-methoxy-3-{3'-[methyl-(4-nitrophenoxycarbonyl)amino]biphenyl-4-yl}acrylate are obtained in the form of a tacky foam.

f-Methyl (Z)-3-[3'-(3-butyl-1-methylureido)biphenyl-4-yl]-2-methoxyacrylate

In a manner similar to that of Example 10d, starting with 1.7 g (3.2 mmol) of methyl (Z)-2-methoxy-3-{3'-[methyl-(4-nitrophenoxycarbonyl)amino]biphenyl-4-yl}acrylate and 0.4 mL (3.9 mL) of n-butylamine, 0.8 g (64%) of methyl (Z)-3-[3'-(3-butyl-1-methylureido)biphenyl-4-yl]-2-methoxyacrylate is obtained in the form of a white solid with a melting point of 89° C.

g-(Z)-3-[3'-(3-butyl-1-methylureido)biphenyl-4-yl]-2-methoxyacrylic acid 2.7 mL (2.7 mmol) of aqueous 1 N sodium hydroxide solution are added to a solution of 0.7 g (1.8 mmol) of methyl (Z)-3-[3'-(3-butyl-1-methylureido)biphenyl-4-yl]-2-methoxyacrylate in 12 mL of tetrahydrofuran. The reaction medium is heated at 68° C. and stirred for 2 hours. The reaction medium is acidified with 2.8 mL of 1 N acetic acid solution and extracted with ethyl acetate. The organic phase is washed with water, dried over magnesium sulfate, filtered and evaporated. The residue obtained is recrystallized from hot ethyl acetate. 530 mg (77%) of (Z)-3-[3'-(3-butyl-1-methylureido)biphenyl-4-yl]-2-methoxyacrylic acid are obtained in the form of a white solid with a melting point of 146° C.

$^1$H NMR (CDCl$_3$, 400 MHz): 0.88 (t, J=7.3-Hz, 3H); 1.27 (m, 2H); 1.42 (m, 2H); 3.20 (td, J=7.0-Hz, J=5.7-Hz, 2H); 3.34 (s, 3H); 3.87 (s, 3H); 4.42 (t, J=5.7-Hz, 1H); 7.18 (s, 1H); 7.25 (m, 1H); 7.49-7.58 (m, 3H); 7.62 (d, J=8.4-Hz, 2H); 7.88 (d, J=8.4-Hz, 2H); 10.70 (s, 1H).

EXAMPLE 12

Synthesis of Methyl (Z)-3-[3'-(3-butyl-1-methylureido)biphenyl-4-yl]-2-methoxyacrylate

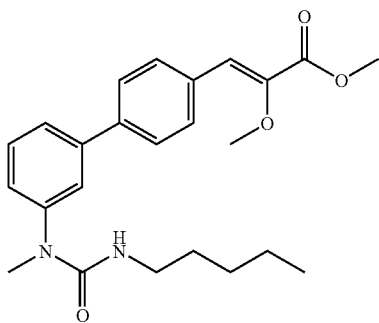 [SMILES: CCCCCNC(=O)N(C)c1cccc(-c2ccc(/C=C(\OC)C(=O)OC)cc2)c1]

a-Methyl (Z)-2-methoxy-3-[3'-(1-methyl-3-pentylureido)biphenyl-4-yl]acrylate

In a manner similar to that of Example 10d, starting with 1.7 g (3.2 mmol) of methyl (Z)-2-methoxy-3-{3'-[methyl-(4-nitrophenoxycarbonyl)amino]biphenyl-4-yl}acrylate and 0.45 mL (3.9 mL) of n-pentylamine, 0.9 g (67%) of methyl (Z)-2-methoxy-3-[3'-(1-methyl-3-pentylureido)biphenyl-4-yl]acrylate are obtained in the form of a white solid with a melting point of 86° C.

$^1$H NMR (CDCl$_3$, 400 MHz): 0.85 (t, J=7-Hz, 3H); 1.25 (m, 2H); 1.40 (m, 2H); 3.18 (td, J=7-Hz, J=5.6-Hz, 2H); 3.31 (s, 3H); 3.82 (s, s, 3H); 3.87 (s, 3H); 4.38 (t, J=5.6-Hz, 1H); 7.02 (s, 1H); 7.25 (m, 1H); 7.49-7.60 (m, 5H); 7.84 (d, J=8.4-Hz, 2H).

EXAMPLE 13

Synthesis of (Z)-3-[3'-(3-butyl-1-methylureido)biphenyl-4-yl]-2-methoxyacrylic acid

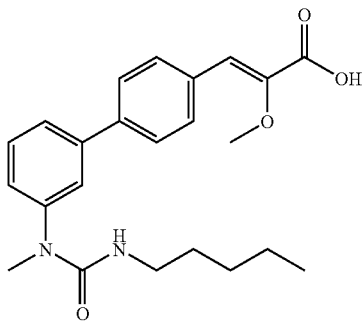 [SMILES: CCCCCNC(=O)N(C)c1cccc(-c2ccc(/C=C(\OC)C(=O)O)cc2)c1]

a-(Z)-2-Methoxy-3-[3'-(1-methyl-3-pentylureido)biphenyl-4-yl]acrylic acid 2.9 mL (2.9 mmol) of aqueous 1 N sodium hydroxide solution are added to a solution of 0.8 g (1.9 mmol) of methyl (Z)-2-methoxy-3-[3'-(1-methyl-3-pentylureido)biphenyl-4-yl]acrylate in 15 mL of tetrahydrofuran. The reaction medium is heated at 68° C. and stirred for 4 hours. The reaction medium is acidified with 3 mL of 1 N acetic acid solution and extracted with ethyl acetate. The organic phase is washed with water, dried over magnesium sulfate, filtered and evaporated. The residue obtained is recrystallized from hot ethyl acetate. 630 mg (82%) of (Z)-2-methoxy-3-[3'-(1-methyl-3-pentylureido)biphenyl-4-yl]acrylic acid are obtained in the form of a white solid with a melting point of 144° C.

$^1$H NMR (CDCl$_3$, 400 MHz): 0.85 (t, J=7-Hz, 3H); 1.20-1.29 (m, 4H); 1.43 (m, 2H); 3.18 (td, J=7-Hz, J=5.6-Hz, 2H); 3.33 (s, 3H); 3.87 (s, 3H); 4.42 (t, J=5.6-Hz, 1H); 7.18 (s, 1H); 7.25 (m, 1H); 7.49-7.58 (m, 3H); 6.62 (d, J=8.4-Hz, 2H); 7.87 (d, J=8.4-Hz, 2H); 10.70 (s, 1H).

EXAMPLE 14

Synthesis of Methyl (Z)-3-[3'-(3-cyclohexyl-1-methylureido)biphenyl-4-yl]-2-methoxyacrylate

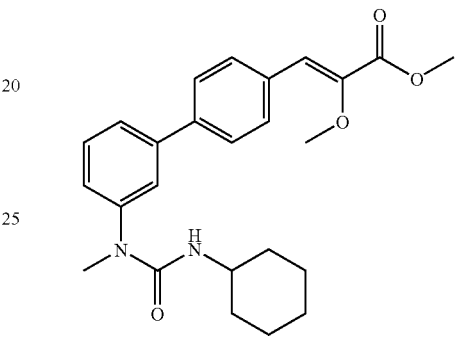

a-Methyl (Z)-3-[3'-(3-cyclohexyl-1-methylureido)biphenyl-4-yl]-2-methoxyacrylate In a manner similar to that of Example 10d, starting with 1.7 g (3.2 mmol) of methyl (Z)-2-methoxy-3-{3'-[methyl-(4-nitrophenoxycarbonyl)amino]biphenyl-4-yl}acrylate and 0.45 mL (3.9 mL) of cyclohexylamine, 0.7 g (51%) of methyl (Z)-3-[3'-(3-cyclohexyl-1-methylureido)biphenyl-4-yl]-2-methoxyacrylate are obtained in the form of a white solid with a melting point of 87° C.

$^1$H NMR (CDCl$_3$, 400 MHz): 0.95-1.09 (m, 3H); 1.24-1.38 (m, 2H); 1.54-1.63 (m, 3H); 1.89 (m, 2H); 3.31 (s, 3H); 3.67 (m, 1H); 3.83 (s, 3H); 3.87 (s, 3H); 4.28 (d, J=7.9-Hz, 1H); 7.02 (s, 1H); 7.24 (m, 1H); 7.46-7.56 (m, 3H); 7.60 (d, J=8.4-Hz, 2H); 7.88 (d, J=8.4-Hz, 2H).

EXAMPLE 15

Synthesis of (Z)-3-[3'-(3-cyclohexyl-1-methylureido)biphenyl-4-yl]-2-methoxyacrylic acid

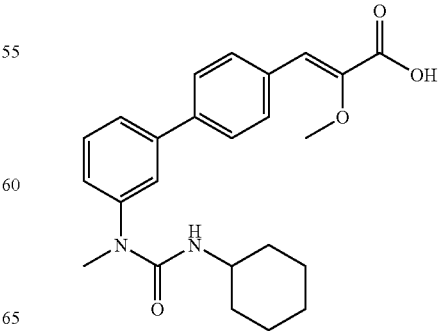

a-(Z)-3-[3'-(3-cyclohexyl-1-methylureido)biphenyl-4-yl]-2-methoxyacrylic acid 2.2 mL (2.2 mmol) of aqueous 1 N sodium hydroxide solution are added to a solution of 0.6 g (1.5 mmol) of methyl (Z)-3-[3'-(3-cyclohexyl-1-methylureido)biphenyl-4-yl]-2-methoxyacrylate in 12 mL of tetrahydrofuran. The reaction medium is heated at 68° C. and stirred for 4 hours. The reaction medium is acidified with 2.4 mL of 1 N acetic acid solution and extracted with ethyl acetate. The organic phase is washed with water, dried over magnesium sulfate, filtered and evaporated. The residue obtained is recrystallized from hot ethyl acetate. 500 mg (82%) of (Z)-3-[3'-(3-cyclohexyl-1-methylureido)biphenyl-4-yl]-2-methoxyacrylic acid are obtained in the form of a white solid with a melting point of 192° C.

$^1$H NMR (CDCl$_3$, 400 MHz): 0.95-1.09 (m, 3H); 1.24-1.38 (m, 2H); 1.54-1.63 (m, 3H); 1.89 (m, 2H); 3.32 (s, 3H); 3.67 (m, 1H); 3.87 (s, 3H); 4.29 (d, J=7.9-Hz, 1H); 7.18 (s, 1H); 7.24 (m, 1H); 7.48-7.56 (m, 3H); 7.61 (d, J=8.4-Hz, 2H); 7.88 (d, J=8.4-Hz, 2H); 10.70 (s, 1H).

EXAMPLE 16

Synthesis of (Z)-2-methoxy-3-[3'-(1-methyl-3-phenethylureido)biphenyl-4-yl]acrylic acid

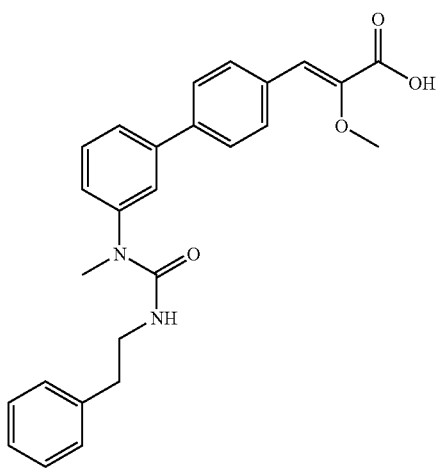 [SMILES: CO/C(=C\c1ccc(-c2cccc(N(C)C(=O)NCCc3ccccc3)c2)cc1)C(=O)O]

a-Methyl (Z)-2-methoxy-3-[3'-(1-methyl-3-phenethylureido)biphenyl-4-yl]acrylate

In a manner similar to that of Example 10d, starting with 1.7 g (3.2 mmol) of methyl (Z)-2-methoxy-3-{3'-[methyl-(4-nitrophenoxycarbonyl)amino]biphenyl-4-yl}acrylate and 0.5 mL (3.9-mL) of phenethylamine, 0.6 g (44%) of methyl (Z)-2-methoxy-3-[3'-(1-methyl-3-phenethylureido)biphenyl-4-yl]acrylate are obtained in the form of a white solid with a melting point of 61° C.

b-(Z)-2-methoxy-3-[3'-(1-methyl-3-phenethylureido)biphenyl-4-yl]acrylic acid 1.7 mL (1.7 mmol) of aqueous 1 N sodium hydroxide solution are added to a solution of 0.5 g (1.1 mmol) of methyl (Z)-2-methoxy-3-[3'-(1-methyl-3-phenethylureido)biphenyl-4-yl]acrylate in 10 mL of tetrahydrofuran. The reaction medium is heated at 68° C. and stirred for 4 hours. The reaction medium is acidified with 2 mL of 1 N acetic acid solution and extracted with ethyl acetate. The organic phase is washed with water, dried over magnesium sulfate, filtered and evaporated. The residue obtained is recrystallized from hot ethyl acetate. 500 mg (71%) of (Z)-2-methoxy-3-[3'-(1-methyl-3-phenethylureido)biphenyl-4-yl]acrylic acid are obtained in the form of a white solid with a melting point of 144° C.

$^1$H NMR (CDCl$_3$, 400 MHz): 2.77 (t, J=6.7-Hz, 2H); 3.33 (s, 3H); 3.46 (td, J=6.7-Hz, J=5.4-Hz, 2H); 3.89 (s, 3H); 4.43 (t, J=5.4-Hz, 1H); 7.07-7.19 (m, 7H); 7.42 (s, 1H); 7.44 (d, J=7.8-Hz, 1H); 7.52 (m, 1H); 7.55 (d, J=8.1-Hz, 2H); 7.88 (d, J=8.1-Hz, 2H); 10.70 (s, 1H).

EXAMPLE 17

Synthesis of Methyl (Z)-2-methoxy-3-[3'-(1-methyl-3-phenylureido)biphenyl-4-yl]acrylate

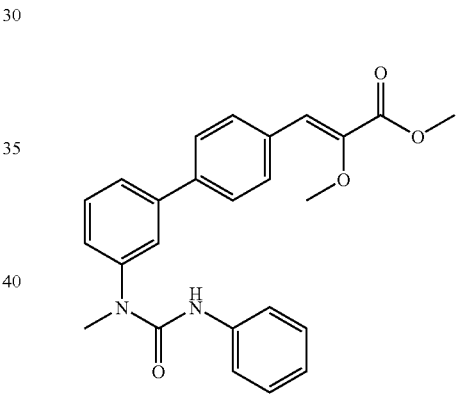

a-Methyl (Z)-2-methoxy-3-[3'-(1-methyl-3-phenylureido)biphenyl-4-yl]acrylate 0.8 g (2.7 mmol) of methyl (Z)-2-methoxy-3-(3'-methylaminobiphenyl-4-yl)acrylate and 1.8 mL (16.2 mmol) of phenyl isocyanate are heated at 50° C. for 5 hours. The reaction medium is cooled, 10 mL of pentane are added and the product precipitates. After filtration, the solid obtained is recrystallized from ethyl acetate. 0.83 g (75%) of methyl (Z)-2-methoxy-3-[3'-(1-methyl-3-phenylureido)biphenyl-4-yl]acrylate is obtained in the form of a white solid with a melting point of 186° C.

$^1$H NMR (CDCl$_3$, 400 MHz): 3.40 (s, 3H); 3.83 (s, 3H); 3.88 (s, 3H); 6.31 (s, 1H); 7.00 (m, 1H); 7.04 (s, 1H); 7.24 (m, 1H); 7.29-7.33 (m, 2H); 7.56-7.60 (m, 3H); 7.63 (d, J=8.4-Hz, 2H); 7.85 (d, J=8.4-Hz, 2H).

EXAMPLE 18

Synthesis of (Z)-2-methoxy-3-[3'-(1-methyl-3-phenylureido)biphenyl-4-yl]acrylic acid

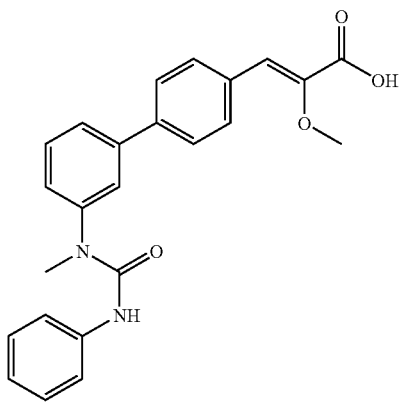 [SMILES: CO/C(=C\c1ccc(-c2cccc(N(C)C(=O)Nc3ccccc3)c2)cc1)C(=O)O]

a-(Z)-2-methoxy-3-[3'-(1-methyl-3-phenylureido)biphenyl-4-yl]acrylic acid 2.5 mL (2.5 mmol) of aqueous 1 N sodium hydroxide solution are added to a solution of 0.7 g (1.7 mmol) of methyl (Z)-2-methoxy-3-[3'-(1-methyl-3-phenylureido)biphenyl-4-yl]acrylate in 12 mL of tetrahydrofuran. The reaction medium is heated at 68° C. and stirred for 4 hours. The reaction medium is acidified with 2.6 mL of 1 N acetic acid solution and extracted with ethyl acetate. The organic phase is washed with water, dried over magnesium sulfate, filtered and evaporated. The residue obtained is filtered from hot ethanol. 410 mg (60%) of (Z)-2-methoxy-3-[3'-(1-methyl-3-phenylureido)biphenyl-4-yl]acrylic acid are obtained in the form of a white solid with a melting point of 223° C.

$^1$H NMR (CDCl$_3$, 400 MHz): 3.40 (s, 3H); 3.84 (s, 3H); 6.40 (s, 1H); 7.00 (m, 1H); 7.04 (s, 1H); 7.24 (m, 1H); 7.29-7.33 (m, 2H); 7.56-7.60 (m, 3H); 7.63 (d, J=8.4-Hz, 2H); 7.85 (d, J=8.4-Hz, 2H); 10.70 (s, 1H).

EXAMPLE 19

Synthesis of (E)-3-{3'-[(benzoylmethylamino)methyl]-2-butoxybiphenyl-4-yl}-2-methylacrylic acid

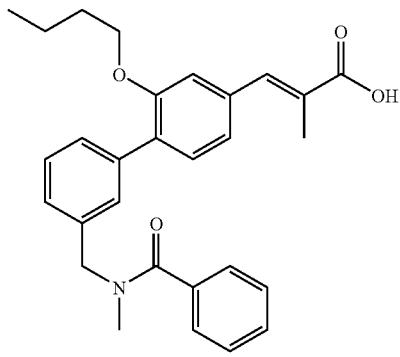 [SMILES: CCCCOc1cc(/C=C(\C)C(=O)O)ccc1-c1cccc(CN(C)C(=O)c2ccccc2)c1]

a-tert-Butyl (3-bromobenzyl)carbamate

A solution of 25 g (110 mmol) of 3-bromobenzylamine hydrochloride and 24.5 g (110 mmol) of tert-butyl dicarbonate in 250 mL of dichloromethane in the presence of 15.6 mL (110 mmol) of triethylamine is stirred at room temperature for 16 hours. The reaction medium is washed with water, the phases are separated by settling and the organic phase is dried over sodium sulfate. The solvent is evaporated off and 32.4 g (100%) of tert-butyl (3-bromobenzyl)carbamate are obtained in the form of crystals.

b-tert-Butyl (3-bromobenzyl)methylcarbamate 5.4 g (134 mmol) of 60% sodium hydride are added to a solution of 32 g (111 mmol) of tert-butyl (3-bromobenzyl)carbamate in 450 mL of dimethylformamide. The reaction medium is stirred at room temperature for 30 minutes and 21 mL (335 mmol) of iodomethane are then added. The reaction medium is stirred at room temperature for 20 hours and then hydrolyzed in water and extracted with ethyl acetate. The organic phases are combined, washed with saturated sodium chloride solution and dried over sodium sulfate. The solvent is evaporated off and 36.2 g (100%) of tert-butyl (3-bromobenzyl)methylcarbamate are obtained in the form of an orange-colored oil.

c-tert-Butyl N-methyl[3-(4,4,5,5-tetramethyl[11.3.2]dioxaborolan-2-yl)benzyl]carbamate:

In a manner similar to that of Example 1f, by reacting 33 g (110 mmol) of tert-butyl (3-bromobenzyl)methylcarbamate, 29 g (115 mmol) of bis-pinacoldiborane and 32 g (330 mmol) of potassium acetate in 500 mL of dimethylformamide in the presence of 3.6 g (4 mol %) of diphenylphosphinoferrocene-palladium dichloride (PdCl$_2$dppf), 31.6 g (83%) of tert-butyl N-methyl[3-(4,4,5,5-tetramethyl[1.3.2]dioxaborolan-2-yl)benzyl]carbamate are obtained in the form of a green oil after purification of the crude residue by chromatography on a column of silica eluted with a 90/10 heptane/ethyl acetate mixture.

d-Methyl 3-hydroxy-4-iodobenzoate 21 g (520 mmol) of sodium hydroxide and then 78.7 g (520 mmol) of sodium iodide are added to a solution of 69 g (500 mmol) of 3-hydroxybenzoic acid in 700 mL of methanol. The reaction mixture is cooled to 0° C. and aqueous sodium hypochlorite solution is then added (520 mmol). The reaction medium is stirred at 0-5° C. for 2 hours and then at room temperature overnight. The methanol is evaporated off and the reaction medium is then acidified with concentrated hydrochloric acid solution. The precipitated product is filtered off, washed with water and dried. 41.92 g of 3-hydroxy-4-iodobenzoic acid are obtained in the form of an off-white solid. The aqueous phase is extracted with ethyl acetate, dried over magnesium sulfate, filtered and evaporated and the residue obtained is taken up in heptane and then filtered.

Overall, 61.31 g of 3-hydroxy-4-iodobenzoic acid are obtained in the form of a white solid. 47 g (150 mmol) of this 3-hydroxy-4-iodobenzoic acid are placed in 300 mL of methanol and 6.13 g (35.6 mmol) of para-toluenesulfonic acid are added. The reaction mixture is heated at 70° C. for 48 hours.— The reaction is stopped by addition of 1 l of water. The precipitated product is filtered off and rinsed with water to neutral pH. 37.4 g (76%) of methyl 3-hydroxy-4-iodobenzoate are obtained in the form of a beige-colored powder.

e-Methyl 3-butoxy-4-iodobenzoate 6.15 mL (54 mmol) of iodobutane and then 14.9 g (108 mmol) of potassium carbonate are added to 10 g (36 mmol) of methyl 3-hydroxy-4-iodobenzoate in 100 mL of methyl ethyl ketone. The reaction mixture is heated at reflux for 1 hour 30 minutes. The reaction medium is filtered off and the filtrate is evaporated to dryness. The solid obtained is taken up in heptane, filtered and dried. 11.7 g (97%) of methyl 3-butoxy-4-iodobenzoate are obtained in the form of off-white crystals.

f-(3-Butoxy-4-iodophenyl)methanol 2.3 g (104.6 mmol) of lithium borohydride are added to 11.65 g (34.8 mmol) of methyl 3-butoxy-4-iodobenzoate in 60 mL of tetrahydrofuran. The reaction mixture is heated at 60° C. for 2 hours. The reaction medium is hydrolyzed in ice-cold saturated ammonium chloride solution, then acidified with 2 N hydrochloric acid solution and extracted with ethyl acetate. The organic phases are combined, washed with water and then saturated sodium chloride solution and dried over magnesium sulfate. After evaporating off the solvent, 10.6 g (99%) of (3-butoxy-4-iodophenyl)methanol are obtained in the form of a yellowish oil.

Rf=0.4 (70/30 heptane/EtOAc)

g-3-butoxy-4-iodobenzaldehyde 21.2 g (207 mmol) of manganese dioxide are added to 10.6 g (34.5 mmol) of (3-butoxy-4-iodophenyl)methanol in 70 mL of dichloromethane. The reaction mixture is stirred at room temperature for 2 days. The reaction medium is filtered through Celite. The filtrate is evaporated and the oil obtained (9.45 g) is purified by chromatography on silica gel eluted with a 90/10 heptane/ethyl acetate mixture. 7.7 g (73%) of 3-butoxy-4-iodobenzaldehyde are obtained in the form of a yellow oil.

h-Ethyl (E)-3-(3-butoxy-4-iodophenyl)-2-methylacrylate

A solution of 8.25 mL (37.8 mmol) of 2-triethyl phosphonopropionate in 20 mL of tetrahydrofuran is added to a mixture of 1.52 g (37.8 mmol) of sodium hydride in 15 mL of tetrahydrofuran. The reaction medium is stirred for 20 minutes. A solution of 3.83 g (12.6 mmol) of 3-butoxy-4-iodobenzaldehyde in 15 mL of tetrahydrofuran is then added to the reaction mixture and the reaction medium is then stirred at room temperature for 2 hours 30 minutes. The reaction medium is poured into saturated ammonium chloride solution and extracted with ethyl acetate. The organic phases are combined, washed with water and then with saturated sodium chloride solution and dried over magnesium sulfate. The solvent is evaporated off and the residue (10.7 g) is purified by chromatography on silica gel eluted with a 95/5 heptane/ethyl acetate mixture. 4.8 g (97%) of ethyl (E)-3-(3-butoxy-4-iodophenyl)-2-methylacrylate are obtained in the form of a yellow oil that crystallizes.

i-Ethyl (E)-3-{2-butoxy-3'-[(tert-butoxycarbonylmethylamino)methyl]biphenyl-4-yl}-2-methylacrylate 6 mg (1 mol %) of palladium acetate and then 18 mg (2 mol %) of 2-(dicyclohexylphosphino)biphenyl are added to a mixture, degassed beforehand, of 1 g (2.6 mmol) of ethyl (E)-3-(3-butoxy-4-iodophenyl)-2-methylacrylate prepared in Example 19h, 1.2 g (3.4 mmol) of tert-butyl N-methyl[3-(4,4,5,5-tetramethyl[1.3.2]dioxaborolan-2-yl)benzyl]carbamate prepared in Example 19c and 13 mL of aqueous 2 M potassium phosphate solution in 2.6 mL of dimethylformamide. The reaction mixture is heated at 90-95° C. for 2 hours. The reaction medium is hydrolyzed with saturated aqueous ammonium chloride solution and extracted with ethyl acetate. The organic phases are combined, washed with saturated sodium chloride solution and dried over magnesium sulfate. The solvent is evaporated off and the brown oil obtained (1.3 g) is purified by chromatography on a column of silica eluted with a 70/30 heptane/ethyl acetate mixture. 1.1 g (80%) of ethyl (E)-3-{2-butoxy-3'-[(tert-butoxycarbonylmethylamino)methyl]biphenyl-4-yl}-2-methylacrylate are obtained.

j-Ethyl (E)-3-(2-butoxy-3'-methylaminomethylbiphenyl-4-yl)-2-methylacrylate g (2.2 mmol) of ethyl (E)-3-{2-butoxy-3'-[(tert-butoxycarbonylmethylamino)methyl]biphenyl-4-yl}-2-methylacrylate in 10 mL of dichloromethane and 1.5 mL of trifluoroacetic acid are stirred at room temperature for 2 hours 30 minutes. The reaction medium is evaporated to dryness and purified by chromatography on a column of silica eluted with a 98/2 and then 95/5 mixture of ethyl acetate and methanol. 1.1 g (84%) of ethyl (E)-3-(2-butoxy-3'-methylaminomethylbiphenyl-4-yl)-2-methylacrylate trifluoroacetate are obtained in the form of an orange oil.

k-Ethyl (E)-3-{3'-[(benzoylmethylamino)methyl]-2-butoxybiphenyl-4-yl}-2-methylacrylate 142 µL of benzoyl chloride (1.2 mmol) are added to a solution of 0.36 g (0.6 mmol) of ethyl (E)-3-(2-butoxy-3'-methylaminomethylbiphenyl-4-yl)-2-methylacrylate trifluoroacetate, 6.5 mL of dichloromethane, 257 µL (1.84 mmol) of triethylamine and 7 mg (10 mol %) of 4-dimethylaminopyridine. The reaction medium is stirred at room temperature for 18 hours and then treated with 1 N hydrochloric acid solution and washed with water. The organic phase is dried over magnesium sulfate, filtered and evaporated. The crude residue obtained is purified by chromatography on a column of silica eluted with an 85/15 and then 70/30 heptane/ethyl acetate mixture. 270 mg (91%) of ethyl (E)-3-{3'-[(benzoylmethylamino)methyl]-2-butoxybiphenyl-4-yl}-2-methylacrylate are obtained in the form of a yellow oil.

l-(E)-3-{3'-[(benzoylmethylamino)methyl]-2-butoxybiphenyl-4-yl}-2-methylacrylic acid 265 mg (0.55 mmol) of ethyl (E)-3-{3'-[(benzoylmethylamino)methyl]-2-butoxybiphenyl-4-yl}-2-methylacrylate are placed in a solution of 109 mg (2.75 mmol) of sodium hydroxide in 5 mL of ethanol. After heating at 50-55° C. for 6 hours, the reaction medium is evaporated to dryness, taken up in water, acidified to pH 3 with aqueous 1 N hydrochloric acid solution and extracted with ethyl acetate. The organic phase is washed with water, dried over magnesium sulfate, filtered and evaporated. The residue obtained is recrystallized from a 50/50 heptane/ethyl acetate mixture. 165 mg (66%) of (E)-3-{3'-[(benzoylmethylamino)methyl]-2-butoxybiphenyl-4-yl}-2-methylacrylic acid are obtained in the form of an off-white powder with a melting point of 166° C.

$^1$H NMR (δ, CDCl$_3$): 0.89 (t, J=7.4-Hz, 3H); 1.40 (m, 2H); 1.71 (m, 2H); 2.22 (s, 3H); 2.91-3.08 (m, 3H); 3.99 (t, J=6.4-Hz, 2H); 4.57-4.82 (m, 2H); 7.03 (s, 1H); 7.13 (d, J=7.8-Hz, 1H); 7.40-7.57 (m, 10H); 7.83 (s, 1H).

EXAMPLE 20

Synthesis of (E)-3-(2-butoxy-3'-{[(4-methoxybenzoyl)methylamino]methyl}biphenyl-4-yl)-2-methylacrylic acid

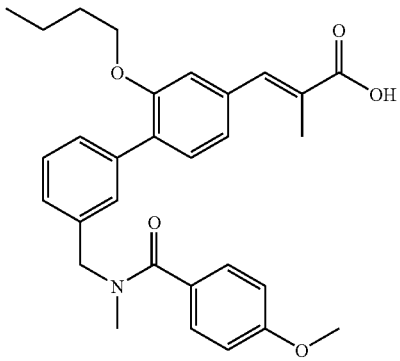 [SMILES: CCCCOc1cc(/C=C(\C)C(=O)O)ccc1-c1cccc(CN(C)C(=O)c2ccc(OC)cc2)c1]

a-Ethyl (E)-3-(2-butoxy-3'-{[(4-methoxybenzoyl)methylamino]methyl}biphenyl-4-yl)-2-methylacrylate In a manner similar to that of Example 19k, starting with 0.36 g (0.6 mmol) of ethyl (E)-3-(2-butoxy-3'-methylaminomethylbiphenyl-4-yl)-2-methylacrylate trifluoroacetate (prepared as in Example 19j) and 168 μL (1.2 mmol) of 4-methoxybenzoyl chloride, 320 mg (100%) of ethyl (E)-3-(2-butoxy-3'-{[(4-methoxybenzoyl)methylamino]methyl}biphenyl-4-yl)-2-methylacrylate are obtained in the form of a yellow oil.

b-(E)-3-(2-butoxy-3'-{[(4-methoxybenzoyl)methylamino]methyl}biphenyl-4-yl)-2-methylacrylic acid In a manner similar to that of Example 19l, starting with 315 mg (0.6 mmol) of ethyl (E)-3-(2-butoxy-3'-{[(4-methoxybenzoyl)methylamino]methyl}biphenyl-4-yl)-2-methylacrylate, 157 mg (53%) of (E)-3-(2-butoxy-3'-{[(4-methoxybenzoyl)methylamino]methyl}biphenyl-4-yl)-2-methylacrylic acid are obtained in the form of a white solid with a melting point of 60° C. after recrystallization from a 50/50 heptane/ethyl acetate mixture.

$^1$H NMR (δ, CDCl$_3$): 0.89 (t, J=7.3-Hz, 3H); 1.41 (m, 2H); 1.71 (m, 2H); 2.2 (s, 3H); 3.03 (m, 3H); 3.82 (s, 3H); 3.99 (t, J=6.4-Hz, 2H); 4.64-4.77 (m, 2H); 6.89 (d, J=7.0-Hz, 1H); 7.03 (s, 1H); 7.13 (d, J=7.8-Hz, 1H); 7.36-7.51 (m, 6H); 7.83 (s, 1H).

EXAMPLE 21

Synthesis of (E)-3-(2-butoxy-3'-{[(3-methoxybenzoyl)methylamino]methyl}biphenyl-4-yl)-2-methylacrylic acid

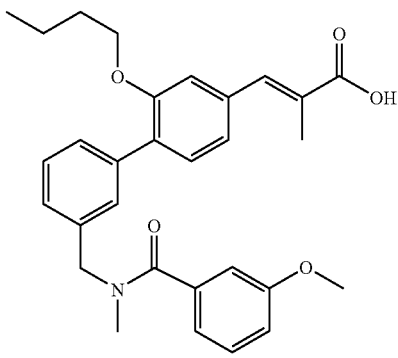 [SMILES: CCCCOc1cc(/C=C(\C)C(=O)O)ccc1-c1cccc(CN(C)C(=O)c2cccc(OC)c2)c1]

a-Ethyl (E)-3-(2-butoxy-3'-{[(3-methoxybenzoyl)methylamino]methyl}biphenyl-4-yl)-2-methylacrylate In a manner similar to that of Example 19k, starting with 0.36 g (0.6 mmol) of ethyl (E)-3-(2-butoxy-3'-methylaminomethylbiphenyl-4-yl)-2-methylacrylate trifluoroacetate (prepared as in Example 19j) and 171 μL (1.2 mmol) of 3-methoxybenzoyl chloride, 343 mg (100%) of ethyl (E)-3-(2-butoxy-3'-{[(3-methoxybenzoyl)methylamino]methyl}biphenyl-4-yl)-2-methylacrylate are obtained in the form of a yellow oil.

b-(E)-3-(2-butoxy-3'-{[(3-methoxybenzoyl)methylamino]methyl}biphenyl-4-yl)-2-methylacrylic acid In a manner similar to that of Example 19l, starting with 338 mg (0.66 mmol) of ethyl (E)-3-(2-butoxy-3'-{[(3-methoxybenzoyl)methylamino]methyl}biphenyl-4-yl)-2-methylacrylate, 205 mg (64%) of (E)-3-(2-butoxy-3'-{[(3-methoxybenzoyl)methylamino]methyl}biphenyl-4-yl)-2-methylacrylic acid are obtained in the form of a white solid with a melting point of 60° C. after purification by chromatography on a column of silica eluted with a 50/50 heptane/ethyl acetate mixture.

$^1$H NMR (δ, CDCl$_3$): 0.89 (t, J=7.3-Hz, 3H); 1.40 (m, 2H); 1.71 (m, 2H); 2.21 (s, 3H); 2.91-3.09 (m, 3H); 3.71-3.83 (m, 3H); 3.99 (t, J=6.4-Hz, 2H); 4.56-4.81 (m, 2H); 6.94 (m, 1H); 7.01-7.03 (m, 3H); 7.12 (d, J=7.8-Hz, 1H); 7.30-7.56 (m, 7H); 7.83 (s, 1H).

EXAMPLE 22

Synthesis of 2-[1-{3'-[(benzoylmethylamino)methyl]-2-butoxybiphenyl-4-yl}meth-(E)-ylidene]butyric acid

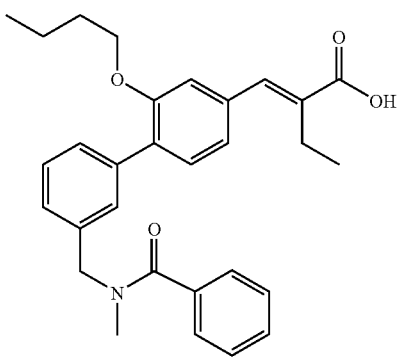 [SMILES: CCCCOc1cc(/C=C(\CC)C(=O)O)ccc1-c1cccc(CN(C)C(=O)c2ccccc2)c1]

a-Ethyl 2-[1-(3-butoxy-4-iodophenyl)meth-(E)-ylidene]butyrate

A solution of 9 mL (37.8 mmol) of triethyl 2-phosphonobutyrate in 20 mL of tetrahydrofuran is added to a mixture of 1.52 g (37.8 mmol) of sodium hydride in 15 mL of tetrahydrofuran. The reaction medium is stirred for 20 minutes. A solution of 3.83 g (12.6 mmol) of 3-butoxy-4-iodobenzaldehyde (prepared as described in Example 19g) in 15 mL of tetrahydrofuran is then added to the reaction mixture and the reaction medium is stirred at room temperature for 2 hours 30 minutes. The reaction medium is poured into saturated ammonium chloride solution and extracted with ethyl acetate. The organic phases are combined, washed with saturated sodium chloride solution and dried over magnesium sulfate. The solvent is evaporated off and the residue (11.49 g) is purified by chromatography on silica gel eluted with a 95/5 heptane/ethyl acetate mixture. 4.90 g (97%) of ethyl 2-[1-(3-butoxy-4-iodophenyl)meth-(E)-ylidene]butyrate are obtained in the form of a yellow oil that crystallizes.

b-Ethyl 2-[1-{2-butoxy-3'-[(tert-butoxycarbonylmethylamino)methyl]biphenyl-4-yl}meth-(E)-ylidene]butyrate In a manner similar to that of Example 19i, starting with 1.05 g (2.6 mmol) of ethyl (E)-3-(3-butoxy-4-iodophenyl)-2-ethylacrylate and 1.2 g (3.4 mmol) of tert-butyl N-methyl[3-(4,4,5,5-tetramethyl[1.3.2]dioxaborolan-2-yl)benzyl]carbamate, 2.3 g (80%) of ethyl 2-[1-{2-butoxy-3'-[(tert-butoxycarbonylmethylamino)methyl]biphenyl-4-yl}meth-(E)-ylidene]butyrate are obtained.

c-Ethyl 2-[1-(2-butoxy-3'-methylaminomethylbiphenyl-4-yl)meth-(E)-ylidene]butyrate In a manner similar to that of Example 19j, starting with 1 g (2 mmol) of ethyl 2-[1-{2-butoxy-3'-[(tert-butoxycarbonylmethylamino)methyl]biphenyl-4-yl}meth-(E)-ylidene]butyrate, 1 g (80%) of ethyl 2-[1-(2-butoxy-3'-methylaminomethylbiphenyl-4-yl)meth-(E)-ylidene]butyrate trifluoroacetate is obtained in the form of a yellow oil.

d-Ethyl 2-[1-{3'-[(benzoylmethylamino)methyl]-2-butoxybiphenyl-4-yl}meth-(E)-ylidene]butyrate In a manner similar to that of Example 19k, starting with 0.4 g (0.6 mmol) of ethyl 2-[1-(2-butoxy-3'-methylaminomethylbiphenyl-4-yl)meth-(E)-ylidene]butyrate trifluoroacetate and 142 μL (1.2 mmol) of benzoyl chloride, 0.3 g (91%) of ethyl 2-[1-{3'-[(benzoylmethylamino)methyl]-2-butoxybiphenyl-4-yl}meth-(E)-ylidene]butyrate are obtained in the form of a yellow oil.

e-2-[1-{3'-[(Benzoylmethylamino)methyl]-2-butoxybiphenyl-4-yl}meth-(E)-ylidene]butyric acid In a manner similar to that of Example 19l, starting with 0.3 g (0.5 mmol) of ethyl 2-[1-{3'-[(benzoylmethylamino)methyl]-2-butoxybiphenyl-4-yl}meth-(E)-ylidene]butyrate, 0.2 g (70%) of 2-[1-{3'-[(benzoylmethylamino)methyl]-2-butoxybiphenyl-4-yl}meth-(E)-ylidene]butyric acid is obtained in the form of a pale orange solid with a melting point of 115° C.

$^1$H NMR (δ, CDCl$_3$): 0.89 (t, J=7.3-Hz, 3H); 1.27 (t, J=7.4-Hz, 3H); 1.42 (m, 2H); 1.72 (m, 2H); 2.64 (q, J=7.3-Hz, 2H); 2.9-3.1 (m, 3H); 3.99 (t, J=6.5-Hz, 2H); 4.57-4.82 (m, 2H); 7.02 (s, 1H); 7.10 (d, J=7.8-Hz, 1H); 7.40-7.57 (m, 10H); 7.80 (s, 1H).

EXAMPLE 23

Synthesis of (Z)-3-[2-butoxy-3'-(1-methyl-3-phenethylureido)biphenyl-4-yl]-2-ethoxyacrylic acid

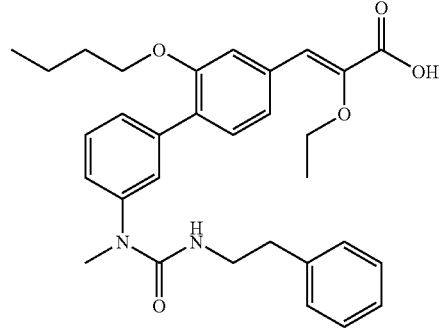 [SMILES: CCCCOc1cc(/C=C(\OCC)C(=O)O)ccc1-c1cccc(N(C)C(=O)NCCc2ccccc2)c1]

a-(Z)-3-(3-butoxy-4-iodophenyl)-2-ethoxyacrylic acid 24 mL (65 mmol) of a 21% solution of sodium ethoxide in ethanol and then 5.2 g (77 mmol) of solid sodium ethoxide are added portionwise to a solution of ethyl chloroacetate in 25 mL of ethanol cooled beforehand to 10° C. The reaction medium is stirred at 10° C. for 1 hour and a solution of 4.8 mL (40 mmol) of diethyl carbonate in 7 mL of ethanol is then added dropwise to the reaction medium.

After cooling to 4° C., 8.7 g (43 mmol) of 3-butoxy-4-iodobenzaldehyde (prepared beforehand as described in Example 19g) are added. The reaction medium is then stirred for 18 hours at room temperature and then cooled to 15° C., and 15 mL of water and 15 mL of 40% sodium hydroxide solution are added. After stirring at room temperature for 2 hours, the reaction medium is concentrated to a volume of 100 mL and a further 20 mL of water are added. The reaction medium is cooled to 4° C., and 28 mL of 35% hydrochloric acid solution are added slowly. The reaction medium is extracted with ethyl acetate, the organic phase is washed with water, dried over magnesium sulfate, filtered and evaporated. The crude residue obtained is purified by chromatography on a column of silica eluted with a 1/1 heptane/ethyl acetate mixture.

3.1 g (28%) of (Z)-3-(3-butoxy-4-iodophenyl)-2-ethoxyacrylic acid are obtained.

b-Methyl (Z)-3-(3-butoxy-4-iodophenyl)-2-ethoxyacrylate

In an Emrys Optimizer microwave reactor, 0.8 g (2 mmol) of (Z)-3-(3-butoxy-4-iodophenyl)-2-ethoxyacrylic acid is dissolved in 10 mL of methanol and 1 mL of concentrated sulfuric acid and heated at 70° C. by microwave for 2 hours. After addition of water, the reaction medium is extracted with ethyl acetate. The organic phase is washed with water, dried over magnesium sulfate, filtered and evaporated. 0.5 g (61%) of methyl (Z)-3-(3-butoxy-4-iodophenyl)-2-ethoxyacrylate is obtained.

c-Methyl (Z)-3-(2-butoxy-3'-methylaminobiphenyl-4-yl)-2-ethoxyacrylate

To a solution of 0.4 g (1 mmol) of methyl (Z)-3-(3-butoxy-4-iodophenyl)-2-ethoxyacrylate in 8 mL of ethylene glycol dimethyl ether placed under nitrogen, 0.25 g (1.1 mmol) of methyl[3-(4,4,5,5-tetramethyl[1.3.2]dioxaborolan-2-yl)phenyl]amine (prepared as in Example 10a), 1.5 mL (3 mmol) of aqueous 2 M potassium phosphate solution, 2 mg (0.01 mmol) of palladium (II) acetate and 7 mg (0.02 mmol) of dicyclohexyl-o-biphenylphosphine are added. The reaction medium is then heated at 80° C. for 20 hours. After addition of water, the reaction medium is extracted with ethyl acetate. The organic phase is washed with water, dried over magnesium sulfate, filtered and evaporated. The residue obtained is purified by chromatography on a column of silica eluted with an 85/15 heptane/ethyl acetate mixture. 0.2 g (63%) of methyl (Z)-3-(2-butoxy-3'-methylaminobiphenyl-4-yl)-2-ethoxyacrylate are obtained.

d-Methyl (Z)-3-[2-butoxy-3'-(1-methyl-3-phenethylureido)biphenyl-4-yl]-2-ethoxyacrylate 40 mg (0.1 mmol) of methyl (Z)-3-(2-butoxy-3'-methylaminobiphenyl-4-yl)-2-ethoxyacrylate and 16 mg (0.11 mmol) phenethyl isocyanate are heated at 85° C. by microwave in an Emrys Optimizer machine for 20 minutes. The residue obtained is purified by chromatography on a column of silica eluted with a 95/5 and then 90/10 heptane/ethyl acetate mixture. 40 mg (72%) of methyl (Z)-3-[2-butoxy-3'-(1-methyl-3-phenethylureido)biphenyl-4-yl]-2-ethoxyacrylate are obtained.

e-(Z)-3-[2-butoxy-3'-(1-methyl-3-phenethylureido)biphenyl-4-yl]-2-ethoxyacrylic acid 40 mg (0.08 mmol) of methyl (Z)-3-[2-butoxy-3'-(1-methyl-3-phenethylureido)biphenyl-4-yl]-2-ethoxyacrylate are placed in 0.5 mL of a 5/1/1 by volume mixture of tetrahydrofuran/methanol/water, 17 mg (0.4 mmol) of lithium hydroxide monohydrate are added and the reaction medium is stirred at room temperature for 18 hours. The reaction medium is acidified to pH 3 with acetic acid and then extracted with ethyl acetate. The organic phase is washed with water, dried over magnesium sulfate, filtered and evaporated. The residue obtained is purified by chromatography on a column of silica eluted with an 85/15 and then 60/40 heptane/ethyl acetate mixture. 16 mg (34%) of (Z)-3-[2-butoxy-3'-(1-methyl-3-phenethylureido)biphenyl-4-yl]-2-ethoxyacrylic acid are obtained.

$^1$H NMR (δ, CDCl$_3$): 0.85 (t, J=7.4-Hz, 3H); 1.35 (t, J=7.1-Hz, 2H); 1.66 (m, 2H); 2.68 (t, J=6.8-Hz, 2H); 3.2 (s, 3H); 3.37 (dd, J=6.8-Hz, J=5.7-Hz, 2H); 3.94 (t, J=6.4-Hz); 4.05 (q, J=7.4-Hz, 2H); 4.37 (t, J=5.7-Hz, 1H); 6.99-7.07 (m, 7H); 7.19 (m, 1H); 7.29-7.42 (m, –4H); 7.55 (s, 1H).

EXAMPLE 24

Synthesis of (Z)-3-[2-butoxy-3'-(1-methyl-3-pentylureido)biphenyl-4-yl]-2-methoxyacrylic acid

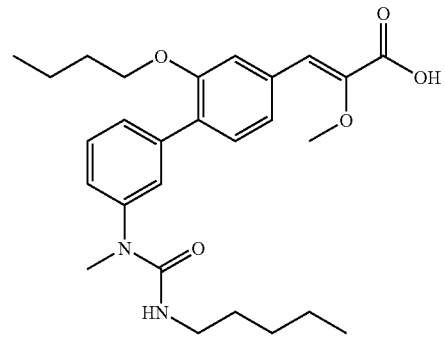 [SMILES: CCCCCNC(=O)N(C)c1cccc(-c2ccc(/C=C(\OC)C(=O)O)cc2OCCCC)c1]

a-Methyl chloromethoxyacetate 25 g (186 mmol) of commercial methyl dimethoxyacetate, 26.5 mL (373 mmol) of acetyl chloride and 95 mg (0.37 mmol) of iodine are placed in a round-bottomed flask and heated at 50° C. for 18 hours. The reaction progress is monitored by NMR. The excess acetyl chloride is removed by evaporation under vacuum P=150 mbar, at 35° C. (the final product has a fairly low boiling point). 27 g (100%) of methyl chloromethoxyacetate are obtained in the form of a liquid colored brown by the residual iodine.

b-Methyl (diethoxyphosphoryl)methoxyacetate 26 g (186 mmol) of methyl chloromethoxyacetate prepared above and 32 mL (186 mmol) of triethyl phosphite are placed in a round-bottomed flask and heated at 150° C. for 3 hours. The reaction progress is monitored by NMR. 45 g (100%) of methyl (diethoxyphosphoryl)methoxyacetate are obtained directly in the form of a colorless liquid.

c-Methyl (Z)-3-(3-butoxy-4-iodophenyl)-2-methoxyacrylate 0.7 g (16.5 mmol) of sodium hydride are added portionwise to a solution at 0° C. of 3.9 g (16.5 mmol) of methyl (diethoxyphosphoryl)methoxyacetate in 45 mL of tetrahydrofuran. The reaction mixture is stirred for 45 minutes at room temperature, followed by dropwise addition of 3.4 g (11.8 mmol) of 3-butoxy-4-iodobenzaldehyde (prepared as described in Example 19g) in 30 mL of tetrahydrofuran. The reaction is slightly exothermic and the reaction mixture is maintained at a temperature of 25-27° C. with an ice bath.

When the temperature has stabilized, the reaction mixture is stirred for 20 hours at room temperature. The reaction is worked up by addition of 60 mL of water and extraction with ethyl acetate. The organic phases are combined, washed with saturated sodium chloride solution and then dried over magnesium sulfate. The solvents are evaporated off. The crude product obtained is purified by chromatography on a column of silica eluted with a 98/2 heptane/ethyl acetate mixture. 1.5 g (33%) of the isomer methyl (Z)-3-(3-butoxy-4-iodophenyl)-2-methoxyacrylate are obtained in the form of a yellow solid and 1.0 g of the isomer (E)-3-(3-butoxy-4-iodophenyl)-2-methoxyacrylate are obtained in the form of a pale yellow oil.

d-tert-Butyl 3-bromophenylcarbamate

To a mixture of 122 g (709 mmol) of 3-bromoaniline, 99 mL of triethylamine (709 mmol) and 1 l of dichloromethane, 155 g (709 mmol) of di-tert-butyl dicarbonate are added portionwise, at room temperature. After stirring for 18 hours, the reaction medium is poured into ice-cold water and extracted with dichloromethane. The organic phase is separated out after settling of the phases, dried over magnesium sulfate, filtered and evaporated. 170 g (88%) of tert-butyl 3-bromophenylcarbamate are obtained.

e-tert-Butyl 3-bromophenyl-N-methylcarbamate

To a solution of 128 g (470 mmol) of tert-butyl 3-bromophenylcarbamate in 800 mL of dimethylformamide, 19 g (475 mmol) of sodium hydride (60% in oil) are added portionwise and the reaction medium is stirred until the evolution of gas has ceased. 29.3 mL (470 mmol) of methyl iodide are added dropwise and stirring is continued for 18 hours. The reaction medium is poured into ice-cold water and extracted with ethyl acetate. The organic phase is separated out after settling of the phases, dried over magnesium sulfate and evaporated. 152.5 g (92%) of tert-butyl 3-bromophenyl-N-methylcarbamate are obtained.

f-(3-bromophenyl)methylamine 150 g (500 mmol) of tert-butyl (3-bromophenyl)-N-methylcarbamate are placed in 600 mL of dichloromethane and 383 mL (5 mol) of trifluoroacetic acid. The reaction medium is stirred at room temperature for 24 hours, and then treated with saturated aqueous sodium carbonate solution and extracted with dichloromethane. The organic phase is washed with water, dried over magnesium sulfate, filtered and evaporated. 99 g (100%) of (3-bromophenyl)methylamine are obtained.

g-1-(3-bromophenyl)-1-methyl-3-pentylurea

A solution of 50 g (0.45 mol) of pentyl isocyanate in 50 mL of dichloromethane is added to a mixture of 82 g (0.45 mol) of (3-bromophenyl)methylamine in 250 mL of dichloromethane in the presence of 20 mL (0.14 mol) of triethylamine. The reaction medium is heated at reflux for 3 days and then hydrolyzed in 200 mL of 1 N hydrochloric acid solution and extracted with ethyl acetate. The organic phases are combined, washed with water, with saturated sodium chloride solution and evaporated. 123 g (93%) of 1-(3-bromophenyl)-1-methyl-3-pentylurea are obtained.

h-3-(1-methyl-3-pentylureido)phenylboronic acid 150 mL (0.24 mol) of methyllithium at 1.6M in diethyl ether are added to a solution cooled to −70° C. of 123 g (0.41 mol) of 1-(3-bromophenyl)-1-methyl-3-pentylurea in 1.21 of tetrahydrofuran. The reaction medium is stirred at −70° C. for 1 hour and 530 mL (0.91 mol) of a 1.7M solution of tert-butyllithium in pentane are added. The reaction medium is stirred at −70° C. for 45 minutes and 115 mL (0.91 mol) of trimethyl borate are then added. The reaction medium is stirred at room temperature for 1 hour and then hydrolyzed by addition of ice, acidified with 1 l of 2 N hydrochloric acid and extracted with ethyl acetate. The organic phases are combined, washed with water and dried over magnesium sulfate. The solvent is evaporated off and the residue is purified by chromatography on a column of silica eluted with a 1/1 heptane/ethyl acetate mixture and crystallization from a heptane/ethyl acetate mixture. 42 g (39%) of 3-(1-methyl-3-pentylureido)phenylboronic acid are obtained in the form of a pink solid.

i-Methyl (Z)-3-[2-butoxy-3'-(1-methyl-3-pentylureido)biphenyl-4-yl]-2-methoxyacrylate 0.4 g (1 mmol) of methyl (Z)-3-(3-butoxy-4-iodophenyl)-2-methoxyacrylate, 0.35 g (1.3 mmol) of 3-(1-methyl-3-pentylureido)phenylboronic acid and 1 mL (2 mmol) of potassium phosphate are dissolved in 10 mL of dimethylformamide. After bubbling nitrogen through the reaction mixture for 10 minutes, 2 mg (0.01 mmol) of palladium acetate and 7 mg (0.02 mmol) of 2-(dicyclohexylphosphine)biphenyl are added. The reaction mixture is heated at 90° C. for 1 hour 30 minutes with vigorous stirring.

After cooling, the reaction is worked up by addition of water and extraction with ethyl acetate. The organic phases are combined, washed with water and with saturated sodium chloride solution and then dried over magnesium sulfate. The solvents are evaporated off. The crude product obtained is purified by chromatography on a column of silica eluted with a 60/40 heptane/ethyl acetate mixture to give 0.4 g (82%) of methyl (Z)-3-[2-butoxy-3'-(1-methyl-3-pentylureido)biphenyl-4-yl]-2-methoxyacrylate in the form of a yellow oil.

j-(Z)-3-[2-butoxy-3'-(1-methyl-3-pentylureido)biphenyl-4-yl]-2-methoxyacrylic acid 1.24 mL (1.24 mmol) of aqueous 1 M sodium hydroxide solution are added to a solution of 0.4 g (0.83 mmol) of methyl (Z)-3-[2-butoxy-3'-(1-methyl-3-pentylureido)biphenyl-4-yl]-2-methoxyacrylate in 10 mL of tetrahydrofuran. The reaction mixture is stirred at 68° C. for 5 hours. After cooling, the reaction is worked up by addition of 3 mL (3 mmol) of aqueous 1 M hydrochloric acid solution and 10 mL of water and extraction with ethyl acetate. The organic phases are combined, washed with saturated sodium chloride solution and then dried over magnesium sulfate. The solvents are evaporated off. The product is recrystallized from a pentane/acetone mixture to give 0.3 g (76%) of (Z)-3-[2-butoxy-3'-(1-methyl-3-pentylureido)biphenyl-4-yl]-2-methoxyacrylic acid in the form of a cream-colored solid with a melting point of 61° C.

$^1$H NMR (CDCl$_3$, 400 MHz): 0.77 (t, J=7.1-Hz, 3H); 0.85 (t, J=6.9-Hz, 3H); 1.11-1.21 (m, 4H); 1.34-1.39 (m, 4H); 1.66-1.69 (m, 2H); 3.11 (m, 2H); 3.24 (s, 3H); 3.80 (s, 3H);

3.95 (t, J=6.5-Hz, 2H); 4.37 (m, 1H); 7.08 (s, 1H); 7.14 (d, J=7.7-Hz, 1H); 7.27 (d, J=7.7-Hz, 1H); 7.33 (d, J=8.0-Hz, 1H); 7.37-7.45 (m, 4H).

EXAMPLE 25

Synthesis of (Z)-3-[2-butoxy-3'-(3-heptyl-1-methylureido)biphenyl-4-yl]-2-methoxyacrylic acid

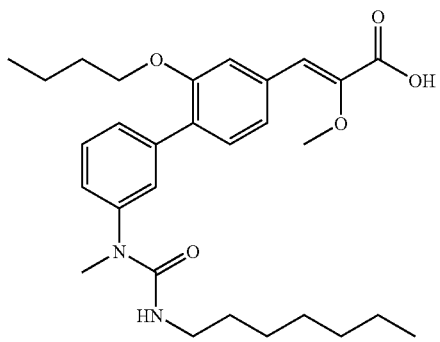 [SMILES: CCCCCCCNC(=O)N(C)c1cccc(-c2ccc(/C=C(\OC)C(=O)O)cc2OCCCC)c1]

a-1-(3-bromophenyl)-3-heptyl-1-methylurea

In a manner similar to that of Example 24g, by reacting 50 g (350 mmol) of heptyl isocyanate with 66 g (350 mmol) of (3-bromophenyl)methylamine (prepared as in Example 24f) in 300 mL of dichloromethane in the presence of 20 mL of triethylamine, 113 g (97%) of 1-(3-bromophenyl)-3-heptyl-1-methylurea are obtained.

b-3-(3-heptyl-1-methylureido)phenylboronic acid

In a manner similar to that of Example (24h), by reacting 113 g (345 mmol) of 1-(3-bromophenyl)-3-heptyl-1-methylurea in 1.1 l of tetrahydrofuran, 127 mL (380 mmol) of a 1.6M solution of methyllithium in diethyl ether, 530 mL (760 mmol) of a 1.7M solution of tert-butyllithium in pentane and 97 mL (904 mmol) of trimethyl borane, 36 g (36%) of 3-(3-heptyl-1-methylureido)phenylboronic acid are obtained in the form of a pink powder after purification of the crude residue by chromatography on silica gel eluted with a 50/50 heptane/ethyl acetate mixture and crystallization from an ethyl acetate/heptane mixture.

c-Methyl (Z)-3-[2-butoxy-3'-(1-methyl-3-heptylureido)biphenyl-4-yl]-2-methoxyacrylate 0.4 g (1 mmol) of methyl (Z)-3-(3-butoxy-4-iodophenyl)-2-methoxyacrylate prepared as described in Example 24c, 0.4 g (1.33 mmol) of 3-(3-heptyl-1-methylureido)phenylboronic acid and 1 mL (2 mmol) of potassium phosphate are dissolved in 10 mL of dimethylformamide. After bubbling nitrogen through the reaction mixture for 10 minutes, 2 mg (0.01 mmol) of palladium (II) acetate and 7 mg (0.02 mmol) of 2-(dicyclohexylphosphine)biphenyl are added. The reaction mixture is heated at 90° C. for 1 hour 30 minutes with vigorous stirring. After cooling, the reaction is worked up by addition of water and extraction with ethyl acetate. The organic phases are combined, washed with water and with saturated sodium chloride solution and then dried over magnesium sulfate. The solvents are evaporated off. The crude product obtained is purified by chromatography on a column of silica eluted with a 70/30 heptane/ethyl acetate mixture to give 0.44 g (85%) of methyl (Z)-3-[2-butoxy-3'-(1-methyl-3-heptylureido)biphenyl-4-yl]-2-methoxyacrylate in the form of an orange oil.

d-(Z)-3-[2-butoxy-3'-(1-methyl-3-heptylureido)biphenyl-4-yl]-2-methoxyacrylic acid 1.3 mL (1.3 mmol) of aqueous 1 M sodium hydroxide solution are added to a solution of 0.44 g (0.86 mmol) of methyl (Z)-3-[2-butoxy-3'-(1-methyl-3-pentylureido)biphenyl-4-yl]-2-methoxyacrylate in 10 mL of tetrahydrofuran. The reaction mixture is stirred at 68° C. for 6 hours. After cooling, the reaction is worked up by addition of 3 mL (3 mmol) of aqueous 1 M hydrochloric acid solution and 10 mL of water and extraction with ethyl acetate. The organic phases are combined, washed with saturated sodium chloride solution and then dried over magnesium sulfate. The solvents are evaporated off. The product is recrystallized from a pentane/acetone mixture to give 0.33 g (78%) of (Z)-3-[2-butoxy-3'-(1-methyl-3-heptylureido)biphenyl-4-yl]-2-methoxyacrylic acid in the form of a cream-colored solid with a melting point of 103° C.

$^1$H NMR (CDCl$_3$, 400 MHz): 0.85 (t, J=7.1-Hz, 3H); 0.95 (t, J=7.3-Hz, 3H); 1.24 (m, 8H); 1.42 (m, 4H); 1.78 (m, 2H); 3.18 (td, J=7.1-Hz, J=5.6-Hz, 2H); 3.33 (s, 3H); 3.89 (s, 3H); 4.05 (t, J=6.6-Hz, 2H); 4.46 (t, J=5.6-Hz, 1H); 7.17 (s, 1H); 7.23 (d, J=7.7-Hz, 1H); 7.35-7.54 (m, 6H).

EXAMPLE 26

Synthesis of (Z)-3-[2-butoxy-3'-(1-methyl-3-pentylureido)biphenyl-4-yl]-2-ethoxyacrylic acid

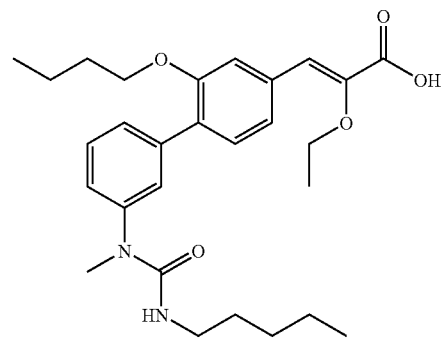 [SMILES: CCCCCNC(=O)N(C)c1cccc(-c2ccc(/C=C(\OCC)C(=O)O)cc2OCCCC)c1]

0.2 g (0.5 mmol) of (Z)-3-(3-butoxy-4-iodophenyl)-2-ethoxyacrylic acid prepared as described in Example 23a and 0.2 g (0.6 mmol) of 3-(1-methyl-3-pentylureido)phenylboronic acid prepared as in Example 24h are dissolved in 4 mL of a 75/25 solution of ethylene glycol dimethyl ether/water. After addition of 0.2 mL (1.2 mmol) of aqueous 2M potassium carbonate solution, 0.004 mg (0.005 mmol) of dichloro [1,1'-bis(diphenylphosphino)ferrocene]palladium is added and the reaction medium is heated at 80° C. for 18 hours. After addition of water, the reaction medium is extracted with ethyl acetate. The organic phase is washed with water, dried over magnesium sulfate, filtered and evaporated. The residue obtained is purified by chromatography on a column of silica eluted with an 8/2, 7/3 and then 5/5 heptane/ethyl acetate mixture. 50 mg (20%) of (Z)-3-[2-butoxy-3'-(1-methyl-3-pentylureido)biphenyl-4-yl]-2-ethoxyacrylic acid are obtained in the form of a beige-colored solid with a melting point of 59° C.

$^1$H NMR (δ, CDCl$_3$): 0.76 (t, J=7.2-Hz, 3H); 0.86 (t, J=7.4-Hz, 3H); 1.15-1.21 (m, 5H); 1.32-1.36 (m, 4H); 1.67 (m, 2H); 3.11 (dd, J=7.2-Hz, J=5.5-Hz, 2H); 3.23 (s, 3H); 3.94 (t, J=6.4-Hz, 2H); 4.05 (q, J=7.2-Hz, 2H); 4.35 (t, J=5.5-Hz, 1H); 7.06 (s, 1H); 7.13 (dd, J=7.6-Hz, J=2.9-Hz, 1H); 7.30-7.43 (m, 5H); 7.53 (s, 1H).

EXAMPLE 27

Synthesis of (Z)-3-[2-butoxy-3'-(3-heptyl-1-methylureido)biphenyl-4-yl]-2-ethoxyacrylic acid

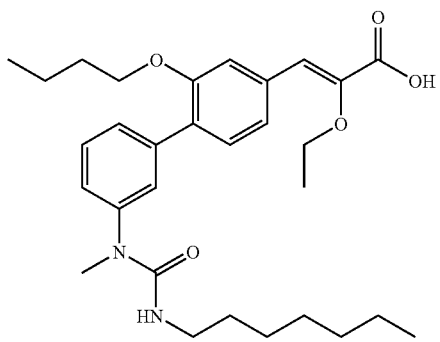 [SMILES: CCCCCCCNC(=O)N(C)c1cccc(-c2ccc(/C=C(\OCC)C(=O)O)cc2OCCCC)c1]

0.2 g (0.5 mmol) of (Z)-3-(3-butoxy-4-iodophenyl)-2-ethoxyacrylic acid prepared as described in Example 23a and 0.2 g (0.6 mmol) of 3-(3-heptyl-1-methylureido)phenylboronic acid prepared as described in Example 25b are dissolved in 4 mL of a 75/25 solution of ethylene glycol dimethyl ether/water. After addition of 0.2 mL (1.1 mmol) of aqueous 2 M potassium carbonate solution, 0.004 mg (0.005 mmol) of dichloro[1,1'-bis(diphenylphosphino)ferrocene]palladium are added and the reaction medium is heated at 80° C. for 18 hours. After addition of water, the reaction medium is extracted with ethyl acetate. The organic phase is washed with water, dried over magnesium sulfate, filtered and evaporated. The residue obtained is purified by chromatography on a column of silica eluted with an 8/2, 7/3 and then 5/5 heptane/ethyl acetate mixture. 60 mg (23%) of (Z)-3-[2-butoxy-3'-(3-heptyl-1-methylureido)biphenyl-4-yl]-2-ethoxyacrylic acid are obtained in the form of a beige-colored solid with a melting point of 103° C.

$^1$H NMR (δ, CDCl$_3$): 0.66 (t, J=7.1-Hz, 3H); 0.72 (t, J=6.7-Hz, 3H); 1.04 (m, 8H); 1.21-1.28 (m, 4H); 2.99 (t, J=7.0-Hz, 2H); 3.13 (s, 3H); 3.68 (s, 3H); 3.85 (t, J=6.5-Hz, 2H); 4.26 (m, 1H); 6.97 (s, 1H); 7.03 (d, J=7.7-Hz, 1H); 7.16 (d, J=7.8-Hz, 1H); 7.22 (d, J=8.0-Hz, 1H); 7.25-7.33 (m, 4H).

EXAMPLE 28

Synthesis of (Z)-3-[2-butoxy-3'-(3-butyl-1-methylureido)biphenyl-4-yl]-2-methoxyacrylic acid

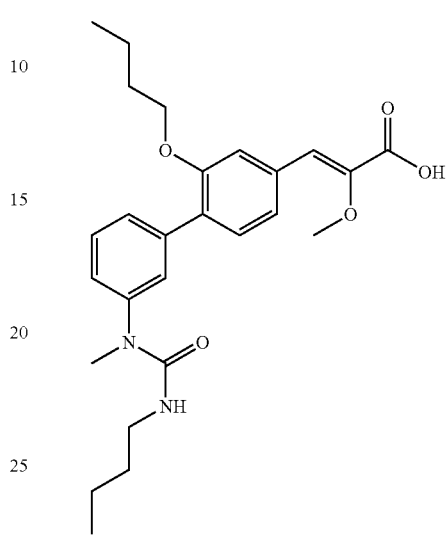

a-Methyl [3-(4,4,5,5-tetramethyl[1.3.2]dioxaborolan-2-yl)phenyl]amine 35 g (4 mol %) of diphenylphosphinoferrocenepalladium dichloride are added to a solution of 200 g (1 mol) of (3-bromophenyl)methylamine prepared as described in Example 24f and 287 g (1.1 mol) of bis-pinacoldiborane in 2 l of dimethylformamide in the presence of 316 g (3.2 mol) of potassium acetate. The reaction medium is heated at 100° C. for 3 hours and then stirred at room temperature for 15 hours. The reaction medium is filtered through Celite and 2 l of ethyl acetate are then added to the filtrate. The organic medium is washed with water and the phases are then separated by settling. The solvents are evaporated off and the black oil obtained is purified by chromatography on silica gel eluted with a heptane/ethyl acetate mixture (90/10). 183 g (73%) of methyl[3-(4,4,5,5-tetramethyl[1.3.2]dioxaborolan-2-yl)phenyl]amine are obtained in the form of an orange-yellow oil.

b-Methyl (Z)-3-(2-butoxy-3'-methylaminobiphenyl-4-yl)-2-methoxyacrylate

In a manner similar to that of Example 25c, 4 mg (0.018 mmol) of palladium acetate and then 13 mg (0.036 mmol) of 2-(dicyclohexylphosphino)biphenyl are added to a mixture of 0.7 g (1.8 mmol) of methyl (Z)-3-(3-butoxy-4-iodophenyl)-2-methoxyacrylate prepared as in Example 24c, 0.5 g (2.15 mmol) of methyl[3-(4,4,5,5-tetramethyl[1.3.2]dioxaborolan-2-yl)phenyl]amine and 1.8 mL of aqueous 2M potassium phosphate solution in 10 mL of dimethylformamide. The reaction mixture is heated at 90-95° C. for 1 hour. The reaction medium is hydrolyzed with saturated aqueous ammonium chloride solution and extracted with ethyl acetate. The organic phases are combined, washed with saturated sodium chloride solution and dried over magnesium sulfate. The solvent is evaporated off and the residue is purified by chromatography on a column of silica eluted with a 60/40 heptane/ethyl acetate mixture. 0.5 g (71%) of methyl (Z)-3-(2-butoxy-3'-methylaminobiphenyl-4-yl)-2-methoxyacrylate are obtained.

c-Methyl (Z)-3-{2-butoxy-3'-[methyl(4-nitrophenoxycarbonyl)amino]biphenyl-4-yl]-2-methoxyacrylate 0.3 g (1.5 mmol) of 4-nitrophenyl chloroformate and then 0.3 mL (1.5 mmol) of diisopropylethylamine are added to a solution of 0.5 g (1.3 mmol) of methyl (Z)-3-(2-butoxy-3'-methylaminobiphenyl-4-yl)-2-methoxyacrylate in 8 mL of dichloromethane. The reaction mixture is stirred for 45 minutes at room temperature.

The reaction is stopped by addition of 15 mL of water and extraction with dichloromethane. The organic phases are combined, washed with water and then dried over magnesium sulfate. After evaporating off the solvents, 0.8 g (100%) of methyl (Z)-3-[2-butoxy-3'-[methyl-(4-nitrophenoxycarbonyl)amino]biphenyl-4-yl]-2-methoxyacrylate are obtained in the form of a yellow oil. The crude product obtained is used directly in the following step.

d-Methyl (Z)-3-[2-butoxy-3'-(3-butyl-1-methylureido)biphenyl-4-yl]-2-methoxyacrylate 0.075 mL (0.75 mmol) of n-butylamine is added to a solution of 0.4 g (0.6 mmol) of methyl (Z)-3-{2-butoxy-3'-[methyl-(4-nitrophenoxycarbonyl)amino]biphenyl-4-yl}-2-methoxyacrylate in 5 mL of dimethylformamide. The reaction mixture is rapidly placed in an oil bath preheated to 80° C. and then stirred at 80° C. for 3 hours. After cooling, the reaction is stopped by addition of 10 mL of water and extraction with ethyl acetate. The organic phases are combined, washed with saturated sodium chloride solution and then dried over magnesium sulfate. The solvents are evaporated off. The crude product obtained is purified by chromatography on a column of silica eluted with a 70/30 heptane/ethyl acetate mixture to give 0.2 g (67%) of methyl (Z)-3-[2-butoxy-3'-(3-butyl-1-methylureido)biphenyl-4-yl]-2-methoxyacrylate in the form of a colorless oil.

e-(Z)-3-[2-butoxy-3'-(1-methyl-3-butylureido)biphenyl-4-yl]-2-methoxyacrylic acid 0.65 mL (0.65 mmol) of aqueous 1 M sodium hydroxide solution is added to a solution of 0.2 g (0.43 mmol) of methyl (Z)-3-[2-butoxy-3'-(1-methyl-3-butylureido)biphenyl-4-yl]-2-methoxyacrylate in 5 mL of tetrahydrofuran. The reaction mixture is stirred at 68° C. for 5 hours. After cooling, the reaction is stopped by addition of 1 mL aqueous 1 M hydrochloric acid solution and 10 mL of water and extraction with ethyl acetate. The organic phases are combined, washed with saturated sodium chloride solution and then dried over magnesium sulfate. The solvents are evaporated off. The product is recrystallized from a pentane/acetone mixture to give 0.12 g (63%) of (Z)-3-[2-butoxy-3'-(1-methyl-3-butylureido)biphenyl-4-yl]-2-methoxyacrylic acid in the form of a white solid with a melting point of 106° C.

$^1$H NMR (δ, CDCl$_3$): 0.71 (t, J=7.1-Hz, 3H); 0.77 (t, J=6.9-Hz, 3H); 1.07-1.14 (m, 2H); 1.20-1.30 (m, 4H); 1.55-1.62 (m, 2H); 3.02 (m, 2H); 3.15 (s, 3H); 3.70 (s, 3H); 3.87 (t, J=6.5-Hz, 2H); 4.27 (m, 1H); 6.99 (s, 1H); 7.05 (d, J=6.1-Hz, 1H); 7.18 (d, J=7.8-Hz, 1H); 7.24 (d, J=8.0-Hz, 1H); 7.28-7.36 (m, 4H).

EXAMPLE 29

Synthesis of (Z)-3-[2-butoxy-3'-(3-butyl-1-methylureido)biphenyl-4-yl]-2-ethoxyacrylic acid

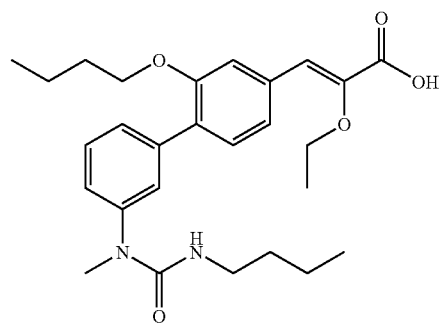 [SMILES: CCCCNC(=O)N(C)c1cccc(-c2ccc(/C=C(\OCC)C(=O)O)cc2OCCCC)c1]

a-Methyl (Z)-3-[2-butoxy-3'-(3-butyl-1-methylureido)biphenyl-4-yl]-2-ethoxyacrylate In a manner similar to that of Example 23d, starting with 40 mg (0.1 mmol) of methyl (Z)-3-(2-butoxy-3'-methylaminobiphenyl-4-yl)-2-ethoxyacrylate prepared as described in Example 23c and 11 mg (0.11 mmol) of butyl isocyanate, 30 mg (59%) of methyl (Z)-3-[2-butoxy-3'-(3-butyl-1-methylureido)biphenyl-4-yl]-2-ethoxyacrylate are obtained after purification.

b-(Z)-3-[2-butoxy-3'-(3-butyl-1-methyl ureido)biphenyl-4-yl]-2-ethoxyacrylic acid In a manner similar to that of Example 191, starting with 30 mg (0.06 mmol) of methyl (Z)-3-[2-butoxy-3'-(3-butyl-1-methylureido)biphenyl-4-yl]-2-ethoxyacrylate, 20 mg (60%) of (Z)-3-[2-butoxy-3'-(3-butyl-1-methylureido)biphenyl-4-yl]-2-ethoxyacrylic acid are obtained.

$^1$H NMR (δ, CDCl$_3$): 0.79 (t, J=7.3-Hz, 3H); 0.86 (t, J=7.4-Hz, 3H); 1.20 (m, 2H); 1.32-1.38 (m, 7H); 1.68 (m, 2H); 3.12 (dd, J=6.9-Hz, J=5.6-Hz, 2H); 3.23 (s, 3H); 3.96 (t, J=6.5-Hz, 2H); 4.03 (q, J=7.4-Hz, 2H); 4.36 (t, J=5.6-Hz, 1H); 7.07 (s, 1H); 7.13 (m, 1H); 7.15 (m, 1H); 7.20 (m, 1H); 7.26-7.44 (m, 3H); 7.55 (s, 1H).

EXAMPLE 30

Synthesis of (Z)-3-[2-butoxy-3'-(3-cyclohexyl-1-methylureido)biphenyl-4-yl]-2-ethoxyacrylic acid

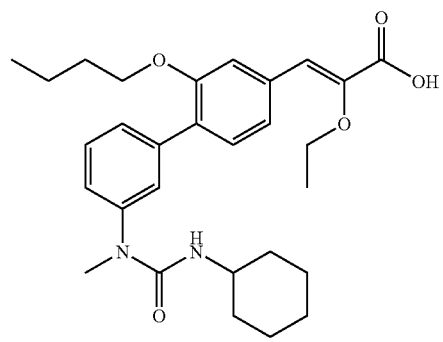 [SMILES: CCCCOc1cc(/C=C(\OCC)C(=O)O)ccc1-c1cccc(N(C)C(=O)NC2CCCCC2)c1]

a-Methyl (Z)-3-[2-butoxy-3'-(3-cyclohexyl-1-methylureido)biphenyl-4-yl]-2-ethoxyacrylate In a manner similar to that of Example 23d, starting with 40 mg (0.1 mmol) of methyl (Z)-3-(2-butoxy-3'-methylaminobiphenyl-4-yl)-2-ethoxyacrylate and 14 mg (0.11 mmol) of cyclohexyl isocyanate, 33 mg (60%) of methyl (Z)-3-[2-butoxy-3'-(3-cyclohexyl-1-methylureido)biphenyl-4-yl]-2-ethoxyacrylate are obtained after purification.

b-(Z)-3-[2-butoxy-3'-(3-cyclohexyl-1-methylureido)biphenyl-4-yl]-2-ethoxyacrylic acid In a manner similar to that of Example 191, starting with 33 mg (0.06 mmol) of methyl (Z)-3-[2-butoxy-3'-(3-cyclohexyl-1-methylureido)biphenyl-4-yl]-2-ethoxyacrylate, 20 mg (65%) of (Z)-3-[2-butoxy-3'-(3-cyclohexyl-1-methylureido)biphenyl-4-yl]-2-ethoxyacrylic acid are obtained.
$^1$H NMR (δ, CDCl$_3$): 0.85 (t, J=7.4-Hz, 3H); 0.90 (m, 2H); 1.28 (m, 2H); 1.35 (m, 2H); 1.37 (t, J=7-Hz, 3H); 1.40-1.51 (m, 4H); 1.68 (m, 2H); 1.80 (m, 2H); 3.23 (s, 3H); 3.60 (m, 1H); 3.96 (t, J=6.5-Hz, 2H); 4.03 (q, J=7.4-Hz, 2H); 4.22 (d, J=8-Hz, 1H); 7.08 (s, 1H); 7.13 (d, J=6.1-Hz, 1H); 7.14 (s, 1H); 7.19-7.27 (m, 2H); 7.35-7.44 (m, 2H); 7.55 (s, 1H).

EXAMPLE 31

Synthesis of (E)-3-[3'-(3-heptyl-1-methylureido)-2-propoxybiphenyl-4-yl]-2-methylacrylic acid

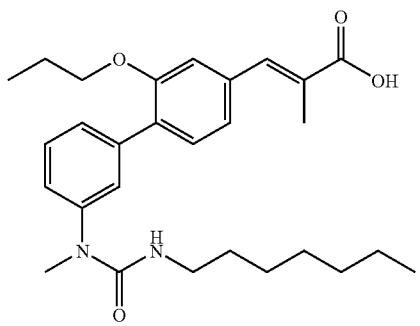 [SMILES: CCCCCCCNC(=O)N(C)c1cccc(-c2ccc(/C=C(\C)C(=O)O)cc2OCCC)c1]

a-Methyl 4-iodo-3-propoxybenzoate 1.3 mL (13.4 mmol) of propyl iodide are added to a solution of 2.5 g (9 mmol) of methyl 3-hydroxy-4-iodobenzoate in 15 mL of methyl ethyl ketone in the presence of 3 g (22 mmol) of potassium carbonate. The reaction medium is stirred for 5 hours at 80° C. After cooling and adding water, the medium is extracted with ethyl acetate. The organic phase is dried over magnesium sulfate, filtered and evaporated. The residue obtained is used in the following step without further purification.

b-(4-Iodo-3-propoxyphenyl)methanol 0.6 g (22 mmol) of sodium borohydride is added to a solution of methyl 4-iodo-3-propoxybenzoate in 15 mL of tetrahydrofuran. The reaction medium is stirred for 12 hours at 60° C. After cooling and adding saturated ammonium chloride solution, the reaction medium is extracted with ethyl acetate. The organic phase is dried over magnesium sulfate, filtered and evaporated. The residue obtained is used in the following step without further purification.

c-4-Iodo-3-propoxybenzaldehyde

The (4-iodo-3-propoxyphenyl)methanol is dissolved in 30 mL of dichloromethane and 3.9 g (45 mmol) of manganese oxide are added. The reaction medium is stirred for 12 hours at room temperature. After filtering off the solid through Celite, the filtrate is evaporated under vacuum. The residue obtained is purified by chromatography on a column of silica eluted with a 9/1 heptane/ethyl acetate mixture. 1.5 g (57% yield for the three steps a-c) of 4-iodo-3-propoxybenzaldehyde are obtained.

d-Ethyl (E)-3-(4-iodo-3-propoxyphenyl)-2-methylacrylate

A solution of 1.8 g (7.7 mmol) of triethyl 2-phosphonopropionate in 25 mL of tetrahydrofuran is added to a suspension of 310 mg (7.7 mmol) of 60% sodium hydride in oil, precooled to 0° C. After stirring at 0° C. for 15 minutes, a solution of 1.5 g (5.2 mmol) of 4-iodo-3-propoxybenzaldehyde in 10 mL of tetrahydrofuran is added. The reaction medium is stirred at room temperature for 12 hours. Saturated ammonium chloride solution is added and the reaction medium is extracted with ethyl acetate. The organic phase is dried over magnesium sulfate, filtered and evaporated. The residue obtained is purified by chromatography on a column of silica eluted with a 7/3 heptane/ethyl acetate mixture. 1.6 g (84%) of ethyl (E)-3-(4-iodo-3-propoxyphenyl)-2-methylacrylate are obtained.

e-3-Methylaminophenylboronic acid 161 mL (242 mmol) of 1.5M methyllithium in diethyl ether are added dropwise to a solution precooled to −78° C. of 37.6 g (202 mmol) of (3-bromophenyl)methylamine (prepared according to Example 24f) in 300 mL of tetrahydrofuran. After stirring for 1 hour at −78° C., 261 mL (444 mmol) of a 1.7M solution of tert-butyllithium in pentane are added dropwise and the medium is again stirred at −78° C. for 1 hour. At −65° C., 103.5 mL (808 mmol) of trimethyl borate are added dropwise and the reaction medium is then stirred, while allowing the temperature to rise to room temperature over 1 hour. After addition of ice, the reaction medium is extracted with a 1/1 heptane/ethyl acetate mixture and then with 1-butanol. The organic phases are combined, washed with water, dried over magnesium sulfate, filtered and evaporated; 11 g (40%) of 3-methylaminophenylboronic acid are obtained.

f-Ethyl (E)-2-methyl-3-(3'-methylaminobiphenyl-4-yl)acrylate 1.6 g (4.3 mmol) of ethyl (E)-3-(4-iodo-3-propoxyphenyl)-2-methylacrylate are dissolved in 10 mL of a 4/1v/v mixture of dimethylformamide and of aqueous 2 M potassium phosphate solution. 0.9 g (5.7 mmol) of 3-methylaminophenylboronic acid prepared as described in Example 31e, 58 mg (0.2 mmol) of palladium acetate and 152 mg (0.4 mmol) of dicyclohexylbiphenylphosphine are added. The mixture is stirred for 3 hours at 90° C. After cooling and adding water, the medium is extracted with ethyl acetate. The organic phase is washed with saturated sodium chloride solution, dried over sodium sulfate, filtered and evaporated. The residue obtained is purified by chromatography on a column of silica eluted with an 8/2 heptane/ethyl acetate mixture. 1.0 g (65%) of ethyl (E)-2-methyl-3-(3'-methylaminobiphenyl-4-yl)acrylate is obtained.

g-Ethyl (E)-3-[3'-(3-heptyl-1-methylureido)biphenyl-4-yl]-2-methylacrylate 1.0 g (3.4 mmol) of ethyl (E)-2-methyl-3-(3'-methylaminobiphenyl-4-yl)acrylate is mixed with 2 mL of heptyl isocyanate and the medium is irradiated by microwave for 30 minutes at a temperature of 100° C. in an Emrys Optimizer machine. The residue obtained is purified by chromatography on a column of silica eluted with a 9/1 heptane/ethyl acetate mixture. 1.2 g (88%) of ethyl (E)-3-[3'-(3-heptyl-1-methylureido)biphenyl-4-yl]-2-methylacrylate are obtained.

h-(E)-3-[3'-(3-heptyl-1-methylureido)biphenyl-4-yl]-2-methylacrylic acid 1.5 g (2.5 mmol) of sodium hydroxide are added to a solution of 1.2 g (2.5 mmol) of ethyl (E)-3-[3'-(3-heptyl-1-methylureido)biphenyl-4-yl]-2-methylacrylate in 30 mL of an 8/2 tetrahydrofuran/methanol mixture. The reaction medium is stirred at room temperature for 4 hours. After addition of water and acidification to pH4 with acetic acid, the reaction medium is extracted with ethyl acetate. The organic phase is washed with saturated sodium chloride solution, dried over sodium sulfate, filtered and evaporated. The residue obtained is purified by chromatography on a column of silica eluted with a 7/3 heptane/ethyl acetate mixture. The product is recrystallized from an isopropyl ether/pentane mixture. 456 mg (40%) of (E)-3-[3'-(3-heptyl-1-methylureido)biphenyl-4-yl]-2-methylacrylic acid are obtained in the form of a solid with a melting point of 79° C.

$^1$H NMR (CDCl$_3$, 400 MHz): 0.85 (t, J=7.2-Hz, 3H); 1.12-1.23 (m, 8H); 1.42-1.55 (m, 7H); 2.20 (s, 3H); 3.18 (m, 2H); 3.27 (s, 3H); 4.09 (q, J=7-Hz, 2H); 4.39 (t, J=5.4-Hz, 1H); 7.24 (m, 1H); 7.49-7.65 (m, 6H); 7.85 (s, 1H); 10.70 (s, 1H).

EXAMPLE 32

Synthesis of (E)-3-[2-ethoxy-3'-(3-heptyl-1-methylureido)biphenyl-4-yl]-2-methylacrylic acid

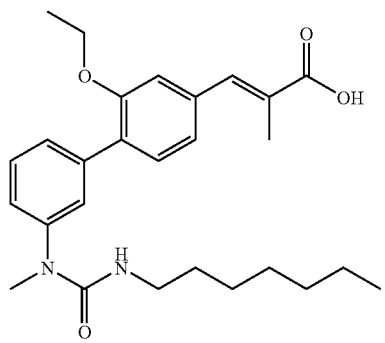 [SMILES: CCCCCCCNC(=O)N(C)c1cccc(-c2ccc(/C=C(\C)C(=O)O)cc2OCC)c1]

a-Ethyl (E)-3-(3-ethoxy-4-hydroxyphenyl)-2-methylacrylate

A solution of 6.3 g (26.4 mmol) of 2-triethyl phosphonopropionate in 15 mL of tetrahydrofuran is added to a mixture of 1 g (26.4 mmol) of sodium hydride in 10 mL of tetrahydrofuran at 0° C. The reaction medium is stirred for 15 minutes. A solution of 1.9 g (11.5 mmol) of 3-ethoxy-4-hydroxybenzaldehyde in 10 mL of tetrahydrofuran is then added to the reaction mixture and the medium is stirred at room temperature for 18 hours. The reaction medium is poured into saturated ammonium chloride solution and then acidified with 2 N hydrochloric acid solution and extracted with ethyl acetate. The organic phases are combined, washed with water and dried over sodium sulfate. The solvent is evaporated off and the residue (5.2 g) is purified by chromatography on a column of silica eluted with an 80/20 heptane/ethyl acetate mixture. 2.0 g (72%) of ethyl (E)-3-(3-ethoxy-4-hydroxyphenyl)-2-methylacrylate are obtained in the form of yellow crystals.

b-Ethyl (E)-3-(3-ethoxy-4-trifluoromethanesulfonyloxyphenyl)-2-methylacrylate 0.8 mL (4.8 mmol) of triflic anhydride is added to a solution of 1.5 g (4 mmol) of ethyl (E)-3-(3-ethoxy-4-hydroxyphenyl)-2-methylacrylate and 1.6 mL (12 mmol) of triethylamine in 20 mL of dichloromethane at 0° C. The reaction mixture is stirred at room temperature for 1 hour. The medium is hydrolyzed in sodium hydrogen carbonate solution and extracted with ethyl acetate. The organic phases are combined, washed with water and dried over magnesium sulfate. The solvent is evaporated off and 1.65 g (100%) of ethyl (E)-3-(3-ethoxy-4-trifluoromethanesulfonyloxyphenyl)-2-methylacrylate are obtained in the form of a brown oil.

c-Ethyl (E)-3-(2-ethoxy-3'-methylaminobiphenyl-4-yl)-2-methylacrylate 45 mg (0.2 mmol) of palladium acetate and then 140 mg (0.4 mmol) of 2-(dicyclohexylphosphino)biphenyl are added to a mixture of 1.65 g (4 mmol) of ethyl (E)-3-(3-ethoxy-4-trifluoromethanesulfonyloxyphenyl)-2-methylacrylate, 1.1 g (4.8 mmol) of methyl[3-(4,4,5,5-tetramethyl[1.3.2]dioxaborolan-2-yl)phenyl]amine (prepared as described in Example 28a) and 2 mL of aqueous 2 M potassium phosphate solution in 8 mL of dimethylformamide. The reaction mixture is heated at 90-95° C. for 4 hours. The medium is hydrolyzed with saturated ammonium chloride solution and extracted with ethyl acetate. The organic phases are combined, washed with saturated sodium chloride solution and dried over sodium sulfate. The solvent is evaporated off and the brown oil obtained (2.7 g) is purified by chromatography on a column of silica eluted with a 90/10 heptane/ethyl acetate mixture. 346 mg (17%) of ethyl (E)-3-(2-ethoxy-3' methylaminobiphenyl-4-yl)-2-methylacrylate are obtained in the form of a yellow oil.

d-Ethyl (E)-3-[2-ethoxy-3'-(3-heptyl-1-methylureido)biphenyl-4-yl]-2-methylacrylate 280 μL (1.7 mmol) of heptyl isocyanate are added to 340 mg (0.7 mmol) of ethyl (E)-3-(2-ethoxy-3'-methylaminobiphenyl-4-yl)-2-methylacrylate. The reaction mixture is heated at 100° C. in an Emrys Optimizer microwave machine for 20 minutes. The residue is purified by chromatography on a column of silica eluted with an 80/20 heptane/ethyl acetate mixture. 363 mg (100%) of ethyl (E)-3-[2-ethoxy-3'-(3-heptyl-1-methylureido)biphenyl-4-yl]-2-methylacrylate are obtained in the form of a yellowish oil.

e-(E)-3-[2-ethoxy-3'-(3-heptyl-1-methylureido)biphenyl-4-yl]-2-methylacrylic acid 297 mg (7.4 mmol) of sodium hydroxide are added to a solution of 357 mg (0.74 mmol) of ethyl (E)-3-[2-ethoxy-3'-

(3-heptyl-1-methylureido)biphenyl-4-yl]-2-methylacrylate in 15 mL of ethanol. The reaction mixture is heated at 50° C. for 3 hours. After cooling, the medium is evaporated to dryness, taken up in water, acidified with 2 N hydrochloric acid solution and extracted with ethyl acetate. The organic phases are combined, washed with water, dried over magnesium sulfate and filtered. The solvent is evaporated off and the solid obtained is taken up in a mixture of ethyl ether and pentane, filtered and dried. 250 mg (75%) of (E)-3-[2-ethoxy-3'-(3-heptyl-1-methylureido)biphenyl-4-yl]-2-methylacrylic acid are obtained in the form of a white powder with a melting point of 123° C.

$^1$H NMR (CDCl$_3$, 400 MHz): 0.85 (t, 3H); 1.22-1.28 (m, 8H); 1.39 (m, 2H+3H); 2.21 (s, 3H); 3.17 (q, 2H); 3.31 (s, 3H); 4.09 (q, 2H); 4.46 (t, 1H); 7.03 (s, 1H); 7.15 (d, 1H); 7.22 (d, 1H); 7.37 (d, 1H); 7.46-7.52 (m, 3H); 7.83 (s, 1H).

EXAMPLE 33

Synthesis of 2-[1-[2-ethoxy-3'-(3-heptyl-1-methylureido)biphenyl-4-yl]meth-(E)-ylidene]butyric acid

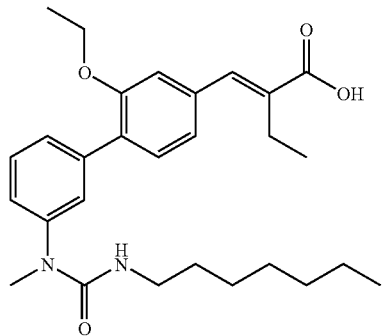 [SMILES: CCCCCCCNC(=O)N(C)c1cccc(-c2ccc(/C=C(\CC)C(=O)O)cc2OCC)c1]

a-Ethyl 2-[1-(3-ethoxy-4-hydroxyphenyl)meth-(E)-ylidene]butyrate

A solution of 11.8 g (46 mmol) of triethyl 2-phosphonobutyrate in 20 mL of tetrahydrofuran is added to a mixture of 1.8 g (46 mmol) of sodium hydride in 20 mL of tetrahydrofuran at 0° C. The reaction medium is stirred for 15 minutes. A solution of 3.4 g (20 mmol) of 3-ethoxy-4-hydroxybenzaldehyde prepared as in Example 32a in 20 mL of tetrahydrofuran is then added to the reaction mixture and the reaction medium is stirred at room temperature for 3 days. The reaction medium is then poured into saturated ammonium chloride solution, acidified with aqueous 2 N hydrochloric acid solution and extracted with ethyl acetate. The organic phases are combined, washed with water and dried over sodium sulfate. The solvent is evaporated off and the residue (12.5 g) is purified by chromatography on a column of silica eluted with an 80/20 heptane/ethyl acetate mixture. 3.7 g (71%) of ethyl 2-[1-(3-ethoxy-4-hydroxyphenyl)meth-(E)-ylidene]butyrate are obtained in the form of a yellow oil.

b-Ethyl 2-[1-(3-ethoxy-4-trifluoromethanesulfonyloxyphenyl)meth-(E)-ylidene]butyrate 808 µL (4.8 mmol) of triflic anhydride are added to a solution of 1.5 g (4 mmol) of ethyl 2-[1-(3-ethoxy-4-hydroxyphenyl)meth-(E)-ylidene]butyrate and 1.6 mL (12 mmol) of triethylamine in 20 mL of dichloromethane at 0° C. The reaction mixture is stirred at room temperature for 1 hour. The reaction medium is hydrolyzed in sodium hydrogen carbonate solution and extracted with ethyl acetate. The organic phases are combined, washed with water and dried over magnesium sulfate. The solvent is evaporated off and 1.7 g (100%) of ethyl 2-[1-(3-ethoxy-4-trifluoromethanesulfonyloxyphenyl)meth-(E)-ylidene]butyrate are obtained in the form of a brown oil.

c-Ethyl 2-[1-(2-ethoxy-3'-methylaminobiphenyl-4-yl)meth-(E)-ylidene]butyrate 45 mg (0.2 mmol) of palladium acetate and then 140 mg (0.4 mmol) of 2-(dicyclohexylphosphino)biphenyl are added to a mixture of 1.7 g (4 mmol) of ethyl 2-[1-(3-ethoxy-4-trifluoromethanesulfonyloxyphenyl)meth-(E)-ylidene]butyrate, 1.1 g (4.8 mmol) of methyl[3-(4,4,5,5-tetramethyl[1.3.2]dioxaborolan-2-yl)phenyl]amine (prepared according to Example 28a) and 2 mL of aqueous 2 M potassium phosphate solution in 8 mL of dimethylformamide. The reaction mixture is heated at 90-95° C. for 3 hours. The reaction medium is hydrolyzed in saturated ammonium chloride solution and extracted with ethyl acetate. The organic phases are combined, washed with saturated sodium chloride solution and dried over sodium sulfate. The solvent is evaporated off and the brown oil obtained (2.3 g) is purified by chromatography on a column of silica eluted with a 90/10 heptane/ethyl acetate mixture. 526 mg (15%) of ethyl 2-[1-(2-ethoxy-3'-methylaminobiphenyl-4-yl)meth-(E)-ylidene]butyrate are obtained in the form of a yellow oil.

d-Ethyl 2-[1-[2-ethoxy-3'-(3-heptyl-1-methylureido) biphenyl-4-yl]meth-(E)-ylidene]butyrate 470 µL (2.9 mmol) of heptyl isocyanate are added to 520 mg (0.6 mmol) of crude ethyl 2-[1-(2-ethoxy-3'-methylaminobiphenyl-4-yl)meth-(E)-ylidene]butyrate. The reaction mixture is heated at 100° C. in an Emrys Optimizer microwave machine for 20 minutes. The residue is purified by chromatography on a column of silica eluted with an 80/20 heptane/ethyl acetate mixture. 622 mg (100%) of ethyl 2-[1-[2-ethoxy-3'-(3-heptyl-1-methylureido)biphenyl-4-yl]meth-(E)-ylidene]butyrate are obtained in the form of a yellowish oil.

e-2-[1-[2-ethoxy-3'-(3-heptyl-1-methylureido)biphenyl-4-yl]meth-(E)-ylidene]butyric acid 249 mg (6.2 mmol) of sodium hydroxide are added to a solution of 616 mg (0.65 mmol) of ethyl 2-[1-[2-ethoxy-3'-(3-heptyl-1-methylureido)biphenyl-4-yl]meth-(E)-ylidene]butyrate in 15 mL of ethanol. The reaction mixture is heated at 50° C. for 3 hours. The reaction medium is evaporated to dryness, taken up in water and extracted with ethyl acetate. The aqueous phase is acidified with aqueous 2 N hydrochloric acid solution and extracted with ethyl acetate. The organic phases are combined, washed with water and dried over magnesium sulfate. The solvent is evaporated off and the oil obtained is purified by chromatography on a column of silica eluted with a 50/50 heptane/ethyl acetate mixture. 222 mg (77%) of 2-[1-[2-ethoxy-3'-(3-heptyl-1-methylureido)biphenyl-4-yl]meth-(E)-ylidene]butyric acid are obtained in the form of a yellowish oil.

$^1$H NMR (CDCl$_3$, 400 MHz): 0.86 (m, 3H); 1.22-1.28 (m, 8H); 1.38-1.45 (m, 2H+3H); 2.64 (q, 2H); 3.17 (q, 2H); 3.31

(s, 3H); 4.08 (q, 2H); 4.44 (t, 1H); 7.02 (s, 1H); 7.10 (d, 1H); 7.21 (d, 1H); 7.37 (d, 1H); 7.44-7.52 (m, 3H); 7.79 (s, 1H).

EXAMPLE 34

Synthesis of (E)-3-[2-butoxy-3'-(1-methyl-3-pentylureido)biphenyl-4-yl]-2-methylacrylic acid

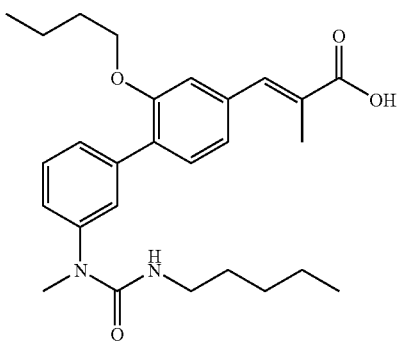 [SMILES: CCCCCNC(=O)N(C)c1cccc(-c2ccc(/C=C(\C)C(=O)O)cc2OCCCC)c1]

a-Ethyl (E)-3-[2-butoxy-3'-(1-methyl-3-pentylureido)biphenyl-4-yl]-2-methylacrylate 3 mg (0.013 mmol) of palladium acetate and then 9 mg (0.026 mmol) of 2-(dicyclohexylphosphino)biphenyl are added to a mixture of 505 mg (1.3 mmol) of ethyl (E)-3-(3-butoxy-4-iodophenyl)-2-methylacrylate prepared as described in Example 19h, 446 mg (1.7 mmol) of 3-(1-methyl-3-pentylureido)phenylboronic acid prepared as described in Example 24h and 1.3 mL of aqueous 2 M potassium phosphate solution in 6.5 mL of dimethylformamide. The reaction mixture is heated at 90-95° C. for 2 hours. The reaction medium is hydrolyzed in saturated aqueous ammonium chloride solution and extracted with ethyl acetate. The organic phases are combined, washed with saturated aqueous sodium chloride solution and dried over magnesium sulfate. After filtration, the solvent is evaporated off and the brown oil obtained (1.5 g) is purified by chromatography on a column of silica eluted with a 70/30 heptane/ethyl acetate mixture. 533 mg (85%) of ethyl (E)-3-[2-butoxy-3'-(1-methyl-3-pentylureido)biphenyl-4-yl]-2-methylacrylate are obtained.

b-(E)-3-[2-butoxy-3'-(1-methyl-3-pentylureido)biphenyl-4-yl]-2-methylacrylic acid 40 mg (1 mmol) of sodium hydroxide are added to a solution of 526 mg (1.1 mmol) of ethyl (E)-3-[2-butoxy-3'-(1-methyl-3-pentylureido)biphenyl-4-yl]-2-methylacrylate in 1 mL of ethanol and 10 mL of tetrahydrofuran. The reaction mixture is heated at 50° C. for 24 hours. The reaction medium is evaporated to dryness, taken up in water and acidified with aqueous 2 N hydrochloric acid solution and extracted with ethyl acetate. The organic phases are combined, washed with water and dried over magnesium sulfate. After filtration, the solvent is evaporated off and the oil obtained is purified by chromatography on a column of silica eluted with a 60/40 heptane/ethyl acetate mixture and then precipitated from heptane. 310 mg (91%) of (E)-3-[2-butoxy-3'-(1-methyl-3-pentylureido)biphenyl-4-yl]-2-methylacrylic acid are obtained in the form of a white solid with a melting point of 87-89° C.

$^1$H NMR (CDCl$_3$, 400 MHz): 0.84 (t, 3H); 0.93 (t, 3H); 1.22-1.28 (m, 4H); 1.39-1.46 (m, 4H); 1.74 (m, 2H); 2.21 (s, 3H); 3.17 (q, 2H); 3.31 (s, 3H); 4.01 (t, 2H); 4.42 (t, 1H); 7.03 (s, 1H); 7.13 (d, 1H); 7.21 (d, 1H); 7.37 (d, 1H); 7.44-7.51 (m, 3H); 7.83 (s, 1H).

EXAMPLE 35

Synthesis of (E)-3-[2-butoxy-3'-(3-heptyl-1-methylureido)biphenyl-4-yl]-2-methylacrylic acid

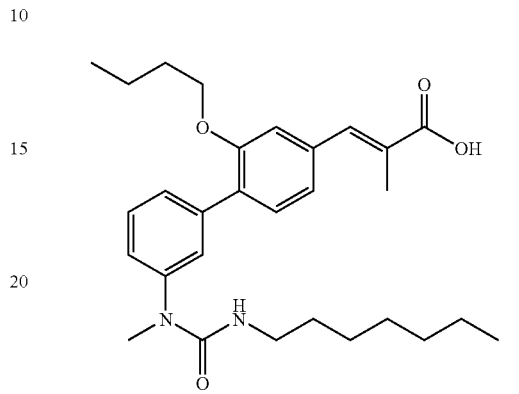

a-1-(3-bromophenyl)-3-heptyl-1-methylurea 3.2 mL (20 mmol) of heptyl isocyanate are added to a solution of 2.5 g (13 mmol) of (3-bromophenyl)methylamine (prepared according to Example 24f) in 10 mL of tetrahydrofuran in the presence of 2 mL of triethylamine. The reaction mixture is stirred for 12 hours at room temperature. The reaction is stopped by addition of 2 mL of water and extraction with ethyl acetate. The organic phases are combined and dried over sodium sulfate. The solvents are evaporated off and the residue is then purified by chromatography on a column of silica eluted with a 70/30 heptane/ethyl acetate mixture. 3.4 g (77%) of 1-(3-bromophenyl)-3-heptyl-1-methylurea are obtained in the form of a solid.

b-3-heptyl-1-methyl-1-[3-(4,4,5,5-tetramethyl[1.3.2]dioxaborolan-2-yl)phenyl]urea:

4.0 g (15.5 mmol) of bis-pinacoldiborane are added to a mixture of 3.4 g (10 mmol) of 1-(3-bromophenyl)-3-heptyl-1-methylurea and 3.0 g (31 mmol) of potassium acetate in the presence of 380 mg (0.5 mmol) of diphenylphosphinoferrocenepalladium dichloride in 15 mL of dimethylformamide. The mixture is stirred for 3 hours at 90° C. The reaction is stopped by addition of 50 mL of water and extraction with ethyl acetate. The organic phases are combined and dried over sodium sulfate. The solvents are evaporated off and the residue is then purified by chromatography on a column of silica eluted with a 70/30 heptane/ethyl acetate mixture. 2.5 g (64%) of 3-heptyl-1-methyl-1-[3-(4,4,5,5-tetramethyl[1.3.2]dioxaborolan-2-yl)phenyl]urea are obtained in the form of an oil.

c-Ethyl (E)-3-[2-butoxy-3'-(3-heptyl-1-methylureido)biphenyl-4-yl]-2-methylacrylate In a manner similar to that of Example 34a, 3 mg (0.013 mmol) of palladium acetate and then 9 mg (0.026 mmol) of 2-(dicyclohexylphosphino)biphenyl are added to a mixture of 505 mg (1.3 mmol) of ethyl (E)-3-(3-butoxy-4-iodophenyl)-2-methylacrylate prepared as described in Example 19h, 494 mg (1.7 mmol) of 3-heptyl-1-methyl-1-[3-(4,4,5,5-tetramethyl[1.3.2]dioxaborolan-2-yl)phenyl]urea and 1.3 mL of aqueous 2 M potassium phosphate solution in 6.5 mL of dimethylformamide. The reaction mixture is heated at 90-95° C. for 2 hours. The reaction medium is hydrolyzed with saturated aqueous ammonium chloride solution and extracted with ethyl acetate. The organic phases are combined, washed with saturated sodium chloride solution and dried over magnesium sulfate. The solvent is evaporated off and the brown oil obtained (1.3 g) is purified by chromatography on a column of silica eluted with a 70/30 heptane/ethyl acetate mixture. 558 mg (84%) of ethyl (E)-3-[2-butoxy-3'-(3-heptyl-1-methyl-ureido)biphenyl-4-yl]-2-methylacrylate are obtained.

d-(E)-3-[2-butoxy-3'-(3-heptyl-1-methylureido)biphenyl-4-yl]-2-methylacrylic acid 40 mg (1.1 mmol) of sodium hydroxide are added to a solution of 552 mg (1.1 mmol) of ethyl (E)-3-[2-butoxy-3'-(1-methyl-3-heptylureido)biphenyl-4-yl]-2-methylacrylate in 1 mL of ethanol and 10 mL of tetrahydrofuran. The reaction mixture is heated at 50° C. for 24 hours. The reaction medium is evaporated to dryness, taken up in water and acidified with aqueous 2 N hydrochloric acid solution and extracted with ethyl acetate. The organic phases are combined, washed with water and dried over magnesium sulfate. After filtration, the solvent is evaporated off and the oil obtained is purified by chromatography on a column of silica eluted with a 60/40 heptane/ethyl acetate mixture and then precipitated from heptane. 387 mg (85%) of (E)-3-[2-butoxy-3'-(1-methyl-3-heptylureido)biphenyl-4-yl]-2-methylacrylic acid are obtained in the form of a white powder with a melting point of 70-72° C.

$^1$H NMR (CDCl$_3$, 400 MHz): 0.84 (t, 3H); 0.93 (t, 3H); 1.22 (m, 8H); 1.40-1.46 (m, 4H); 1.70-1.77 (m, 2H); 2.21 (s, 3H); 3.17 (q, 2H); 3.31 (s, 3H); 4.01 (t, 2H); 4.41 (t, 1H); 7.03 (s, 1H); 7.13 (d, 1H); 7.21 (d, 1H); 7.37 (d, 1H); 7.44-7.51 (m, 3H); 7.83 (s, 1H).

EXAMPLE 36

Synthesis of 2-[1-[2-butoxy-3'-(1-methyl-3-pentylureido)biphenyl-4-yl]meth-(E)-ylidene]butyric acid

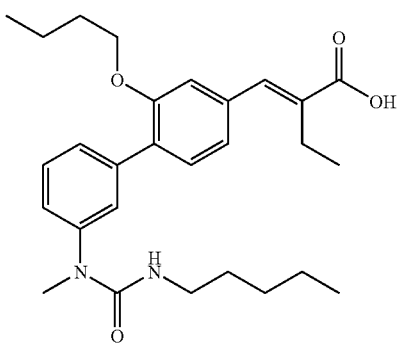 [SMILES: CCCCCNC(=O)N(C)c1cccc(-c2ccc(/C=C(\CC)C(=O)O)cc2OCCCC)c1]

a-Ethyl 2-[1-[2-butoxy-3'-(1-methyl-3-pentylureido)biphenyl-4-yl]meth-(E)-ylidene]butyrate:L 3 mg (0.013 mmol) of palladium acetate and then 9 mg (0.026 mmol) of 2-(dicyclohexylphosphino)biphenyl are added to a mixture of 523 mg (1.3 mmol) of ethyl 2-[1-(3-butoxy-4-iodophenyl)meth-(E)-ylidene]butyrate (prepared according to Example 22a), 446 mg (1.7 mmol) of 3-(1-methyl-3-pentylureido)phenylboronic acid (prepared according to Example 24h) and 1.3 mL of aqueous 2 M potassium phosphate solution in 6.5 mL of dimethylformamide. The reaction mixture is heated at 90-95° C. for 2 hours. The reaction medium is hydrolyzed in saturated aqueous ammonium chloride solution and extracted with ethyl acetate. The organic phases are combined, washed with saturated sodium chloride solution and dried over magnesium sulfate. After filtration, the solvent is evaporated off and the brown oil obtained (1.2 g) is purified by chromatography on a column of silica eluted with a 70/30 heptane/ethyl acetate mixture. 489 mg (76%) of ethyl 2-[1-[2-butoxy-3'-(1-methyl-3-pentylureido)biphenyl-4-yl]meth-(E)-ylidene]butyrate are obtained.

b-2-[1-[2-butoxy-3'-(1-methyl-3-pentylureido)biphenyl-4-yl]meth-(E)-ylidene]butyric acid 40 mg (1 mmol) of sodium hydroxide are added to a solution of 483 mg (1 mmol) of ethyl 2-[1-[2-butoxy-3'-(1-methyl-3-pentylureido)biphenyl-4-yl]meth-(E)-ylidene]butyrate in 1 mL of ethanol and 10 mL of tetrahydrofuran. The reaction mixture is heated at 50° C. for 48 hours. The reaction medium is evaporated to dryness, taken up in water and acidified with aqueous 2 N hydrochloric acid solution and extracted with ethyl acetate. The organic phases are combined, washed with water and dried over magnesium sulfate. After filtration, the solvent is evaporated off and the oil obtained is purified by chromatography on a column of silica eluted with a 60/40 heptane/ethyl acetate mixture and then precipitated from heptane. 310 mg (83%) of 2-[1-[2-butoxy-3'-(1-methyl-3-pentylureido)biphenyl-4-yl]meth-(E)-ylidene]butyric acid are obtained in the form of a white powder with a melting point of 98-100° C.

$^1$H NMR (CDCl$_3$, 400 MHz): 0.84 (t, J=7-Hz, 3H); 0.93 (t, 3H); 1.19-1.25 (m, 4H); 1.29 (t, 3H); 1.38-1.46 (m, 4H); 1.74 (m, 2H); 2.64 (q, J=7-Hz, 2H); 3.17 (m, 2H); 3.31 (s, 3H); 4.01 (t, J=7.5-Hz, 2H); 4.42 (m, 1H); 7.03 (s, 1H); 7.13 (d, 1H); 7.21 (d, 1H); 7.37 (d, 1H); 7.44-7.51 (m, 3H); 7.80 (s, 1H).

EXAMPLE 37

Synthesis of 2-[1-[2-butoxy-3'-(3-heptyl-1-methylureido)biphenyl-4-yl]meth-(E)-ylidene]butyric acid

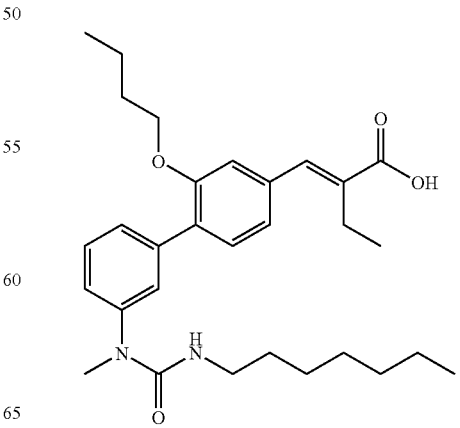

a-Ethyl 2-[1-[2-butoxy-3'-(3-heptyl-1-methylureido)biphenyl-4-yl]meth-(E)-ylidene]butyrate 3 mg (0.013 mmol) of palladium acetate and then 9 mg (0.026 mmol) of 2-(dicyclohexylphosphino)biphenyl are added to a mixture of 523 mg (1.3 mmol) of ethyl 2-[1-(3-butoxy-4-iodophenyl)meth-(E)-ylidene]butyrate (prepared as described in Example 22a), 494 mg (1.7 mmol) of 3-heptyl-1-methyl-1-[3-(4,4,5,5-tetramethyl[1.3.2]dioxaborolan-2-yl)phenyl]urea (prepared according to Example 35b) and 1.3 mL of aqueous 2M potassium phosphate solution in 6.5 mL of dimethylformamide. The reaction mixture is heated at 90-95° C. for 2 hours. The reaction medium is hydrolyzed with saturated ammonium chloride solution and extracted with ethyl acetate. The organic phases are combined, washed with saturated sodium chloride solution and dried over magnesium sulfate. After filtration, the solvent is evaporated off and the brown oil obtained (1.3 g) is purified by chromatography on a column of silica eluted with a 70/30 heptane/ethyl acetate mixture. 537 mg (79%) of ethyl 2-[1-[2-butoxy-3'-(3-heptyl-1-methylureido)biphenyl-4-yl]meth-(E)-ylidene]butyrate are obtained.

b-2-[1-[2-butoxy-3'-(3-heptyl-1-methylureido)biphenyl-4-yl]meth-(E)-ylidene]butyric acid 40 mg (1 mmol) of sodium hydroxide are added to a solution of 531 mg (1 mmol) of ethyl 2-[1-[2-butoxy-3'-(3-heptyl-1-methylureido)biphenyl-4-yl]meth-(E)-ylidene]butyrate in 1 mL of ethanol and 10 mL of tetrahydrofuran. The reaction mixture is heated at 50° C. for 48 hours. The reaction medium is evaporated to dryness, taken up in water, acidified with aqueous 2 N hydrochloric acid solution and extracted with ethyl acetate. The organic phases are combined, washed with water and dried over magnesium sulfate. After filtration, the solvent is evaporated off and the oil obtained is purified by chromatography on a column of silica eluted with a 60/40 heptane/ethyl acetate mixture and then precipitated from heptane. 317 mg (76%) of 2-[1-[2-butoxy-3'-(3-heptyl-1-methylureido)biphenyl-4-yl]meth-(E)-ylidene]butyric acid are obtained in the form of a white powder with a melting point of 62-64° C.
$^1$H NMR (CDCl$_3$, 400 MHz): 0.84 (t, 3H); 0.93 (t, 3H); 1.22 (m, 8H); 1.27 (t, 3H); 1.39-1.46 (m, 4H); 1.72-1.76 (m, 2H); 2.62-2.67 (q, 2H); 3.17 (q, 2H); 3.31 (s, 3H); 4.01 (t, 2H); 4.42 (t, 1H); 7.03 (s, 1H); 7.13 (d, 1H); 7.21 (d, 1H); 7.37 (d, 1H); 7.44-7.51 (m, 3H); 7.80 (s, 1H).

EXAMPLE 38

Synthesis of (Z)-2-ethoxy-3-[2-(2-ethoxyethoxy)-3'-(1-methyl-3-pentylureido)biphenyl-4-yl]acrylic acid

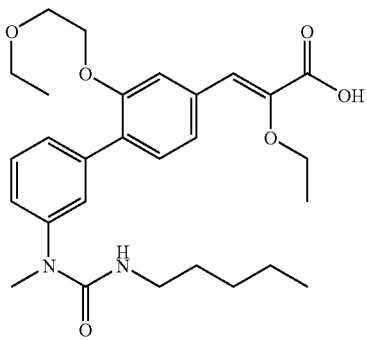 [SMILES: CCCCCNC(=O)N(C)c1cccc(-c2ccc(/C=C(\OCC)C(=O)O)cc2OCCOCC)c1]

a-Methyl 3-(2-ethoxyethoxy)-4-iodobenzoate 3.15 g (20 mmol) of 2-bromoethyl ethyl ether and 3.4 g (24.6 mmol) of potassium carbonate are added to a solution of 5.7 g (20 mmol) of methyl 3-hydroxy-4-iodobenzoate (prepared according to Example 19d) in 50 mL of methyl ethyl ketone. The reaction mixture is heated at 80° C. for 12 hours. The reaction is stopped by addition of 50 mL of water and extraction with ethyl acetate. The organic phases are combined and dried over sodium sulfate. The solvents are evaporated off and the residue is then purified by chromatography on a column of silica eluted with an 80/20 heptane/ethyl acetate mixture. 5.93 g (83%) of methyl 3-(2-ethoxyethoxy)-4-iodobenzoate are obtained in the form of a colorless oil.

b-[3-(2-ethoxyethoxy)-4-iodophenyl]methanol 1.2 g (55 mmol) of lithium borohydride are added to a solution of 5.93 g (18 mmol) of methyl 3-(2-ethoxyethoxy)-4-iodobenzoate in 30 mL of tetrahydrofuran. The reaction mixture is heated at 60° C. overnight and then hydrolyzed in ice-cold saturated ammonium chloride solution. The reaction medium is neutralized with concentrated hydrochloric acid and then extracted with ethyl acetate. The organic phases are washed with water and dried over sodium sulfate. The solvent is evaporated off and 5.43 g (99%) of [3-(2-ethoxyethoxy)-4-iodophenyl]methanol are obtained in the form of a colorless oil.

c-3-(2-ethoxyethoxy)-4-iodobenzaldehyde 14.5 g (218 mmol) of manganese oxide are added to a solution of 5.4 g (21.8 mmol) of 3-[(2-ethoxyethoxy)-4-iodophenyl]methanol in 110 mL of dichloromethane. The reaction mixture is stirred for 16 hours at room temperature, filtered through Celite and rinsed with dichloromethane and ethyl acetate. The solvents are evaporated off and the residue is then purified by chromatography on a column of silica eluted with a 90/10 heptane/ethyl acetate mixture. 4.7 g (88%) of 3-(2-ethoxyethoxy)-4-iodobenzaldehyde are obtained in the form of a yellow oil.

d-Ethyl (Z)-3-[3-(2-ethoxyethoxy)-4-iodophenyl]-2-ethoxyacrylate 0.26 g (6.87 mmol) of sodium hydride is added portionwise to a solution at 0° C. of 1.75 g (6.87 mmol) of ethyl (diethoxyphosphoryl)ethoxyacetate (prepared according to Example 1b) in 20 mL of tetrahydrofuran. The reaction mixture is stirred for 45 minutes at room temperature and 2 g (6.25 mmol) of 3-(2-ethoxyethoxy)-4-iodobenzaldehyde in 10 mL of tetrahydrofuran are then added dropwise. The reaction is slightly exothermic, and the reaction mixture is maintained at a temperature of 25-30° C. with an ice-water bath. When the temperature has stabilized, the reaction mixture is stirred for 24 hours at room temperature. After addition of 50 mL of water, the reaction medium is extracted with ethyl acetate. The organic phases are combined, washed with saturated sodium chloride solution and then dried over sodium sulfate. After evaporating under vacuum, the crude product obtained is purified by chromatography on a column of silica eluted with a 90/10 heptane/ethyl acetate mixture to give 61.2 mg of the (E) isomer of ethyl 3-[3-(2-ethoxyethoxy)-4-iodophenyl]-2-ethoxyacrylate, 1.56 g of a mixture of (Z) and (E) isomers and 270.3 mg of the isomer ethyl (Z)-3-[3-(2-ethoxyethoxy)-4-iodophenyl]-2-ethoxyacrylate in the form of yellow oils.

e-Ethyl (Z)-2-ethoxy-3-[2-(2-ethoxyethoxy)-3'-(1-methyl-3-pentylureido)biphenyl-4-yl]acrylate 29 mg (0.08 mmol) of 2-(dicyclohexylphosphino)biphenyl and 9.3 mg (0.04 mmol) of palladium acetate and then 1.35 mL (2.7 mmol) of aqueous 2 M potassium phosphate solution are added to a solution of 0.9 g (2.07 mmol) of ethyl (Z)-3-[3-(2-ethoxyethoxy)-4-iodophenyl]-2-ethoxyacrylate and 0.58 g (2.5 mmol) of 3-(1-methyl-3-pentylureido)phenylboronic acid (prepared according to Example 24h) in 10 mL of dimethylformamide. The reaction medium is heated at 90° C. for 3 hours. After addition of 20 mL of water and extraction with ethyl acetate, the organic phases are combined, washed with saturated sodium chloride solution and dried over sodium sulfate. After evaporating under vacuum, the residue obtained is purified by chromatography on a column of silica eluted with an 80/20 heptane/ethyl acetate mixture. 100 mg (12%) of ethyl (Z)-2-ethoxy-3-[2-(2-ethoxyethoxy)-3'-(1-methyl-3-pentylureido)biphenyl-4-yl]acrylate are obtained.

f-(Z)-2-ethoxy-3-[2-(2-ethoxyethoxy)-3'-(1-ethyl-3-pentylureido)biphenyl-4-yl]acrylic acid 18 mg (4.5 mmol) of sodium hydroxide are added to a solution of 237 mg (0.45 mmol) of ethyl (Z)-2-ethoxy-3-[2-(2-ethoxyethoxy)-3'-(1-methyl-3-pentylureido)biphenyl-4-yl]acrylate in 5 mL of tetrahydrofuran and 0.5 mL of ethanol. The reaction mixture is stirred for 12 hours at room temperature. After addition of 10 mL of water and acidification to pH 3 with aqueous 1 N hydrochloric acid solution, the reaction medium is extracted with ethyl acetate. The organic phases are combined, dried over sodium sulfate and evaporated. After triturating the residue in heptane, 100 mg (46%) of (Z)-3-[3'-(3-heptyl-1-methylureido)biphenyl-4-yl]acrylic acid are obtained in the form of pale yellow crystals (m.p.=102.4° C.).
$^1$H NMR (CDCl$_3$, 400 MHz): 0.86 (t, J=7.2-Hz, 3H); 1.20 (t, J=7.01-Hz, 3H); 1.28 (m, 4H); 1.46 (t, J=7.04-Hz, 3H); 1.47 (m, 2H); 3.2 (m, 2H); 3.34 (s, 3H); 3.51 (m, 2H); 3.76 (m, 2H); 4.13 (q, J=7.1-Hz, 2H); 4.22 (m, 2H); 4.52 (s, 1H); 7.15 (s, 1H); 7.21 (m, 1H); 7.37-7.47 (m, 3H); 7.59-7.63 (m, 3H).

EXAMPLE 39

Synthesis of (Z)-3-[2-(2-ethoxyethoxy)-3'-(1-methyl-3-pentylureido)biphenyl-4-yl]-2-methoxyacrylic acid

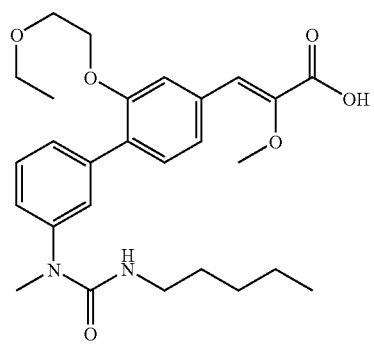 [SMILES: CCCCCNC(=O)N(C)c1cccc(-c2ccc(/C=C(\OC)C(=O)O)cc2OCCOCC)c1]

a-Methyl (Z)-3-[3-(2-ethoxyethoxy)-4-iodophenyl]-2-methoxyacrylate 0.30 g (7.5 mmol) of sodium hydride is added portionwise to a solution at 0° C. of 1.80 g (7.5 mmol) of methyl (di-ethoxyphosphanyloxy)methoxyacetate (prepared according to Example 24b) in 20 mL of tetrahydrofuran. The reaction mixture is stirred for 45 minutes at room temperature and then 2 g (6.25 mmol) of 3-(2-ethoxyethoxy)-4-iodobenzaldehyde (prepared according to Example 38c) in 10 mL of tetrahydrofuran. The reaction is slightly exothermic, and the reaction mixture is maintained at a temperature of 25-30° C. with an ice-water bath. When the temperature has stabilized, the reaction mixture is stirred for 24 hours at room temperature. After addition of 50 mL of water and extraction with ethyl acetate, the organic phases are combined, washed with saturated sodium chloride solution, dried over sodium sulfate and evaporated. The crude product obtained is purified by chromatography on a column of silica eluted with a 95/5 heptane/ethyl acetate mixture to give 411 mg of methyl (Z)-3-[3-(2-ethoxyethoxy)-4-iodophenyl]-2-methoxyacrylate and 526 mg of methyl (E)-3-[3-(2-ethoxyethoxy)-4-iodophenyl]-2-methoxyacrylate in the form of colorless oils.

b-Methyl (Z)-3-[2-(2-ethoxyethoxy)-3'-(1-methyl-3-pentylureido)biphenyl-4-yl]-2-methoxyacrylate 6.9 mg (0.02 mmol) of 2-(dicyclohexylphosphino)biphenyl and 2.2 mg (0.01 mmol) of palladium acetate and then 0.32 mL (0.64 mmol) of aqueous 2 M potassium phosphate solution are added to a solution of 200 mg (0.49 mmol) of methyl (Z)-3-[3-(2-ethoxyethoxy)-4-iodophenyl]-2-methoxyacrylate and 0.65 g (2.5 mmol) of 3-(1-methyl-3-pentylureido)phenylboronic acid (prepared according to Example 24h) in 10 mL of dimethylformamide. The reaction mixture is heated at 90° C. for 3 hours. After addition of 20 mL of water and extraction with ethyl acetate, the organic phases are combined, washed with saturated sodium chloride solution and dried over sodium sulfate. The solvents are evaporated off and the residue is then purified by chromatography on a column of silica eluted with a 70/30 heptane/ethyl acetate mixture. 217.8 mg (89%) of methyl (Z)-2-Ethoxy-3-[2-(2-ethoxyethoxy)-3'-(1-methyl-3-pentylureido)biphenyl-4-yl]acrylate are obtained in the form of an orange oil.

c-(Z)-3-[2-(2-ethoxyethoxy)-3'-(1-methyl-3-pentylureido)biphenyl-4-yl]-2-methoxyacrylic acid 17 mg (4.2 mmol) of sodium hydroxide are added to a solution of 211 mg (0.42 mmol) of methyl (Z)-3-[2-(2-ethoxyethoxy)-3'-(1-methyl-3-pentylureido)biphenyl-4-yl]-2-methoxyacrylate in 5 mL of tetrahydrofuran and 0.5 mL of methanol. The reaction mixture is stirred overnight at room temperature. After addition of 10 mL of water and acidification to pH 3 with 1 N hydrochloric acid, the reaction medium is extracted with ethyl acetate. The organic phases are combined, dried over sodium sulfate and evaporated, and the residue obtained is then purified by chromatography on a column of silica eluted with a 98/2 dichloromethane/methanol mixture. 160 mg (74%) of (Z)-3-[2-(2-ethoxyethoxy)-3'-(1-methyl-3-pentylureido)biphenyl-4-yl]-2-methoxyacrylic acid are obtained in the form of white crystals. (m.p.=78.2° C.).
$^1$H NMR (CDCl$_3$, 400 MHz): 0.87 (t, J=61.20 (t, J=6.8-Hz, 3H); 1.23-1.31 (m, 4H); 1.46 (m, 2H); 3.23 (m, 3H); 3.36 (m, 3H); 3.53 (td, J=6.7-Hz, J=5.1-Hz, 2H); 3.77 (m, 2H); 3.88 (s, 3H); 4.21 (m, 2H); 4.5 (m, 1H); 7.16 (s, 1H); 7.24 (m, 1H); 7.28-7.48 (m, 3H); 7.56 (s, H); 7.58 (d, J=6.8-Hz, 2H).

EXAMPLE 40

Synthesis of (E)-3-[2-butoxy-3'-(3-heptyl-1-methylureido)biphenyl-4-yl]-2-methoxyacrylic acid

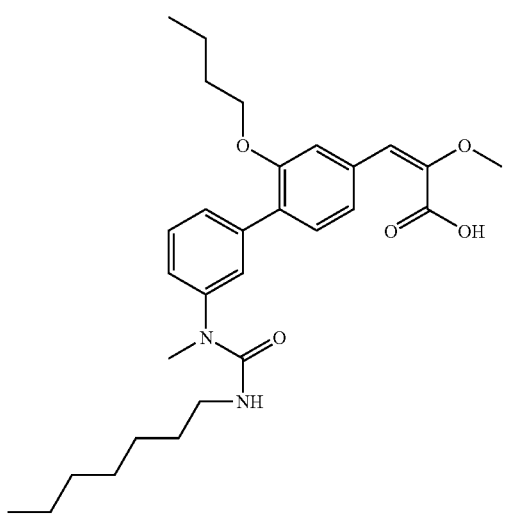 [SMILES: CCCCCCCNC(=O)N(C)c1cccc(-c2ccc(/C=C(/OC)C(=O)O)cc2OCCCC)c1]

a-Methyl (E)-3-[2-butoxy-3'-(3-heptyl-1-methylureido)biphenyl-4-yl]-2-methoxyacrylate 0.4 g (1 mmol) of methyl (E)-3-(3-butoxy-4-iodophenyl)-2-methoxyacrylate prepared as described in Example 24c, 0.5 g (1.33 mmol) of 3-heptyl-1-methyl-1-[3-(4,4,5,5-tetramethyl[1.3.2]dioxaborolan-2-yl)phenyl]urea prepared according to Example 35b and 1 mL (2 mmol) of aqueous 2 M potassium phosphate solution are dissolved in 15 mL of dimethylformamide. After bubbling nitrogen through the reaction mixture for 10 minutes, 2 mg (0.01 mmol) of palladium (II) acetate and 7 mg (0.02 mmol) of 2-(dicyclohexylphosphine)biphenyl are added. The reaction mixture is heated at 90° C. for 3 hours with vigorous stirring. After cooling, the reaction is worked up by addition of water and extraction with ethyl acetate. The organic phases are combined, washed with water and with saturated sodium chloride solution and then dried over magnesium sulfate. The solvents are evaporated off. The crude product obtained is purified by chromatography on a column of silica eluted with a 70/30 heptane/ethyl acetate mixture to give 0.33 g (64%) of methyl (E)-3-[2-butoxy-3'-(1-methyl-3-heptylureido)biphenyl-4-yl]-2-methoxyacrylate in the form of a colorless oil.

b-(E)-3-[2-butoxy-3'-(3-heptyl-1-methylureido)biphenyl-4-yl]-2-methoxyacrylic acid 1.3 mL (1.3 mmol) of aqueous 1 M sodium hydroxide solution are added to a solution of 0.33 g (0.65 mmol) of methyl (E)-3-[2-butoxy-3'-(1-methyl-3-pentylureido)biphenyl-4-yl]-2-methoxyacrylate in 8 mL of tetrahydrofuran. The reaction mixture is stirred at 68° C. for 6 hours. After cooling, the reaction is worked up by addition of 2 mL (2 mmol) of aqueous 1 M hydrochloric acid solution and 10 mL of water and extraction with ethyl acetate. The organic phases are combined, washed with saturated sodium chloride solution and then dried over magnesium sulfate. The solvents are evaporated off. The residue obtained is purified by chromatography on a column of silica eluted with a 70/30 and then 50/50 heptane/ethyl acetate mixture. The product obtained is then recrystallized from isopropyl ether to give 0.25 g (90%) of (E)-3-[2-butoxy-3'-(1-methyl-3-heptylureido)biphenyl-4-yl]-2-methoxyacrylic acid in the form of a white solid with a melting point of 89° C.

$^1$H NMR (CDCl$_3$, 400 MHz): 0.86 (t, J=7.1-Hz, 3H); 0.91 (t, J=7.3-Hz, 3H); 1.22-1.28 (m, 8H); 1.37 (m, 2H); 1.40 (m, 2H); 1.70 (m, 2H); 3.16 (td, J=7.1-Hz, J=5.6-Hz, 2H); 3.28 (s, 3H); 3.82 (s, 3H); 3.98 (t, J=6.6-Hz, 2H); 4.45 (t, J=5.6-Hz, 1H); 6.18 (s, 1H); 6.99 (d, 1H); 7.05 (s, 1H); 7.17 (d, 1H); 7.24 (d, J=7.7-Hz, 1H); 7.43 (m, 1H); 7.49-7.50 (m, 2H).

EXAMPLE 41

Synthesis of L-Arginine salt of (Z)-2-ethoxy-3-[3'-(3-heptyl-1-methylureido)biphenyl-4-yl]acrylic acid

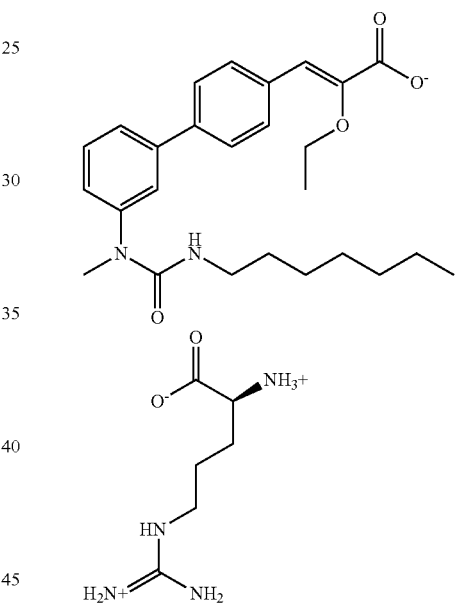

a-Ethyl (Z)-2-ethoxy-3-[4-(4,4,5,5-tetramethyl[11.3]dioxaborolan-2-yl)phenyl]acrylate 4.0 g (40.1 mmol) of potassium acetate and 5.1 g (20.1 mmol) of bis-pinacoldiborane are added to a solution of 4 g (13.4 mmol) of ethyl (Z)-3-(4-bromophenyl)-2-ethoxyacrylate (prepared according to Example 1c) in 150 mL of dimethylformamide. After bubbling nitrogen through the reaction mixture for 20 minutes, 0.44 g (0.54 mmol) of dichloro [1,1'-bis(diphenylphosphino)ferrocene]palladium is added. The reaction mixture is heated at 80° C. for 18 hours with vigorous stirring.

After cooling, the reaction mixture is worked up by addition of 100 mL of water and extraction with ethyl acetate. The organic phases are combined, washed with saturated sodium chloride solution and then dried over magnesium sulfate. The solvents are evaporated off. The crude product obtained is purified by chromatography on a column of silica eluted with an 80/20 heptane/ethyl acetate mixture to give 2.8 g (61%) of ethyl (Z)-2-ethoxy-3-[4-(4,4,5,5-tetramethyl[1.3]dioxaborolan-2-yl)phenyl]acrylate.

b-Ethyl (Z)-2-ethoxy-3-(3'-methylaminobiphenyl-4-yl)acrylate 1.0 g (2.9 mmol) of ethyl (Z)-2-ethoxy-3-[4-(4,4,5,5-tetramethyl[1.3]dioxaborolan-2-yl)phenyl]acrylate, 0.45 g (2.4 mmol) of (3-bromophenyl)methylamine (prepared according to Example 24f) and 1.1 g (7.2 mmol) of caesium fluoride are dissolved in 60 mL of diethylene glycol dimethyl ether. After bubbling nitrogen through the reaction mixture for 20 minutes, 0.12 g (0.15 mmol) of dichloro[1,1'-bis(diphenylphosphino)ferrocene]palladium is added. The reaction mixture is heated at 80° C. for 18 hours with vigorous stirring. After cooling, the reaction is worked up by addition of 60 mL of water and extraction with ethyl acetate. The organic phases are combined, washed with saturated aqueous sodium chloride solution and then dried over magnesium sulfate. After filtration, the solvents are evaporated off. The crude product obtained is purified by chromatography on a column of silica eluted with a 90/10 heptane/ethyl acetate mixture to give 0.68 g (87%) of ethyl (Z)-2-ethoxy-3-(3'-methylaminobiphenyl-4-yl)acrylate.

c-Ethyl (Z)-2-ethoxy-3-{3'-[methyl-(4-nitrophenoxycarbonyl)amino]biphenyl-4-yl}acrylate 0.63 g (3.1 mmol) of 4-nitrophenyl chloroformate and then 0.54 mL (3.1 mmol) of diethylamine are added to a solution of 0.68 g (2.1 mmol) of ethyl (Z)-2-ethoxy-3-(3'-methylaminobiphenyl-4-yl)acrylate in 15 mL of dichloromethane. The reaction mixture is stirred for 1 hour 30 minutes at room temperature. The reaction is worked up by addition of 10 mL of water and then extracted with dichloromethane. The organic phases are combined and then dried over magnesium sulfate. The solvents are evaporated off. 1.3 g (100%) of ethyl (Z)-2-ethoxy-3-{3'-[methyl-(4-nitrophenoxycarbonyl)amino]biphenyl-4-yl}acrylate are obtained in the form of a yellow oil.

d-Ethyl (Z)-2-ethoxy-3-[3'-(3-heptyl-1-methylureido)biphenyl-4-yl]acrylate 0.31 mL (2.10 mmol) of heptylamine is added to a solution of 0.51 g (1.05 mmol) of ethyl (Z)-2-ethoxy-3-{3'-[methyl-(4-nitrophenoxycarbonyl)amino]biphenyl-4-yl}acrylate in 15 mL of dimethylformamide. The tube is sealed and rapidly placed in an oil bath preheated to 80° C. The reaction mixture is stirred at 80° C. for 1 hour 30 minutes. After cooling, the reaction is worked up by addition of 10 mL of water and extraction with ethyl acetate. The organic phases are combined, washed with saturated sodium chloride solution and then dried over magnesium sulfate. The solvents are evaporated off. The crude product obtained is purified by chromatography on a column of silica eluted with a 75/25 heptane/ethyl acetate mixture to give 0.38 g (77%) of ethyl (Z)-2-ethoxy-3-[3'-(3-heptyl-1-methylureido)biphenyl-4-yl]acrylate in the form of a colorless oil.

e-(Z)-2-ethoxy-3-[3'-(3-heptyl-1-methylureido)biphenyl-4-yl]acrylic acid 1.2 mL (1.2 mmol) of aqueous 1 M lithium hydroxide solution are added to a solution of 0.4 g (0.8 mmol) of ethyl (Z)-2-ethoxy-3-[3'-(3-heptyl-1-methylureido)biphenyl-4-yl] acrylate in 8 mL of tetrahydrofuran. The reaction mixture is stirred at 68° C. for 18 hours. After cooling, the reaction is worked up by addition of 1.2 mL (1.2 mmol) of aqueous 1 M acetic acid solution and 10 mL of water and extraction with ethyl acetate. The organic phases are combined, washed with saturated sodium chloride solution and then dried over magnesium sulfate. The solvents are evaporated off. The crude product obtained is purified by chromatography on a column of silica eluted with a 98/2 dichloromethane/methanol mixture to give 240 mg (68%) of (Z)-2-ethoxy-3-[3'-(3-heptyl-1-methylureido)biphenyl-4-yl]acrylic acid in the form of a colorless oil.

f-L-Arginine salt of (Z)-2-ethoxy-3-[3'-(3-heptyl-1-methylureido)biphenyl-4-yl]acrylic acid 80 mg (0.46 mmol) of L-arginine are dissolved in 0.5 mL of water and then added dropwise to a solution of 200 mg (0.46 mmol) of (Z)-2-ethoxy-3-[3'-(3-heptyl-1-methylureido)biphenyl-4-yl]acrylic acid in 3 mL of ethanol preheated to 80° C. The reaction mixture is stirred for 5 minutes at 80° C. and then cooled slowly to room temperature. 3 mL of diethyl ether are added and the reaction mixture is stirred at room temperature for 15 hours. A white precipitate forms. After filtration, the solid obtained is rinsed with diethyl ether and then dried in an oven under vacuum to give 0.28 g (71%) of the L-arginine salt of (Z)-2-ethoxy-3-[3'-(3-heptyl-1-methylureido)biphenyl-4-yl]acrylic acid in the form of a white solid with a melting point of 185° C.

$^1$H NMR (CDCl$_3$, 400 MHz): 0.84 (t, J=6.5-Hz, 3H); 1.23-1.34 (m, 8H); 1.27 (t, J=7.0-Hz, 3H); 1.38-1.40 (m, 2H); 1.65 (m, 2H); 1.71-7.82 (m, 2H); 3.00-3.16 (m, 4H); 3.20 (s, 3H); 3.32-3.34 (m, 1H); 4.01 (q, J=7.0-Hz, 2H); 5.75 (t, J=5.5-Hz, 1H); 6.50 (s, 1H); 7.17 (d, J=7.5-Hz, 1H); 7.40-7.48 (m, 3H); 7.55 (d, J=8.2-Hz, 2H); 7.75 (d, J=8.2-Hz, 2H).

EXAMPLE 42

Synthesis of L-Arginine salt of (Z)-2-ethoxy-3-[3'-(1-methyl-3-pentylureido)biphenyl-4-yl]acrylic acid

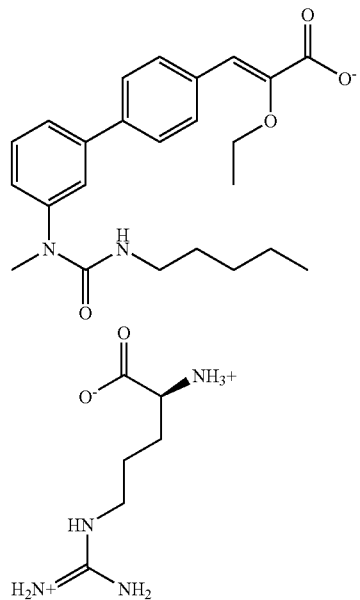

a-Ethyl (Z)-2-ethoxy-3-[3'-(1-methyl-3-pentylure-ido)biphenyl-4-yl]acrylate 0.24 mL (2.1 mmol) of n-pentylamine is added to a solution of 0.51 g (1.05 mmol) of ethyl (Z)-2-ethoxy-3-{3'-[methyl-(4-nitrophenoxycarbonyl)amino]biphenyl-4-yl}acrylate (prepared as in Example 40c) in 15 mL of dimethylformamide. The tube is sealed and rapidly placed in an oil bath preheated to 80° C. The reaction mixture is stirred at 80° C. for 1 hour 30 minutes. After cooling, the reaction is worked up by addition of 10 mL of water and extraction with ethyl acetate. The organic phases are combined, washed with saturated sodium chloride solution and then dried over magnesium sulfate. The solvents are evaporated off.

The crude product obtained is purified by chromatography on a column of silica eluted with a 75/25 heptane/ethyl acetate mixture to give 0.31 g (67%) of ethyl (Z)-2-ethoxy-3-[3'-(1-methyl-3-pentylureido)biphenyl-4-yl]acrylate in the form of a colorless oil.

b-(Z)-2-ethoxy-3-[3'-(1-methyl-3-pentylureido)biphenyl-4-yl]acrylic acid 1.1 mL (1.1 mmol) of aqueous 1 M lithium hydroxide solution are added to a solution of 0.3 g (0.7 mmol) of ethyl (Z)-2-ethoxy-3-[3'-(1-methyl-3-pentylureido)biphenyl-4-yl]acrylate in 8 mL of tetrahydrofuran. The reaction mixture is stirred at 68° C. for 18 hours. After cooling, the reaction is worked up by addition of 1.1 mL (1.1 mmol) of aqueous 1 M acetic acid solution and 10 mL of water and extraction with ethyl acetate. The organic phases are combined, washed with saturated sodium chloride solution and then dried over magnesium sulfate. The solvents are evaporated off. The crude product obtained is purified by chromatography on a column of silica eluted with a 98/2 dichloromethane/methanol mixture to give 0.19 g (65%) of (Z)-2-ethoxy-3-[3'-(1-methyl-3-pentylureido)biphenyl-4-yl]acrylic acid in the form of a colorless oil.

c-L-Arginine salt of (Z)-2-ethoxy-3-[3'-(1-methyl-3-pentylureido)biphenyl-4-yl]acrylic acid 73 mg (0.4 mmol) of L-arginine are dissolved in 0.5 mL of water and then added dropwise to a solution of 200 mg (0.4 mmol) of ethyl (Z)-2-ethoxy-3-[3'-(1-methyl-3-pentylureido)biphenyl-4-yl]acrylate in 3 mL of ethanol preheated to 80° C. The reaction mixture is stirred for 5 minutes at 80° C. and then cooled slowly to room temperature. 3 mL of ethyl ether are added and the reaction mixture is stirred at room temperature for 15 hours. A white precipitate forms. After filtration, the solid obtained is rinsed with ethyl ether and then dried in an oven under vacuum to give 190 mg (81%) of the L-arginine salt of (Z)-2-ethoxy-3-[3'-(1-methyl-3-pentylureido)biphenyl-4-yl]acrylic acid in the form of a white solid with a melting point of 191° C.

$^1$H NMR (CDCl$_3$, 400 MHz): 0.85 (t, J=6.8-Hz, 3H); 1.21-1.30 (m, 7H); 1.37-1.42 (m, 2H); 1.63 (m, 2H); 1.71-1.79 (m, 2H); 3.00-3.05 (m, 2H); 3.09-3.15 (m, 2H); 3.20 (s, 3H); 3.31 (m, 1H); 4.10 (q, J=7.0-Hz, 2H); 5.89 (t, J=5.5-Hz, 1H); 6.49 (s, 1H); 7.19 (d, J=7.6-Hz, 1H); 7.41-7.50 (m, 3H); 7.58 (d, J=8.3-Hz, 2H); 7.76 (d, J=8.3-Hz, 2H).

EXAMPLE 43

Synthesis of (Z)-3-[3'-(3-butyl-1-methylureido)biphenyl-4-yl]-2-ethoxyacrylic acid

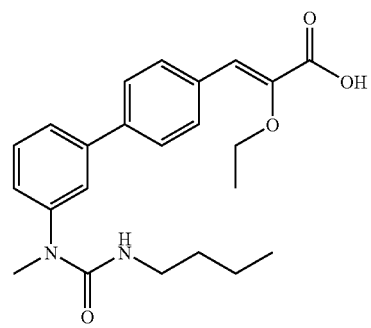 [SMILES: CCCCNC(=O)N(C)c1cccc(-c2ccc(/C=C(\OCC)C(=O)O)cc2)c1]

a-Methyl [3-(4,4,5,5-tetramethyl[1.3.2]dioxaborolan-2-yl)phenyl]amine

To a solution of 10.9 g (59 mmol) of (3-bromophenyl)methylamine (prepared according to Example 24f) and 15 g (59 mmol) of bis-pinacoldiborane in 110 mL of dimethylformamide, 17.4 g (177 mmol) of potassium acetate and 2.4 g (3 mmol) of dichloro[1,1'-bis(diphenylphosphino)ferrocene]palladium are added. The reaction medium is heated at 85° C. for 3 hours, cooled and extracted with dichloromethane. The organic phase is washed thoroughly with water, dried over magnesium sulfate, filtered and evaporated. The residue obtained is purified by chromatography on a column of silica eluted with an 80/20 heptane/ethyl acetate mixture. 12.7 g (92%) of methyl[3-(4,4,5,5-tetramethyl[1.3.2]dioxaborolan-2-yl)phenyl]amine are obtained.

b-Ethyl (Z)-2-ethoxy-3-(3'-methylaminobiphenyl-4-yl)acrylate

To a solution of 10.8 g (36.1 mmol) of ethyl (Z)-3-(4-bromophenyl)-2-ethoxyacrylate prepared beforehand as described in Example 1c and 108 mL (217 mmol) of aqueous 2 M sodium carbonate solution in 120 mL of toluene, 1.5 g (1.8 mmol) of dichloro[1,1'-bis(diphenylphosphino)ferrocene]palladium are added. The reaction medium is stirred and a solution of 9.25 g (39.7 mmol) of methyl[3-(4,4,5,5-tetramethyl[1.3.2]dioxaborolan-2-yl)phenyl]amine in 90 mL of ethanol is then added dropwise. After stirring at 80° C. for 2 hours, the reaction medium is hydrolyzed and diluted with ethyl acetate. After separation of the phases by settling, the ethyl acetate phase is washed with saturated sodium chloride solution, dried over magnesium sulfate, filtered and evaporated. The residue obtained is purified by chromatography on a column of silica eluted with a 90/10 and then 80/20 heptane/ethyl acetate mixture. 10.5 g (94%) of ethyl (Z)-2-ethoxy-3-(3'-methylaminobiphenyl-4-yl)acrylate are obtained in the form of a yellow oil. After taking up the product in pentane, 9.5 g (85%) of ethyl (Z)-2-ethoxy-3-(3'-methylaminobiphenyl-4-yl)acrylate are obtained in the form of a pale yellow solid with a melting point of 52° C.

c-Ethyl (Z)-2-ethoxy-3-{3'-[methyl-(4-nitrophenoxy-carbonyl)amino]biphenyl-4-yl}acrylate To a solution of 4 g (12.3 mmol) of ethyl (Z)-2-ethoxy-3-(3'-methylaminobiphenyl-4-yl)acrylate in 80 mL of dichloromethane, cooled to 0° C., 3 g (14.7 mmol) of 4-nitrophenyl chloroformate and then 2.6 mL (14.7 mmol) of diisopropylethylamine are successively added dropwise. The reaction medium is then stirred at room temperature for 2 hours. After addition of water, the medium is extracted with dichloromethane. The organic phase is washed with water, dried over magnesium sulfate, filtered and evaporated. 7 g (100%) of crude residue are obtained and used without further purification in the following step.

d-Ethyl (Z)-3-[3'-(3-butyl-1-methylureido)biphenyl-4-yl]-2-ethoxyacrylate

A solution of 1.75 g (3 mmol) of ethyl (Z)-2-ethoxy-3-{3'-[methyl-(4-nitrophenoxycarbonyl)amino]biphenyl-4-yl}acrylate and 0.4 mL (3.7 mmol) of n-butylamine in 20 mL of dimethylformamide is heated at 80° C. for 2 hours. After addition of water, the reaction medium is extracted with ethyl acetate, washed with water, dried over magnesium sulfate, filtered and evaporated. The residue obtained is purified by chromatography on a column of silica eluted with a 70/30 heptane/ethyl acetate mixture. 0.8 g (63%) of ethyl (Z)-3-[3'-(3-butyl-1-methylureido)biphenyl-4-yl]-2-ethoxyacrylate is obtained in the form of a white solid after trituration from pentane.

e-(Z)-3-[3'-(3-butyl-1-methylureido)biphenyl-4-yl]-2-ethoxyacrylic acid 2.9 mL (2.9 mmol) of aqueous 1 M lithium hydroxide solution are added to a solution of 0.8 g (1.9 mmol) of ethyl (Z)-3-[3'-(3-butyl-1-methylureido)biphenyl-4-yl]-2-ethoxyacrylate in 10 mL of tetrahydrofuran. The reaction medium is heated at reflux for 20 hours. After cooling, 3 mL (2.9 mmol) of 1 N acetic acid are added and the reaction medium is extracted with ethyl acetate. The organic phase is washed with saturated sodium chloride solution, filtered and evaporated. 760 mg (100%) of (Z)-3-[3'-(3-butyl-1-methylureido)biphenyl-4-yl]-2-ethoxyacrylic acid are obtained in the form of a white solid with a melting point of 126° C.

$^1$H NMR (CDCl$_3$, 400 MHz): 0.88 (t, J=7.3-Hz, 3H); 1.26 (m, 2H); 1.42 (m, 2H); 1.43 (t, J=7-Hz); 3.20 (m, 2H); 3.33 (s, 3H); 4.11 (q, J=7-Hz, 2H); 4.42 (t, J=5.5-Hz, 1H); 7.18 (s, 1H), 7.25 (m, 1H); 7.49-7.53 (m, 2H); 7.58 (m, 1H); 7.60 (m, J=8.4-Hz, 2H); 7.91 (d, J=8.4-Hz, 2H).

EXAMPLE 44

Synthesis of (Z)-3-[3'-(3-cyclohexyl-1-methylureido)biphenyl-4-yl]-2-ethoxyacrylic acid a-Ethyl (Z)-3-[3'-(3-cyclohexyl-1-methylureido)biphenyl-4-yl]-2-ethoxyacrylate In a manner similar to that of Example 43d, starting with 1.75 g (3 mmol) of ethyl (Z)-2-ethoxy-3-{3'-[methyl(4-nitrophenoxycarbonyl)amino]biphenyl-4-yl}acrylate (prepared according to Example 43c) and 0.42 mL (3.7 mmol) of cyclohexylamine, 0.7 g (50%) of ethyl (Z)-3-[3'-(3-cyclohexyl-1-methylureido)biphenyl-4-yl]-2-ethoxyacrylate is obtained.

b-(Z)-3-[3'-(3-cyclohexyl-1-methylureido)biphenyl-4-yl]-2-ethoxyacrylic acid

In a manner similar to that of Example 43e, starting with 0.7 g (1.5 mmol) of ethyl (Z)-3-[3'-(3-cyclohexyl-1-methylureido)biphenyl-4-yl]-2-ethoxyacrylate, 0.6 g (95%) of (Z)-3-[3'-(3-cyclohexyl-1-methylureido)biphenyl-4-yl]-2-ethoxyacrylic acid is obtained in the form of a white solid with a melting point of 85° C.

$^1$H NMR (CDCl$_3$, 400 MHz): 1.00-1.20 (m, 2H); 1.26-1.35 (m, 3H); 1.43 (t, J=7-Hz, 3H); 1.59-1.63 (m, 3H); 1.88 (m, 2H); 3.32 (s, 3H); 3.67 (m, 1H); 4.11 (q, J=7-Hz, 2H); 4.28 (d, J=8-Hz, 1H); 7.18 (s, 1H); 7.24 (m, 1H); 7.48-7.56 (m, 3H); 7.61 (d, J=8.4-Hz, 2H); 7.90 (d, J=8.4-Hz, 2H).

EXAMPLE 45

Synthesis of (Z)-2-ethoxy-3-(3'-{3-[2-(4-methoxyphenyl)ethyl]-1-methylureido}biphenyl-4-yl)acrylic acid

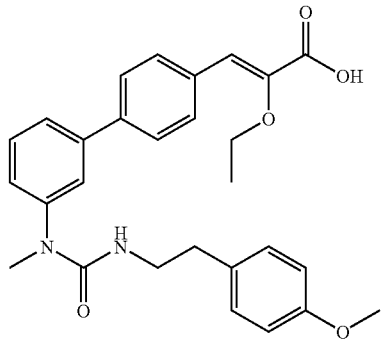 [SMILES: CCO/C(=C\c1ccc(-c2cccc(N(C)C(=O)NCCc3ccc(OC)cc3)c2)cc1)C(=O)O]

a-Ethyl (Z)-2-ethoxy-3-(3'-{3-[2-(4-methoxyphenyl)ethyl]-1-methylureido}biphenyl-4-yl)acrylate In a manner similar to that of Example 43d, starting with 1.75 g (3 mmol) of ethyl (Z)-2-ethoxy-3-{3'-[methyl-(4-nitrophenoxycarbonyl)amino]biphenyl-4-yl}acrylate and 0.54 mL (3.7 mmol) of 2-(4-methoxyphenyl)ethylamine, 1.1 g (69%) of ethyl (Z)-2-ethoxy-3-(3'-{3-[2-(4-methoxyphenyl)ethyl]-1-methylureido}biphenyl-4-yl)acrylate are obtained.

b-(Z)-2-ethoxy-3-(3'-{3-[2-(4-methoxyphenyl)ethyl]-1-methylureido}biphenyl-4-yl)acrylic acid In a manner similar to that of Example 43e, starting with 1.1 g (2.1 mmol) of ethyl (Z)-2-ethoxy-3-(3'-{3-[2-(4-methoxyphenyl)ethyl]-1-methylureido}biphenyl-4-yl)acrylate, 0.9 g (90%) of (Z)-2-ethoxy-3-(3'-{3-[2-(4-methoxyphenyl)ethyl]-1-methylureido}biphenyl-4-yl)acrylic acid is obtained in the form of a beige-colored foam.

$^1$H NMR (CDCl$_3$, 400 MHz): 1.44 (t, J=7-Hz, 3H); 2.69 (t, J=6.8-Hz, 2H); 3.32 (s, 3H); 3.42 (td, J=6.8-Hz, J=5.8-Hz, 2H); 3.70 (s, 3H); 4.10 (q, J=7-Hz, 2H); 4.40 (t, J=5.8-Hz, 1H); 6.70 (d, J=6.7-Hz, 2H); 6.99 (d, J=6.7-Hz, 2H); 7.18 (m, 1H); 7.44-7.56 (m, 2H); 7.60 (d, J=6.8-Hz, 2H); 7.88 (m, 1H); 7.90 (d, J=6.8-Hz, 2H); 10.70 (s, 1H).

EXAMPLE 46

Synthesis of (Z)-2-ethoxy-3-[3'-(1-methyl-3-phenylureido)biphenyl-4-yl]acrylic acid

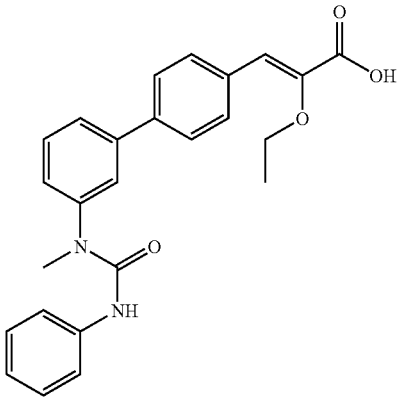 [SMILES: CCO/C(=C\c1ccc(-c2cccc(N(C)C(=O)Nc3ccccc3)c2)cc1)C(=O)O]

a-Ethyl (Z)-2-ethoxy-3-[3'-(1-methyl-3-phenylureido)biphenyl-4-yl]acrylate

A mixture of 1 g (3 mmol) of ethyl (Z)-2-ethoxy-3-(3'-methylaminobiphenyl-4-yl)acrylate (prepared according to Example 41b) and 0.7 mL (6 mmol) of phenyl isocyanate is placed in a sealed tube and heated at 50° C. for 15 hours. The reaction medium is cooled and the residue obtained is purified by chromatography on a column of silica eluted with a 7/3 heptane/ethyl acetate mixture. 1.3 g (96%) of ethyl (Z)-2-ethoxy-3-[3'-(1-methyl-3-phenylureido)biphenyl-4-yl]acrylate are obtained in the form of a colorless oil.

b-(Z)-2-ethoxy-3-[3'-(1-methyl-3-phenylureido)biphenyl-4-yl]acrylic acid

In a manner similar to that of Example 41e, starting with 1.3 g (2.9 mmol) of ethyl (Z)-2-ethoxy-3-[3'-(1-methyl-3-phenylureido)biphenyl-4-yl]acrylate, 0.5 g (41%) of (Z)-2-ethoxy-3-[3'-(1-methyl-3-phenylureido)biphenyl-4-yl] acrylic acid is obtained in the form of a pale yellow solid.
$^1$H NMR (CDCl$_3$, 400 MHz): 1.39 (t, J=7-Hz, 3H); 3.40 (s, 3H); 4.10 (q, J=7-Hz, 2H); 6.39 (s, 1H); 7.00 (m, 1H); 7.10 (s, 1H); 7.22-7.25 (m, 2H); 7.30-7.33 (m, 3H); 7.54 (d, J=8.3-Hz, 2H); 7.55-7.64 (m, 3H); 7.89 (d, J=8.4-Hz, 2H).

EXAMPLE 47

Synthesis of (Z)-2-ethoxy-3-[3'-(1-methyl-3-p-tolylureido)biphenyl-4-yl]acrylic acid

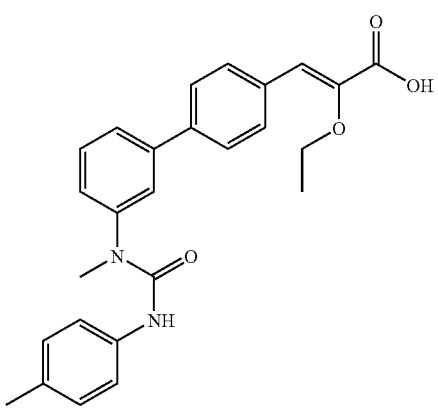 [SMILES: CCO/C(=C\c1ccc(-c2cccc(N(C)C(=O)Nc3ccc(C)cc3)c2)cc1)C(=O)O]

a-Ethyl (Z)-2-ethoxy-3-[3'-(1-methyl-3-p-tolylureido)biphenyl-4-yl]acrylate

A mixture of 1 g (3 mmol) of ethyl (Z)-2-ethoxy-3-(3'-methylaminobiphenyl-4-yl)acrylate (prepared according to Example 41b) and 0.8 mL (6 mmol) of 4-methylphenyl isocyanate is placed in a sealed tube and heated at 50° C. for 15 hours. The reaction medium is cooled and the residue obtained is purified by chromatography on a column of silica eluted with a 7/3 heptane/ethyl acetate mixture. 1.2 g (85%) of ethyl (Z)-2-ethoxy-3-[3'-(1-methyl-3-p-tolylureido)biphenyl-4-yl]acrylate are obtained in the form of a white paste.

b-(Z)-2-ethoxy-3-[3'-(1-methyl-3-p-tolylureido)biphenyl-4-yl]acrylic acid

In a manner similar to that of Example 41e, starting with 1.2 g (2.6 mmol) of ethyl (Z)-2-ethoxy-3-[3'-(1-methyl-3-p-tolylureido)biphenyl-4-yl]acrylate, 0.4 g (36%) of (Z)-2-ethoxy-3-[3'-(1-methyl-3-p-tolylureido)biphenyl-4-yl] acrylic acid is obtained in the form of a pale yellow solid with a melting point of 92° C.
$^1$H NMR (CDCl$_3$, 400 MHz): 1.42 (t, J=7-Hz, 3H); 2.27 (s, 3H); 3.40 (s, 3H); 4.13 (q, J=7-Hz, 2H); 6.27 (s, 1H); 7.05 (d, J=8.3-Hz, 2H); 7.18-7.20 (m, 3H); 7.35 (m, 1H); 7.55 (t, J=7.8-Hz, 1H); 7.64 (d, J=8.4-Hz, 2H); 7.62 (m, 2H); 7.90 (d, J=8.4-Hz, 2H).

EXAMPLE 48

Synthesis of (Z)-2-ethoxy-3-{3'-[1-methyl-3-(4-trifluoromethylphenyl)ureido]biphenyl-4-yl}acrylic acid

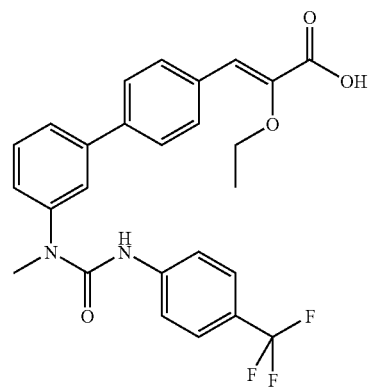 [SMILES: CCO/C(=C\c1ccc(-c2cccc(N(C)C(=O)Nc3ccc(C(F)(F)F)cc3)c2)cc1)C(=O)O]

a-Ethyl (Z)-2-ethoxy-3-{3'-[1-methyl-3-(4-trifluoromethylphenyl)ureido]biphenyl-4-yl}acrylate A mixture of 1 g (3 mmol) of ethyl (Z)-2-ethoxy-3-(3'-methylaminobiphenyl-4-yl)acrylate (prepared according to Example 43b) and 0.8 mL (6 mmol) of 4-trifluoromethylphenyl isocyanate is placed in a sealed tube and heated at 50° C. for 15 hours. The reaction medium is cooled and the residue obtained is purified by chromatography on a column of silica eluted with a 7/3 heptane/ethyl acetate mixture. 1.5 g (95%) of ethyl (Z)-2-ethoxy-3-{3'-[1-methyl-3-(4-trifluoromethylphenyl)ureido]biphenyl-4-yl}acrylate are obtained in the form of a white foam.

b-(Z)-2-ethoxy-3-{3'-[1-methyl-3-(4-trifluoromethylphenyl)ureido]biphenyl-4-yl}acrylic acid In a manner similar to that of Example 43e, starting with 1.5 g (3 mmol) of ethyl (Z)-2-ethoxy-3-{3'-[1-methyl-3-(4-trifluoromethylphenyl)ureido]biphenyl-4-yl}acrylate, g (%) of (Z)-2-ethoxy-3-{3'-[1-methyl-3-(4-trifluoromethylphenyl)ureido]biphenyl-4-yl}acrylic acid are obtained in the form of a tacky paste.

$^1$H NMR (CDCl$_3$, 400 MHz)—: 1.44 (t, J=7.1-Hz, 2H); 3.41 (s, 3H); 4.09 (q, J=7.1-Hz, 2H); 6.47 (s, 1H); 7.20 (s, 1H); 7.44 (d, J=8.7-Hz, 2H); 7.48 (d, J=8.7-Hz, 2H); 7.60-7.70 (m, 3H); 7.64 (d, J=8.5-Hz, 2H); 7.92 (d, J=8.5-Hz, 2H); 10.70 (s, 1H).

EXAMPLE 49

Synthesis of (Z)-3-[3'-(3-heptyl-1-methylureido)biphenyl-4-yl]-2-methoxyacrylic acid

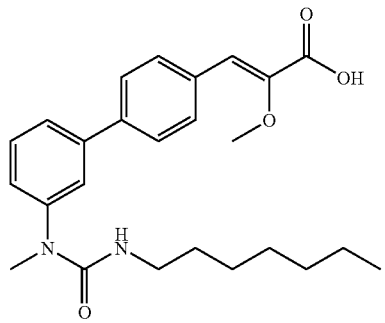 [SMILES: CCCCCCCNC(=O)N(C)c1cccc(-c2ccc(/C=C(\OC)C(=O)O)cc2)c1]

a-Methyl (Z)-3-[3'-(3-heptyl-1-methylureido)biphenyl-4-yl]-2-methoxyacrylate 0.6 mL (3.9 mmol) of heptylamine is added to a solution of 1.7 g (3.2 mmol) of methyl (Z)-2-methoxy-3-{3'-[methyl-(4-nitrophenoxycarbonyl)amino]biphenyl-4-yl}acrylate (prepared according to Example 11e) in 10 mL of dimethylformamide and the reaction medium is then placed in a bath preheated to 80° C. After stirring at 80° C. for 3 hours, water is added and the reaction medium is extracted with ethyl acetate. The organic phase is washed with saturated aqueous sodium chloride solution, filtered and evaporated. The residue obtained is purified by chromatography on a column of silica eluted with a 7/3 and then 6/4 heptane/ethyl acetate mixture. 1.1 g (80%) of methyl (Z)-3-[3'-(3-heptyl-1-methylureido)biphenyl-4-yl]-2-methoxyacrylate are obtained in the form of a white solid with a melting point of 93° C.

b-(Z)-3-[3'-(3-heptyl-1-methylureido)biphenyl-4-yl]-2-methoxyacrylic acid 3.3 mL (3.3 mmol) of aqueous 1 N sodium hydroxide solution are added to a solution of 1 g (2.2 mmol) of methyl (Z)-3-[3'-(3-heptyl-1-methylureido)biphenyl-4-yl]-2-methoxyacrylate in 16 mL of tetrahydrofuran. The reaction medium is heated at 68° C. and stirred for 4 hours. The reaction medium is acidified with 3.5 mL of 1 N acetic acid solution and extracted with ethyl acetate. The organic phase is washed with water, dried over magnesium sulfate, filtered and evaporated. The residue obtained is recrystallized from a hot heptane/ethyl acetate mixture. 800 mg (86%) of (Z)-3-[3'-(3-heptyl-1-methylureido)biphenyl-4-yl]-2-methoxyacrylic acid are obtained in the form of a white solid with a melting point of 114° C.

$^1$H NMR (CDCl$_3$, 400 MHz): 0.85 (t, J=7.5-Hz, 3H); 1.26 (m, 8H); 1.42 (m, 2H); 3.18 (td, J=5.5-Hz, J=7.6-Hz, 2H); 3.33 (s, 3H); 3.87 (s, 3H); 4.40 (t, J=5.5-Hz, 1H); 7.17 (s, 1H); 7.24 (m, 1H); 7.51-7.58 (m, 3H); 7.60 (d, J=8.4-Hz, 2H); 7.87 (d, J=8.4-Hz, 2H); 10.70 (s, 1H).

EXAMPLE 50

Synthesis of 2-[1-[3'-(3-heptyl-1-methylureido)biphenyl-4-yl]meth-(E)-ylidene]pentanoic acid

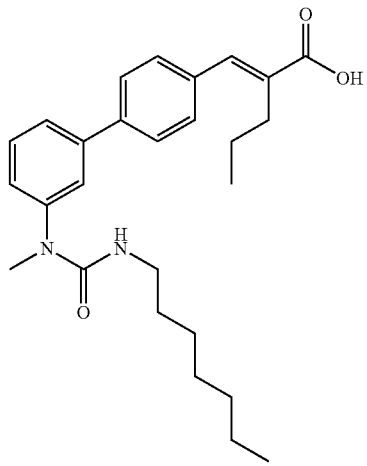 [SMILES: CCCCCCCNC(=O)N(C)c1cccc(-c2ccc(/C=C(\CCC)C(=O)O)cc2)c1]

a-Ethyl 2-[1-[3'-(3-heptyl-1-methylureido)biphenyl-4-yl]meth-(E)-ylidene]pentanoate 172 µL (1 mmol) of heptyl isocyanate are added to 251 mg (0.8 mmol) of ethyl 2-[1-(3'-methylaminobiphenyl-4-yl)meth-(E)-ylidene]pentanoate (prepared according to Example 8a). The reaction mixture is heated at 100° C. in an Emrys Optimizer microwave oven for 20 minutes. The residue is purified by chromatography on a column of silica eluted with a 70/30 heptane/ethyl acetate mixture. 361 mg (100%) of ethyl 2-[1-[3'-(3-heptyl-1-methylureido)biphenyl-4-yl]meth-(E)-ylidene]pentanoate are obtained in the form of a yellowish oil.

b-2-[1-[3'-(3-heptyl-1-methylureido)biphenyl-4-yl]meth-(E)-ylidene]pentanoic acid 351 mg (7.5 mmol, 10 eq) of sodium hydroxide are added to a solution of 302 mg (0.75 mmol, 1-eq) of ethyl 2-[1-[3'-(3-heptyl-1-methylureido)biphenyl-4-yl]meth-(E)-ylidene]pentanoate in 15 mL of ethanol. The reaction mixture is heated at 50° C. for 15 hours. The reaction medium is evaporated to dryness, taken up in water, acidified with 2N hydrochloric acid solution and extracted with ethyl acetate. The organic phases are combined, washed with water and dried over magnesium sulfate. The solvent is evaporated off and the solid obtained is purified by chromatography on a column of silica eluted with a 50/50 heptane/ethyl acetate mixture. The solvents are evaporated off and the solid obtained is crystallized from a mixture of ethyl ether and heptane, filtered off and dried.

258 mg (79%) of 2-[1-[3'-(3-heptyl-1-methylureido)biphenyl-4-yl]meth-(E)-ylidene]pentanoic acid are obtained in the form of a white powder with a melting point of 79-81° C.

$^1$H NMR (CDCl$_3$, 400 MHz): 0.84 (t, 3H); 1.02 (t, 3H); 1.22 (m, 8H); 1.42 (m, 2H); 1.63-1.69 (m, 2H); 2.55-2.59 (m, 2H); 3.18 (q, 2H); 3.32 (s, 3H); 4.39 (t, 1H); 7.24 (d, 1H); 7.50 (m, 4H); 7.56 (t, 1H); 7.63 (d, 2H); 7.82 (s, 1H).

EXAMPLE 51

Synthesis of (Z)-3-[2-butoxy-3'-(3-heptylureido) biphenyl-4-yl]-2-methoxyacrylic acid

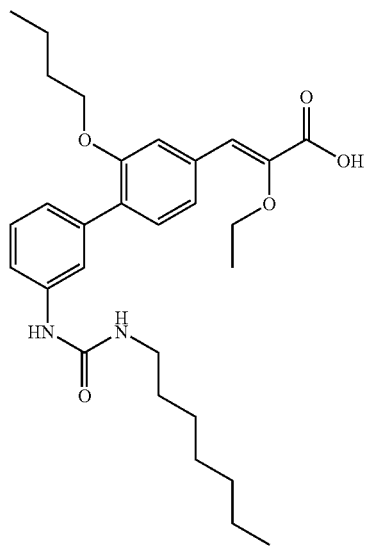 [SMILES: CCCCCCCNC(=O)Nc1cccc(-c2ccc(/C=C(\OCC)C(=O)O)cc2OCCCC)c1]

a-Methyl (Z)-3-(3'-amino-2-butoxybiphenyl-4-yl)-2-methoxyacrylate 11.2 mL (22.4 mmol) of aqueous 2 N potassium carbonate solution and 0.52 g (0.45 mmol) of tetrakis(triphenylphosphine)palladium are added to a solution of 1.87 g (10.8 mmol) of 3-aminophenylboronic acid hydrochloride and 3.5 g (9 mmol) of methyl (Z)-3-(3-butoxy-4-iodophenyl)-2-methoxyacrylate (prepared according to Example 24c) in 70 mL of ethylene glycol dimethyl ether. The reaction mixture is heated at 100° C. for 4 hours. After addition of 30 mL of water and extraction with ethyl acetate, the organic phases are combined, washed with saturated sodium chloride solution and dried over sodium sulfate. The solvents are evaporated off and the residue is then purified by chromatography on a column of silica eluted with a 90/10 heptane/ethyl acetate mixture. 3 g (93%) of methyl (Z)-3-(3'-amino-2-butoxybiphenyl-4-yl)-2-methoxyacrylate are obtained in the form of a yellow oil.

b-Methyl (Z)-3-[2-butoxy-3'-(3-heptylureido)biphenyl-4-yl]-2-methoxyacrylate 376 mg (1.1 mmol) of methyl (Z)-3-(3'-amino-2-butoxybiphenyl-4-yl)-2-methoxyacrylate and 0.3 mL (2.2 mmol) of heptyl isocyanate are heated at 100° C. by microwave in an Emrys Optimizer machine for 20 minutes. The residue obtained is taken up in ether and then filtered by suction. 431 mg (79%) of methyl (Z)-3-[2-butoxy-3'-(3-heptylureido)biphenyl-4-yl]-2-methoxyacrylate are obtained in the form of a white powder.

c-(Z)-3-[2-butoxy-3'-(3-heptylureido)biphenyl-4-yl]-2-methoxyacrylic acid 1.3 mL (1.3 mmol) of aqueous 1 N lithium hydroxide solution are added to a solution of 423 mg (0.87 mmol) of methyl (Z)-3-[2-butoxy-3'-(3-heptylureido)biphenyl-4-yl]-2-methoxyacrylate in 10 mL of tetrahydrofuran. The reaction mixture is stirred for 24 hours at room temperature. After addition of 20 mL of water and acidification with 1 N hydrochloric acid, the reaction medium is extracted with ethyl acetate. The organic phases are combined, washed with saturated sodium chloride solution and dried over sodium sulfate. The solvents are evaporated off and the residue is then recrystallized from 5 mL of acetonitrile. 348 mg (85%) of (Z)-3-[2-butoxy-3'-(3-heptylureido)biphenyl-4-yl]-2-methoxyacrylic acid are obtained in the form of a white powder. (m.p.=137° C.).

$^1$H NMR (DMSO-d$_6$, 400 MHz): 0.87 (t, 3H); 0.89 (t, 3H); 1.27-1.35 (m, 8H); 1.37-1.42 (m, 4H); 1.65 (m, 2H); 3.08 (td, J=6.7-Hz, J=5.5-Hz, 2H); 3.76 (s, 3H); 4.00 (t, J=6.4-Hz, 2H); 6.12 (t, J=5.5-Hz, 1H); 6.96 (s, 1H); 7.05 (d, J=7.7-Hz, 1H); 7.22-7.33 (m, 3H); 7.43 (d, J=7.7-Hz, 1H); 7.51 (s, 1H); 7.58 (s, 1H); 8.39 (s, 1H); 13 (s, 1H).

EXAMPLE 52

Cross-Curve PPAR Transactivation Tests

The activation of the receptors with an agonist (activator) in HeLN cells leads to the expression of a reporter gene, luciferase, which, in the presence of a substrate, generates light. The modulation of the receptors is measured by quantifying the luminescence produced after incubating the cells in the presence of a reference agonist. The ligands displace the agonist from its site. The measurement of the activity is performed by quantifying the light produced. This measurement makes it possible to determine the modulatory activity of the compounds according to the invention by determining the constant that is the affinity of the molecule for the receptor. Since this value can fluctuate depending on the basal activity and the expression of the receptor, it is referred to as Kd apparent (KdApp in nM).

To determine this constant, "cross curves" of the test product against a reference agonist are produced in a 96-well plate: 10 concentrations of the test product plus a concentration 0 are arranged in a line, and 7 concentrations of the agonist plus a concentration 0 are arranged in a column. This is 88 measurement points for 1 product and 1 receptor. The remaining 8 wells are used for repeatability controls.

In each well, the cells are in contact with a concentration of the test product and a concentration of the reference agonist, 2-(4-{2-[3-(2,4-difluorophenyl)-1-heptylureido] ethyl}phenylsulfanyl)-2-methylpropionic acid for PPARα, {2-methyl-4-[4-methyl-2-(4-trifluoromethylphenyl)thiazol-5-ylmethylsulfanyl]phenoxy}acetic acid for PPARδ and 5-{4-[2-(methylpyrid-2-ylamino)ethoxy] benzyl}thiazolidine-2,4-dione for PPARδ. Measurements are also taken for total agonist controls with the same products.

The HeLN cell lines used are stable transfectants containing the plasmids ERE-βGlob-Luc-SV-Neo (reporter gene) and PPAR (α, δ, γ) Gal-hPPAR. These cells are inoculated into 96-well plates at a rate of 10-000 cells per well in 100 µL of DMEM medium without phenol red and supplemented with 10% of defatted calf serum. The plates are then incubated at 37° C. and 7% $CO_2$ for 16 hours. The various dilutions of the test products and of the reference ligand are added at a rate of 5 μL per well. The plates are then incubated for 18 hours at 37° C. and 7% $CO_2$.

The culture medium is removed by turning over and 100 μL of a 1:1 PBS/luciferin mixture are added to each well. After 5 minutes, the plates are read by the luminescence detector.

These cross curves make it possible to determine the AC50 values (concentration at which 50% activation is observed) of the reference ligand at various concentrations of test product. These AC50 values are used to calculate the Schild regression by plotting a straight line corresponding to the Schild equation ("*quantitation in receptor pharmacology*" Terry P. Kenakin, *Receptors and Channels*, 2001, 7, 371-385), which allows the Kd app values (in nM) to be obtained.

Transactivation Results:

| Compounds | PPAR alpha Kd app (nM) | PPARs delta Kd app (in nM) | PPAR gamma Kd app (in nM) |
|---|---|---|---|
| Reference 1: 2-(4-{2-[3-(2,4-Difluorophenyl)-1-heptylureido]-ethyl}phenylsulfanyl)-2-methylpropionic acid | 200 | n.a. | n.a |
| Reference 2: {2-Methyl-4-[4-methyl-2-(4-trifluoromethylphenylthiazol-5-ylmethysulfanyl]phenoxy}acetic acid | n.a. | 10 | n.a |
| Reference 3: 5-{4-[2-(Methylpyrid-2-ylamino)ethoxy]benzyl}-thiazolidine-2,4-dione | n.a | n.a | 30 |
| Compound 1 | 2000 | n.a | 30 |
| Compound 2 | 1000 | n.a | 30 |
| Compound 3 | n.a | n.a | 30 |
| Compound 4 | n.a | n.a | 4 |
| Compound 5 | n.a | n.a | 2 |
| Compound 6 | n.a | n.a | 60 |
| Compound 7 | n.a | n.a | 4 |
| Compound 8 | 500 | 2000 | 4 |
| Compound 9 | 2000 | 2000 | 4 |
| Compound 10 | n.a | n.a | 4 |
| Compound 11 | n.a | n.a | 4 |
| Compound 12 | n.a | n.a | 15 |
| Compound 13 | n.a | 4000 | 8 |
| Compound 14 | n.a | 4000 | 60- |
| Compound 15 | n.a | n.a | 8 |
| Compound 16 | n.a | n.a | 8 |
| Compound 21 | n.a | n.a | 30 |
| Compound 22 | n.a | n.a | 120 |
| Compound 31 | n.a | n.a | 2 |
| Compound 32 | 4000 | n.a | 1 | n.a means not active

These results show the affinity of the compounds for the PPAR receptors and more particularly for the PPARγ subtype.

EXAMPLE 53

Compositions

Various specific formulations based on the compounds according to the invention are illustrated below.

A—Oral Route:
(a) 0.2 g Tablet:

| | |
|---|---|
| Compound 3 | 0.001 g |
| Starch | 0.114 g |
| Dicalcium phosphate | 0.020 g |
| Silica | 0.020 g |
| Lactose | 0.030 g |
| Talc | 0.010 g |
| magnesium stearate | 0.005 g |

(b) Drinkable Suspension in 5 mL Ampules:

| | |
|---|---|
| Compound 9 | 0.001 g |
| glycerol | 0.500 g |
| 70% sorbitol | 0.500 g |
| Sodium saccharinate | 0.010 g |
| methyl parahydroxybenzoate | 0.040 g |
| Flavoring | qs |
| Purified water | qs 5 ml |

B—Topical Route:
(a) Ointment:

| | |
|---|---|
| Compound 2 | 0.300 g |
| White petroleum jelly codex | qs 100 g |

(d) Lotion:

| | |
|---|---|
| Compound 5 | 0.100 g |
| Polyethylene glycol (PEG 400) | 69.900 g |
| 95% ethanol | 30.000 g |

(e) Hydrophobic Ointment:

| | |
|---|---|
| Compound 10 | 0.300 g |
| Isopropyl myristate | 36.400 g |
| Silicone oil ("Rhodorsil 47 V 300" marketed by Rhône-Poulenc) | 36.400 g |
| Beeswax | 13.600 g |
| Silicone oil ("Abil 300.000 cSt" marketed by Goldschmidt) | qs 100 g |

(f) Nonionic Oil-in-Water Cream:

| | |
|---|---|
| Compound 7 | 1.000 g |
| Cetyl alcohol | 4.000 g |
| Glyceryl monostearate | 2.500 g |
| PEG 50 stearate | 2.500 g |
| Shea butter | 9.200 g |
| Propylene glycol | 2.000 g |
| Methyl parahydroxybenzoate | 0.075 g |

-continued

| Propyl parahydroxybenzoate | 0.075 g |
| Sterile demineralized water | qs 100 g |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A biaromatic compound having the formula (I):

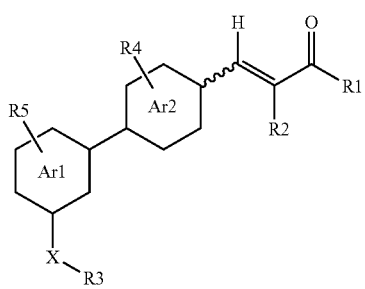

(I)

in which:
R1 is a radical —OR6, a radical —NR6OR6, or a radical NR6R6, wherein R6 is as defined below;
R2 is a halogen atom, an alkyl radical having from 1 to 12 carbon atoms, a radical —OR7, a radical —NHR7, or an aralkyl radical, wherein R7 is as defined below;
R3 is an alkyl radical having from 1 to 12 carbon atoms, a cycloalkyl radical having from 3 to 12 carbon atoms, or a sequence —(CH$_2$)$_m$R8, wherein m and R8 are as defined below;
X is the following sequence:

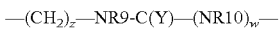
—(CH$_2$)$_z$—NR9-C(Y)—(NR10)$_w$— wherein w, z, R9, R10 and Y are as defined below,
m is an integer ranging from 0 to 4;
Y is an oxygen or sulfur atom;
z and w are each 0 or 1;
Ar1 and Ar2 are each an aromatic radical optionally substituted with a radical R4 or R5 as defined below and having the formula:
for Ar1:

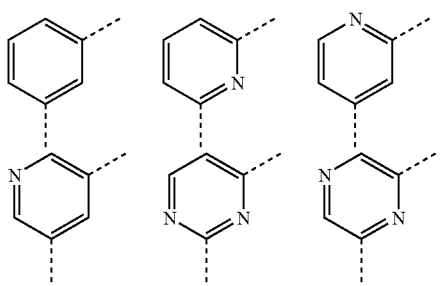

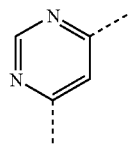

for Ar2:

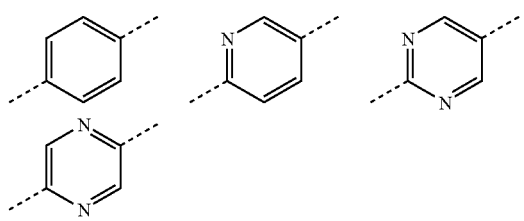

wherein the groups Ar2 and XR3 are in a meta arrangement on the aromatic radical Ar1 and the groups Ar1 and CH=CR2-COR1 are in para arrangement on the aromatic radical Ar2;
R4 and R5, which are identical or different, are each a hydrogen atom, a halogen atom, an alkyl radical having from 1 to 12 carbon atoms, a hydroxyl radical, an alkoxy radical, a polyether radical, an aralkyl radical, an aryl radical, or an amino radical that is optionally substituted with one or two radicals, which are identical or different, selected from an alkyl radical having from 1 to 12 carbon atoms and an aralkyl radical;
R6 is a hydrogen atom, an alkyl radical having from 1 to 7 carbon atoms, an aryl radical or an aralkyl radical;
R7 is a hydrogen atom, an alkyl radical having from 1 to 7 carbon atoms, an aryl radical or an aralkyl radical;
R8 is an alkyl radical having from 1 to 7 carbon atoms, a cycloalkyl radical, an aryl radical, an aralkyl radical, a heteroaryl radical, a heterocycloalkyl radical, a radical —OR11, or a substituted or unsubstituted amine function;
R9 and R10, which are identical or different, are each a hydrogen atom or an alkyl radical having from 1 to 4 carbon atoms;
R11 is a hydrogen atom, an alkyl radical having from 1 to 7 carbon atoms, an aryl radical or an aralkyl radical;
or a pharmaceutically acceptable salt thereof;
wherein the wavy line indicates that the compound has the (E) or (Z) configuration.

2. The biaromatic compound as defined by claim 1, wherein R1 is a radical —OR6.

3. The biaromatic compound as defined by claim 1, wherein R2 is an alkyl radical having from 1 to 7 carbon atoms or a radical —OR7.

4. The biaromatic compound as defined by claim 1, wherein R3 is an alkyl radical having from 1 to 12 carbon atoms or a sequence
—(CH$_2$)$_m$R8, in which m=0, 1 or 2 and R8 is an aryl radical, a cycloalkyl radical or a heteroaryl radical.

5. The biaromatic compound as defined by claim 1, wherein R4 and R5 are each a hydrogen atom, an alkoxy radical having from 1 to 7 carbon atoms or a polyether radical.

6. The biaromatic compound as defined by claim 1, wherein X is a sequence —NR9-C(Y)—NR10- or a sequence —CH$_2$—NR9-C(Y)—.

7. The biaromatic compound as defined by claim 1, wherein R9 is a hydrogen atom or an alkyl radical having from 1 to 4 carbon atoms.

8. The biaromatic compound as defined by claim 1, wherein:
R1 is a radical —OR6, in which R6 is a hydrogen atom;
R2 is an alkyl radical having from 1 to 4 carbon atoms, a radical —OR7, in which R7 is an alkyl radical having from 1 to 4 carbon atoms;
R3 is an alkyl radical having from 3 to 8 carbon atoms, a cyclohexyl radical or a sequence —$(CH_2)_m$—R8, in which R8 is a phenyl radical optionally substituted with a methyl radical, a methoxy radical or a trifluoromethyl radical;
m is equal to 0, 1 or 2;
X is a sequence —NR9-C(Y)—NR10- or a sequence —$CH_2$—NR9C(Y)—, in which R9 is a hydrogen atom, a methyl radical, R10 is a hydrogen atom and Y is an oxygen atom;
R4 is a hydrogen atom, an alkoxy radical having from 1 to 7 carbon atoms, or a polyether radical;
R5 is a hydrogen atom; and
Ar1 and Ar2 are each a phenyl radical or a pyridyl radical or a pharmaceutically acceptable salt thereof.

9. The biaromatic compound as defined by claim 1, or a pharmaceutically acceptable salt thereof, selected from the group consisting of the following compounds:
(Z)-2-Ethoxy-3-{3'-[(methyloctanoylamino)methyl]biphenyl-4-yl}acrylic acid;
(Z)-2-Ethoxy-3-{4-[6-(3-heptyl-1-methylureido)pyrid-2-yl]phenyl}acrylic acid;
(Z)-2-Ethoxy-3-{4-[6-(1-methyl-3-pentylureido)pyrid-2-yl]phenyl}acrylic acid;
(Z)-2-Ethoxy-3-{6-[3-(3-heptyl-1-methylureido)phenyl]pyrid-3-yl}acrylic acid hydrochloride;
(E)-3-[3'-(3-Heptyl-1-methylureido)biphenyl-4-yl]-2-methylacrylic acid;
(Z)-2-Fluoro-3-[3'-(3-heptyl-1-methylureido)biphenyl-4-yl]acrylic acid;
2-[1-[3'-(3-Heptyl-1-methylureido)biphenyl-4-yl]meth-(E)-ylidene]butyric acid;
2-[1-[3'-(1-Methyl-3-pentylureido)biphenyl-4-yl]meth-(E)-ylidene]pentanoic acid;
2-[1-[3'-(1-Methyl-3-pentylureido)biphenyl-4-yl]meth-(E)-ylidene]butyric acid;
(Z)-2-Ethoxy-3-[3'-(1-methyl-3-phenethylureido)biphenyl-4-yl]acrylic acid;
(Z)-3-[3'-(3-Butyl-1-methylureido)biphenyl-4-yl]-2-methoxyacrylic acid;
Methyl (Z)-3-[3'-(3-butyl-1-methylureido)biphenyl-4-yl]-2-methoxyacrylate;
(Z)-2-Methoxy-3-[3'-(1-methyl-3-pentylureido)biphenyl-4-yl]acrylic acid;
Methyl (Z)-3-[3'-(3-cyclohexyl-1-methylureido)biphenyl-4-yl]-2-methoxyacrylate;
(Z)-3-[3'-(3-Cyclohexyl-1-methylureido)biphenyl-4-yl]-2-methoxyacrylic acid;
(Z)-2-Methoxy-3-[3'-(1-methyl-3-phenethylureido)biphenyl-4-yl]acrylic acid;
Methyl (Z)-2-methoxy-3-[3'-(1-methyl-3-phenylureido)biphenyl-4-yl]acrylate;
(Z)-2-Methoxy-3-[3'-(1-methyl-3-phenylureido)biphenyl-4-yl]acrylic acid;
(E)-3-{3'-[(Benzoylmethylamino)methyl]-2-butoxybiphenyl-4-yl}-2-methylacrylic acid;
(E)-3-(2-Butoxy-3'-{[(4-methoxybenzoyl)methylamino]methyl}biphenyl-4-yl)-2-methylacrylic acid;
(E)-3-(2-Butoxy-3'-{[(3-methoxybenzoyl)methylamino]methyl}biphenyl-4-yl)-2-methylacrylic acid;
2-[1-{3'-[(Benzoylmethylamino)methyl]-2-butoxybiphenyl-4-yl}meth-(E)-ylidene]butyric acid;
(Z)-3-[2-Butoxy-3'-(1-methyl-3-phenethylureido)biphenyl-4-yl]-2-ethoxyacrylic acid;
(Z)-3-[2-Butoxy-3'-(1-methyl-3-pentylureido)biphenyl-4-yl]-2-methoxyacrylic acid;
(Z)-3-[2-Butoxy-3'-(3-heptyl-1-methylureido)biphenyl-4-yl]-2-methoxyacrylic acid;
(Z)-3-[2-Butoxy-3'-(1-methyl-3-pentylureido)biphenyl-4-yl]-2-ethoxyacrylic acid;
(Z)-3-[2-Butoxy-3'-(3-heptyl-1-methylureido)biphenyl-4-yl]-2-ethoxyacrylic acid;
(Z)-3-[2-Butoxy-3'-(3-butyl-1-methylureido)biphenyl-4-yl]-2-methoxyacrylic acid;
(Z)-3-[2-Butoxy-3'-(3-butyl-1-methylureido)biphenyl-4-yl]-2-ethoxyacrylic acid;
(Z)-3-[2-Butoxy-3'-(3-cyclohexyl-1-methylureido)biphenyl-4-yl]-2-ethoxyacrylic acid;
(E)-3-[3'-(3-Heptyl-1-methylureido)-2-propoxybiphenyl-4-yl]-2-methylacrylic acid;
(E)-3-[2-Ethoxy-3'-(3-heptyl-1-methylureido)biphenyl-4-yl]-2-methylacrylic acid;
2-[1-[2-Ethoxy-3'-(3-heptyl-1-methylureido)biphenyl-4-yl]meth-(E)-ylidene]butyric acid;
(E)-3-[2-Butoxy-3'-(1-methyl-3-pentylureido)biphenyl-4-yl]-2-methylacrylic acid;
(E)-3-[2-Butoxy-3'-(3-heptyl-1-methylureido)biphenyl-4-yl]-2-methylacrylic acid;
2-[1-[2-Butoxy-3'-(1-methyl-3-pentylureido)biphenyl-4-yl]meth-(E)-ylidene]butyric acid;
2-[1-[2-Butoxy-3'-(3-heptyl-1-methylureido)biphenyl-4-yl]meth-(E)-ylidene]butyric acid;
(Z)-2-Ethoxy-3-[2-(2-ethoxyethoxy)-3'-(1-methyl-3-pentylureido)biphenyl-4-yl]acrylic acid;
(Z)-3-[2-(2-Ethoxyethoxy)-3'-(1-methyl-3-pentylureido)biphenyl-4-yl]-2-methoxyacrylic acid;
(E)-3-[2-Butoxy-3'-(3-heptyl-1-methylureido)biphenyl-4-yl]-2-methoxyacrylic acid;
L-Arginine salt of (Z)-2-ethoxy-3-[3'-(3-heptyl-1-methylureido)biphenyl-4-yl]acrylic acid;
L-Arginine salt of (Z)-2-ethoxy-3-[3'-(1-methyl-3-pentylureido)biphenyl-4-yl]acrylic acid;
(Z)-3-[3'-(3-Butyl-1-methylureido)biphenyl-4-yl]-2-ethoxyacrylic acid;
(Z)-3-[3'-(3-Cyclohexyl-1-methylureido)biphenyl-4-yl]-2-ethoxyacrylic acid;
(Z)-2-Ethoxy-3-(3'-{3-[2-(4-methoxyphenyl)ethyl]-1-methylureido}biphenyl-4-yl)acrylic acid;
(Z)-2-Ethoxy-3-[3'-(1-methyl-3-phenylureido)biphenyl-4-yl]acrylic acid;
(Z)-2-Ethoxy-3-[3'-(1-methyl-3-p-tolylureido)biphenyl-4-yl]acrylic acid;
(Z)-2-Ethoxy-3-{3'-[1-methyl-3-(4-trifluoromethylphenyl)ureido]biphenyl-4-yl}acrylic acid;
(Z)-3-[3'-(3-Heptyl-1-methylureido)biphenyl-4-yl]-2-methoxyacrylic acid;
2-[1-[3'-(3-Heptyl-1-methylureido)biphenyl-4-yl]meth-(E)-ylidene]pentanoic acid;
(Z)-3-[2-Butoxy-3'-(3-heptylureido)biphenyl-4-yl]-2-methoxyacrylic acid;
(Z)-2-Ethoxy-3-[3'-(3-hexyl-1-methylureido)biphenyl-4-yl]acrylic acid;
(Z)-3-{3'-[3-(4-Butylphenyl)-1-methylureido]biphenyl-4-yl}-2-ethoxyacrylic acid;

(Z)-2-Ethoxy-3-{3'-[3-(4-ethylphenyl)-1-methylureido]biphenyl-4-yl}acrylic acid;
(Z)-2-Ethoxy-3-{3'-[3-(4-ethoxyphenyl)-1-methylureido]biphenyl-4-yl}acrylic acid;
(Z)-3-{3'-[3-(4-Butoxyphenyl)-1-methylureido]biphenyl-4-yl}-2-ethoxyacrylic acid;
(E)-2-Methyl-3-[3'-(1-methyl-3-pentylureido)biphenyl-4-yl]acrylic acid;
(E)-3-[3'-(3-Heptyl-1-methylthioureido)biphenyl-4-yl]-2-methylacrylic acid;
(Z)-2-Ethoxy-3-{3'-[1-methyl-3-(3-phenylpropyl)ureido]biphenyl-4-yl}acrylic acid;
(Z)-2-Ethoxy-3-(3'-{[(3-1H-indol-3-ylpropionyl)methylamino]methyl}biphenyl-4-yl)acrylic acid;
(Z)-2-Benzyloxy-3-[3'-(3-heptyl-1-methylureido)biphenyl-4-yl]acrylic acid;
Methyl (Z)-2-ethoxy-3-[3'-(3-heptyl-1-methylureido)biphenyl-4-yl]acrylate;
Benzyl (Z)-2-ethoxy-3-[3'-(3-heptyl-1-methylureido)biphenyl-4-yl]acrylate;
Phenyl (Z)-2-ethoxy-3-[3'-(3-heptyl-1-methylureido)biphenyl-4-yl]acrylate;
(Z)-3-[3'-(3-Heptyl-1-methylureido)biphenyl-4-yl]-2-propoxyacrylic acid;
(Z)-2-Ethoxy-3-[3'-(1-methyl-3-naphthalen-2-ylureido)biphenyl-4-yl]acrylic acid;
(Z)-3-{3'-[3-(4-Dimethylaminophenyl)-1-methylureido]biphenyl-4-yl}-2-ethoxyacrylic acid;
(Z)-3-[3'-(3-Benzo[1.2.5]thiadiazol-5-yl-1-methylureido)biphenyl-4-yl]-2-ethoxyacrylic acid;
(Z)-2-Ethoxy-3-(3'-{[methyl-(1-methylpiperidine-3-carbonyl)amino]methyl}biphenyl-4-yl) acrylic acid;
(Z)-2-Ethoxy-3-[3'-(3-heptyl-1-methylureido)biphenyl-4-yl]acrylic acid;
(Z)-2-Ethoxy-3-[3'-(1-methyl-3-pentylureido)biphenyl-4-yl]acrylic acid;
(Z)-3-[3'-(3-Hexyl-1-methylureido)biphenyl-4-yl]-2-methoxyacrylic acid;
(E)-3-{3'-[(Benzoylmethylamino)methyl]biphenyl-4-yl}-2-methylacrylic acid;
Ethyl (Z)-2-ethoxy-3-{3'-[(methyloctanoylamino)methyl]biphenyl-4-yl}acrylate;
Ethyl (Z)-2-ethoxy-3-[3'-(3-heptyl-1-methylureido)biphenyl-4-yl]acrylate;
Ethyl (Z)-2-ethoxy-3-[3'-(1-methyl-3-pentylureido)biphenyl-4-yl]acrylate;
Ethyl (E)-3-[3'-(3-heptyl-1-methylureido)biphenyl-4-yl]-2-methylacrylate;
(Z)-2-Ethoxy-3-(3'-{3-[2-(4-methoxyphenyl)ethyl]-1-methylureido}biphenyl-4-yl)acrylic acid;
(Z)-2-Ethoxy-3-{3'-[1-methyl-3-(4-trifluoromethylphenyl)ureido]biphenyl-4-yl}acrylic acid;
(Z)-2-Ethoxy-3-[3-fluoro-3'-(3-hexyl-1-methylureido)biphenyl-4-yl]acrylic acid;
(Z)-2-Methoxy-3-[3-fluoro-3'-(3-pentyl-1-methylureido)biphenyl-4-yl]acrylic acid;
(Z)-2-Ethoxy-3-[2-fluoro-3'-(3-hexyl-1-methylureido)biphenyl-4-yl]acrylic acid;
(Z)-2-Methoxy-3-[2-fluoro-3'-(3-pentyl-1-methylureido)biphenyl-4-yl]acrylic acid;
(Z)-2-Ethoxy-3-[2'-methyl-5'-(1-methyl-3-pentylureido)biphenyl-4-yl]acrylic acid;
(Z)-2-Methoxy-3-[2'-methyl-5'-(1-methyl-3-pentylureido)biphenyl-4-yl]acrylic acid;
(Z)-2-Ethoxy-3-[2-methyl-3'-(3-pentyl-1-methylureido)biphenyl-4-yl]acrylic acid;
(Z)-2-Methoxy-3-[2-methyl-3-'-(3-pentyl-1-methylureido)biphenyl-4-yl]acrylic acid;
(Z)-2-Ethoxy-3-(3'-{[(4-methoxybenzoyl)methylamino]methyl}-2-methylbiphenyl-4-yl)acrylic acid;
(Z)-2-Methoxy-3-(3'-{[(4-methoxybenzoyl)methylamino]methyl}-2-methylbiphenyl-4-yl)acrylic acid;
(Z)-2-Ethoxy-3-(2-methoxy-3'-{[methyl-(4-trifluoromethylbenzoyl)amino]methyl}biphenyl-4-yl) acrylic acid;
(Z)-2-Methoxy-3-(2-methoxy-3'-{[methyl-(4-trifluoromethylbenzoyl)amino]methyl}biphenyl-4-yl) acrylic acid;
(Z)-3-(4-{6-[3-(4-Butoxyphenyl)-1-methylureido]pyrid-2-yl}phenyl)-2-ethoxyacrylic acid;
(E)-2-Methyl-3-{4-[6-(1-methyl-3-pentylureido)pyrid-2-yl]phenyl}acrylic acid;
(E)-3-{4-[6-(3-Heptyl-1-methylureido)pyrid-2-yl]phenyl}-2-methylacrylic acid;
2-[1-{6-[3-(3-Heptyl-1-methylureido)phenyl]pyrid-3-yl}meth-(E)-ylidene]pentanoic acid;
(Z)-2-Fluoro-3-{4-[4-(3-heptyl-1-methylureido)pyrid-2-yl]phenyl}acrylic acid;
(Z)-2-Ethoxy-3-{4-[4-(3-heptyl-1-methylureido)pyrimidin-2-yl]phenyl}acrylic acid;
(Z)-2-Methoxy-3-{4-[6-(1-methyl-3-pentylureido)pyrid-2-yl]phenyl}acrylic acid;
(E)-2-{4-[6-(1-Methyl-3-pentylureido)pyrid-2-yl]benzylidene}butyric acid;
(Z)-2-Ethoxy-3-{6-[3-(1-methyl-3-pentylureido)phenyl]pyrid-3-yl}acrylic acid;
Ethyl (Z)-2-ethoxy-3-{4-[6-(3-heptyl-1-methylureido)pyrid-2-yl]phenyl}acrylate;
Ethyl (Z)-2-ethoxy-3-{4-[6-(1-methyl-3-pentylureido)pyrid-2-yl]phenyl}acrylate;
Ethyl (Z)-2-ethoxy-3-{6-[3-(3-heptyl-1-methylureido)phenyl]pyrid-3-yl}acrylate;
(E)-2-Methyl-3-{5-[3-(1-methyl-3-pentylureido)phenyl]pyrazin-2-yl}acrylic acid;
(Z)-2-Ethoxy-3-{4-[2-(3-heptyl-1-methylureido)pyrimidin-4-yl]phenyl}acrylic acid;
(Z)-2-Ethoxy-3-{6-[3-(3-heptyl-1-methylureido)phenyl]pyrid-3-yl}-N-hydroxyacrylamide;
(Z)-2-Ethoxy-3-{6-[3-(3-heptyl-1-methylureido)phenyl]pyrid-3-yl}-N-methoxyacrylamide;
(Z)-3-{6-[3-(3-Butyl-1-methylureido)phenyl]pyrid-3-yl}-2-methoxyacrylic acid;
(Z)-3-{6-[3-(3-Heptyl-1-methylureido)phenyl]pyrid-3-yl}-2-methoxyacrylic acid;
(Z)-2-Methoxy-3-{6-[3-(1-methyl-3-pentylureido)phenyl]pyrid-3-yl}acrylic acid;
(Z)-2-Ethoxy-3-[3'-(3-heptyl-1-methylureido)biphenyl-4-yl]-N-hydroxyacrylamide;
(Z)-2-Ethoxy-3-[3'-(3-heptyl-1-methylureido)biphenyl-4-yl]-N-methoxyacrylamide;
(Z)-3-[3'-(3-Butyl-1-methylureidomethyl)biphenyl-4-yl]-2-ethoxyacrylic acid;
(Z)-2-Ethoxy-3-(4-{6-[3-(4-methoxyphenyl)-1-ethylureido]pyrid-2-yl}phenyl)acrylic acid; and
(Z)-2-Ethylamino-3-{3'-[1-methyl-3-(3-phenylpropyl)ureido]biphenyl-4-yl}acrylic acid.

10. A pharmaceutical composition comprising at least one biaromatic compound as defined by claim 1, formulated into at least one pharmaceutically acceptable excipient.

11. The pharmaceutical composition as defined by claim 10, wherein the concentration of said biaromatic compound ranges from 0.001% to 10% by weight relative to the total weight of the composition.

12. The pharmaceutical composition as defined by claim 11, wherein the concentration of said biaromatic compound ranges from 0.01% to 1% by weight relative to the total weight of the composition.

13. A cosmetic composition comprising at least one biaromatic compound as defined by claim 1, formulated into a physiologically acceptable support therefor.

14. The cosmetic composition as defined by claim 13, wherein the concentration of said biaromatic compound ranges from 0.001% to 3% by weight relative to the total weight of the composition.

15. A method for regulating and/or restoring skin lipid metabolism, said method comprising administering to a subject in need of such treatment, a thus effective amount of at least one biaromatic compound as defined by claim 1.

16. A process for preparing a biaromatic compound of formula (I) as defined by claim 1, from a compound of formula 8 below:

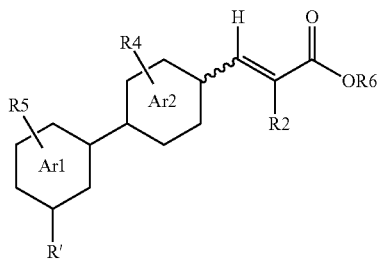

in which R2, R4, R5, R6, Ar1 and Ar2 are as defined in claim 1 and R' is —NO₂, —NR9G or —CH2—NR9G wherein G is an amine-protecting group or a hydrogen atom, comprising, first reducing the nitro group of 8 to an amino group or after deprotecting the amine of 8, and then performing the following steps:
a) adding the resultant compound to an isocyanate or to a thioisocyanate, or alternatively reacting the resultant compound with nitrophenyl chloroformate followed by reacting with an amine when R' is —NHR9;
or adding the resultant compound to a carboxylic acid halide or to a thiocarboxylic acid halide when R' is —CH2-NHR9;
b) optionally, saponifying the compound obtained in a) in the presence of sodium hydroxide; and
c) optionally, reacting the compound obtained in b) with oxalyl chloride, followed by reacting with hydroxylamine or the O-substituted hydroxylamine.

17. A biaromatic compound having the formula (I):

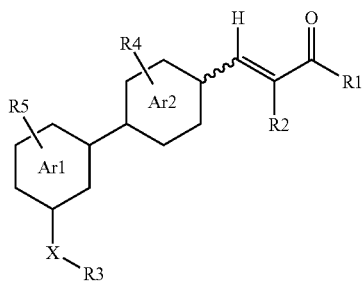

in which:
R1 is a radical —OR6, a radical —NR6OR6, or a radical NR6R6, wherein R6 is as defined below;
R2 is a halogen atom, a radical —OR7, a radical —NHR7, or an aralkyl radical, wherein R7 is as defined below;
R3 is an alkyl radical having from 1 to 12 carbon atoms, a cycloalkyl radical having from 3 to 12 carbon atoms, or a sequence —(CH₂)ₘR8, wherein m and R8 are as defined below;
X is the following sequence:

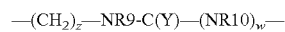

wherein w, z, R9, R10 and Y are as defined below,
m is an integer ranging from 0 to 4;
Y is an oxygen or sulfur atom;
z and w are each 0 or 1;
Ar1 and Ar2 are each an aromatic radical optionally substituted with a radical R4 or R5 as defined below and having the formula:
for Ar1:

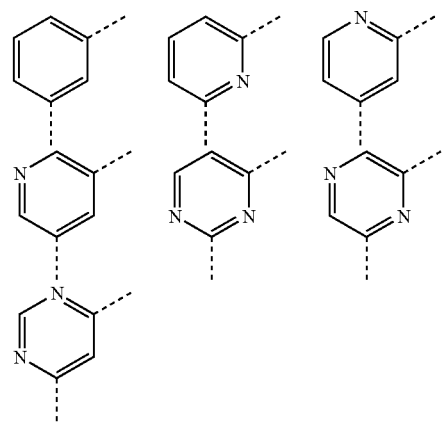

for Ar2:

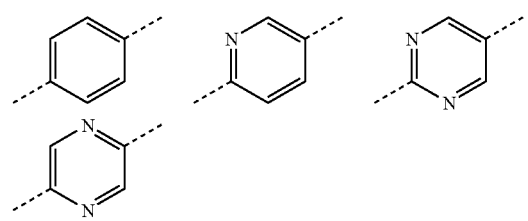

wherein the groups Ar2 and XR3 are in a meta arrangement on the aromatic radical Ar1 and the groups Ar1 and CH=CR2-COR1 are in para arrangement on the aromatic radical Ar2;
R4 and R5, which are identical or different, are each a hydrogen atom, a halogen atom, an alkyl radical having from 1 to 12 carbon atoms, a hydroxyl radical, an alkoxy radical, a polyether radical, an aralkyl radical, an aryl radical or an amino radical that is optionally substituted with one or two radicals, which are identical or different, selected from an alkyl radical having from 1 to 12 carbon atoms and an aralkyl radical;
R6 is a hydrogen atom, an alkyl radical having from 1 to 7 carbon atoms, an aryl radical or an aralkyl radical;
R7 is a hydrogen atom, an alkyl radical having from 1 to 7 carbon atoms, an aryl radical or an aralkyl radical;

R8 is an alkyl radical having from 1 to 7 carbon atoms, a cycloalkyl radical, an aryl radical, an aralkyl radical, a heteroaryl radical, a heterocycloalkyl radical, a radical —OR11, or a substituted or unsubstituted amine function;

R9 and R10, which are identical or different, are each a hydrogen atom or an alkyl radical having from 1 to 4 carbon atoms;

R11 is a hydrogen atom, an alkyl radical having from 1 to 7 carbon atoms, an aryl radical or an aralkyl radical;

or a pharmaceutically acceptable salt thereof;

wherein the wavy line indicates that the compound has the (E) or (Z) configuration.

18. The biaromatic compound as defined by claim 17, wherein R1 is a radical —OR6.

19. The biaromatic compound as defined by claim 17, wherein R2 is a radical —OR7.

20. The biaromatic compound as defined by claim 17, wherein R3 is an alkyl radical having from 1 to 12 carbon atoms or a sequence —$(CH_2)_m$R8, in which m=0, 1 or 2 and R8 is an aryl radical, a cycloalkyl radical or a heteroaryl radical.

21. The biaromatic compound as defined by claim 17, wherein R4 and R5 are each a hydrogen atom, an alkoxy radical having from 1 to 7 carbon atoms or a polyether radical.

22. The biaromatic compound as defined by claim 17, wherein X is a sequence —NR9-C(Y)—NR10- or a sequence —$CH_2$—NR9-C(Y)—.

23. The biaromatic compound as defined by claim 17, wherein R9 is a hydrogen atom or an alkyl radical having from 1 to 4 carbon atoms.

24. The biaromatic compound as defined by claim 17, wherein:
R1 is a radical —OR6, in which R6 is a hydrogen atom;
R2 is a radical —OR7, in which R7 is an alkyl radical having from 1 to 4 carbon atoms;
R3 is an alkyl radical having from 3 to 8 carbon atoms, a cyclohexyl radical or a sequence —$(CH_2)_m$—R8, in which R8 is a phenyl radical optionally substituted with a methyl radical, a methoxy radical or a trifluoromethyl radical;
m is equal to 0, 1 or 2;
X is a sequence —NR9-C(Y)—NR10- or a sequence —$CH_2$—NR9C(Y)—, in which R9 is a hydrogen atom or a methyl radical, R10 is a hydrogen atom and Y is an oxygen atom;
R4 is a hydrogen atom, an alkoxy radical having from 1 to 7 carbon atoms, or a polyether radical;
R5 is a hydrogen atom; and
Ar1 and Ar2 are each a phenyl radical or a pyridyl radical
or a pharmaceutically acceptable salt thereof;
wherein the wavy line indicates that the compound has the (E) or (Z) configuration.

25. The biaromatic compound or a pharmaceutically acceptable salt thereof, selected from the group consisting of the following compounds:
(Z)-2-Ethoxy-3-{3'-[(methyloctanoylamino)methyl]biphenyl-4-yl}acrylic acid;
(Z)-2-Ethoxy-3-{4-[6-(3-heptyl-1-methylureido)pyrid-2-yl]phenyl}acrylic acid;
(Z)-2-Ethoxy-3-{4-[6-(1-methyl-3-pentylureido)pyrid-2-yl]phenyl}acrylic acid;
(Z)-2-Ethoxy-3-{6-[3-(3-heptyl-1-methylureido)phenyl]pyrid-3-yl}acrylic acid hydrochloride;
(Z)-2-Fluoro-3-[3'-(3-heptyl-1-methylureido)biphenyl-4-yl]acrylic acid;
2-[1-[3'-(3-Heptyl-1-methylureido)biphenyl-4-yl]meth-(E)-ylidene]butyric acid;
2-[1-[3'-(1-Methyl-3-pentylureido)biphenyl-4-yl]meth-(E)-ylidene]pentanoic acid;
2-[1-[3'-(1-Methyl-3-pentylureido)biphenyl-4-yl]meth-(E)-ylidene]butyric acid;
(Z)-2-Ethoxy-3-[3'-(1-methyl-3-phenethylureido)biphenyl-4-yl]acrylic acid;
(Z)-3-[3'-(3-Butyl-1-methylureido)biphenyl-4-yl]-2-methoxyacrylic acid;
Methyl (Z)-3-[3'-(3-butyl-1-methylureido)biphenyl-4-yl]-2-methoxyacrylate;
(Z)-2-Methoxy-3-[3'-(1-methyl-3-pentylureido)biphenyl-4-yl]acrylic acid;
Methyl (Z)-3-[3'-(3-cyclohexyl-1-methylureido)biphenyl-4-yl]-2-nnethoxyacrylate;
(Z)-3-[3'-(3-Cyclohexyl-1-methylureido)biphenyl-4-yl]-2-methoxyacrylic acid;
(Z)-2-Methoxy-3-[3'-(1-methyl-3-phenethylureido)biphenyl-4-yl]acrylic acid;
Methyl (Z)-2-methoxy-3-[3'-(1-methyl-3-phenylureido)biphenyl-4-yl]acrylate;
(Z)-2-Methoxy-3-[3'-(1-methyl-3-phenylureido)biphenyl-4-yl]acrylic acid;
2-[1-{3'-[(Benzoylmethylamino)methyl]-2-butoxybiphenyl-4-yl}meth-(E)-ylidene]butyric acid;
(Z)-3-[2-Butoxy-3'-(1-methyl-3-phenethylureido)biphenyl-4-yl]-2-ethoxyacrylic acid;
(Z)-3-[2-Butoxy-3'-(1-methyl-3-pentylureido)biphenyl-4-yl]-2-methoxyacrylic acid;
(Z)-3-[2-Butoxy-3'-(3-heptyl-1-methylureido)biphenyl-4-yl]-2-methoxyacrylic acid;
(Z)-3-[2-Butoxy-3'-(1-methyl-3-pentylureido)biphenyl-4-yl]-2-ethoxyacrylic acid;
(Z)-3-[2-Butoxy-3'-(3-heptyl-1-methylureido)biphenyl-4-yl]-2-ethoxyacrylic acid;
(Z)-3-[2-Butoxy-3'-(3-butyl-1-nnethylureido)biphenyl-4-yl]-2-methoxyacrylic acid;
(Z)-3-[2-Butoxy-3'-(3-butyl-1-methylureido)biphenyl-4-yl]-2-ethoxyacrylic acid;
(Z)-3-[2-Butoxy-3'-(3-cyclohexyl-1-methylureido)biphenyl-4-yl]-2-ethoxyacrylic acid;
2-[1-[2-Ethoxy-3'-(3-heptyl-1-methylureido)biphenyl-4-yl]meth-(E)-ylidene]butyric acid;
2-[1-[2-Butoxy-3'-(1-methyl-3-pentylureido)biphenyl-4-yl]meth-(E)-ylidene]butyric acid;
2-[1-[2-Butoxy-3'-(3-heptyl-1-methylureido)biphenyl-4-yl]meth-(E)-ylidene]butyric acid;
(Z)-2-Ethoxy-3-[2-(2-ethoxyethoxy)-3'-(1-methyl-3-pentylureido)biphenyl-4-yl]acrylic acid;
(Z)-3-[2-(2-Ethoxyethoxy)-3'-(1-methyl-3-pentylureido)biphenyl-4-yl]-2-methoxyacrylic acid;
(E)-3-[2-Butoxy-3'-(3-heptyl-1-methylureido)biphenyl-4-yl]-2-methoxyacrylic acid;
L-Arginine salt of (Z)-2-ethoxy-3-[3'-(3-heptyl-1-methylureido)biphenyl-4-yl]acrylic acid;
L-Arginine salt of (Z)-2-ethoxy-3-[3'-(1-methyl-3-pentylureido)biphenyl-4-yl]acrylic acid;
(Z)-3-[3'-(3-Butyl-1-methylureido)biphenyl-4-yl]-2-ethoxyacrylic acid;
(Z)-3-[3'-(3-Cyclohexyl-1-methylureido)biphenyl-4-yl]-2-ethoxyacrylic acid;
(Z)-2-Ethoxy-3-(3'-{3-[2-(4-methoxyphenyl)ethyl]-1-methylureido}biphenyl-4-yl)acrylic acid;
(Z)-2-Ethoxy-3-[3'-(1-methyl-3-phenylureido)biphenyl-4-yl]acrylic acid;
(Z)-2-Ethoxy-3-[3'-(1-methyl-3-p-tolylureido)biphenyl-4-yl]acrylic acid;
(Z)-2-Ethoxy-3-{3'-[1-methyl-3-(4-trifluoromethylphenyl)ureido]biphenyl-4-yl}acrylic acid;
(Z)-3-[3'-(3-Heptyl-1-methylureido)biphenyl-4-yl]-2-methoxyacrylic acid;
2-[1-[3'-(3-Heptyl-1-methylureido)biphenyl-4-yl]meth-(E)-ylidene]pentanoic acid;

(Z)-3-[2-Butoxy-3'-(3-heptylureido)biphenyl-4-yl]-2-methoxyacrylic acid;
(Z)-2-Ethoxy-3-[3'-(3-hexyl-1-methylureido)biphenyl-4-yl]acrylic acid;
(Z)-3-{3'-[3-(4-Butylphenyl)-1-methylureido]biphenyl-4-yl}-2-ethoxyacrylic acid;
(Z)-2-Ethoxy-3-{3'-[3-(4-ethylphenyl)-1-methylureido]biphenyl-4-yl}acrylic acid;
(Z)-2-Ethoxy-3-{3'-[3-(4-ethoxyphenyl)-1-methylureido]biphenyl-4-yl}acrylic acid;
(Z)-3-{3'-[3-(4-Butoxyphenyl)-1-methylureido]biphenyl-4-yl}-2-ethoxyacrylic acid;
(E)-2-Methyl-3-[3'-(1-methyl-3-pentylureido)biphenyl-4-yl]acrylic acid;
(Z)-2-Ethoxy-3-{3'-[1-methyl-3-(3-phenylpropyl)ureido]biphenyl-4-yl}acrylic acid;
(Z)-2-Ethoxy-3-(3'-{[(3-1H-indol-3-ylpropionyl)methylamino]methyl}biphenyl-4-yl)acrylic acid;
(Z)-2-Benzyloxy-3-[3'-(3-heptyl-1-methylureido)biphenyl-4-yl]acrylic acid;
Methyl (Z)-2-ethoxy-3-[3'-(3-heptyl-1-methylureido)biphenyl-4-yl]acrylate;
Benzyl (Z)-2-ethoxy-3-[3'-(3-heptyl-1-methylureido)biphenyl-4-yl]acrylate;
Phenyl (Z)-2-ethoxy-3-[3'-(3-heptyl-1-methylureido)biphenyl-4-yl]acrylate;
(Z)-3-[3'-(3-Heptyl-1-methylureido)biphenyl-4-yl]-2-propoxyacrylic acid;
(Z)-2-Ethoxy-3-[3'-(1-methyl-3-naphthalen-2-ylureido)biphenyl-4-yl]acrylic acid;
(Z)-3-{3'-[3-(4-Dimethylaminophenyl)-1-methylureido]biphenyl-4-yl}-2-ethoxyacrylic acid;
(Z)-3-[3'-(3-Benzo[1.2.5]thiadiazol-5-yl-1-methylureido)biphenyl-4-yl]-2-ethoxyacrylic acid;
(Z)-2-Ethoxy-3-(3'-{[methyl-(1-methylpiperidine-3-carbonyl)amino]methyl}biphenyl-4-yl)acrylic acid;
(Z)-2-Ethoxy-3-[3'-(3-heptyl-1-methylureido)biphenyl-4-yl]acrylic acid;
(Z)-2-Ethoxy-3-[3'-(1-methyl-3-pentylureido)biphenyl-4-yl]acrylic acid;
(Z)-3-[3'-(3-Hexyl-1-methylureido)biphenyl-4-yl]-2-methoxyacrylic acid;
Ethyl (Z)-2-ethoxy-3-{3'-[(methyloctanoylamino)methyl]biphenyl-4-yl}acrylate;
Ethyl (Z)-2-ethoxy-3-[3'-(3-heptyl-1-methylureido)biphenyl-4-yl]acrylate;
Ethyl (Z)-2-ethoxy-3-[3'-(1-methyl-3-pentylureido)biphenyl-4-yl]acrylate;
(Z)-2-Ethoxy-3-(3'-{3-[2-(4-methoxyphenyl)ethyl]-1-methylureido}biphenyl-4-yl)acrylic acid;
(Z)-2-Ethoxy-3-{3'-[1-methyl-3-(4-trifluoromethylphenyl)ureido]biphenyl-4-yl}acrylic acid;
(Z)-2-Ethoxy-3-[3-fluoro-3'-(3-hexyl-1-methylureido)biphenyl-4-yl]acrylic acid;
(Z)-2-Methoxy-3-[3-fluoro-3'-(3-pentyl-1-methylureido)biphenyl-4-yl]acrylic acid;
(Z)-2-Ethoxy-3-[2-fluoro-3'-(3-hexyl-1-methylureido)biphenyl-4-yl]acrylic acid;
(Z)-2-Methoxy-3-[2-fluoro-3'-(3-pentyl-1-methylureido)biphenyl-4-yl]acrylic acid;
(Z)-2-Ethoxy-3-[2'-methyl-5'-(1-methyl-3-pentylureido)biphenyl-4-yl]acrylic acid;
(Z)-2-Methoxy-3-[2'-methyl-5'-(1-methyl-3-pentylureido)biphenyl-4-yl]acrylic acid;
(Z)-2-Ethoxy-3-[2-methyl-3'-(3-pentyl-1-methylureido)biphenyl-4-yl]acrylic acid;
(Z)-2-Methoxy-3-[2-methyl-3'-(3-pentyl-1-methylureido)biphenyl-4-yl]acrylic acid;
(Z)-2-Ethoxy-3-(3'-{[(4-methoxybenzoyl)methylamino]methyl}-2-methylbiphenyl-4-yl)acrylic acid;
(Z)-2-Methoxy-3-(3'-{[(4-methoxybenzoyl)methylamino]methyl}-2-methylbiphenyl-4-yl)acrylic acid;
(Z)-2-Ethoxy-3-(2-methoxy-3'-{[methyl-(4-trifluoromethylbenzoyl)amino]methyl}biphenyl-4-yl)acrylic acid;
(Z)-2-Methoxy-3-(2-methoxy-3'-{[methyl-(4-trifluoromethylbenzoyl)amino]methyl}biphenyl-4-yl)acrylic acid;
(Z)-3-(4-{6-[3-(4-Butoxyphenyl)-1-methylureido]pyrid-2-yl}phenyl)-2-ethoxyacrylic acid;
2-[1-{6-[3-(3-Heptyl-1-methylureido)phenyl]pyrid-3-yl}meth-(E)-ylidene]pentanoic acid;
(Z)-2-Fluoro-3-{4-[4-(3-heptyl-1-methylureido)pyrid-2-yl]phenyl}acrylic acid;
(Z)-2-Ethoxy-3-{4-[4-(3-heptyl-1-methylureido)pyrimidin-2-yl]phenyl}acrylic acid;
(Z)-2-Methoxy-3-{4-[6-(1-methyl-3-pentylureido)pyrid-2-yl]phenyl}acrylic acid;
(E)-2-{4-[6-(1-Methyl-3-pentylureido)pyrid-2-yl]benzylidene}butyric acid;
(Z)-2-Ethoxy-3-{6-[3-(1-methyl-3-pentylureido)phenyl]pyrid-3-yl}acrylic acid;
Ethyl (Z)-2-ethoxy-3-{4-[6-(3-heptyl-1-methylureido)pyrid-2-yl]phenyl}acrylate;
Ethyl (Z)-2-ethoxy-3-{4-[6-(1-methyl-3-pentylureido)pyrid-2-yl]phenyl}acrylate;
Ethyl (Z)-2-ethoxy-3-{6-[3-(3-heptyl-1-methylureido)phenyl]pyrid-3-yl}acrylate;
(E)-2-Methyl-3-{5-[3-(1-methyl-3-pentylureido)phenyl]pyrazin-2-yl}acrylic acid;
(Z)-2-Ethoxy-3-{4-[2-(3-heptyl-1-methylureido)pyrimidin-4-yl]phenyl}acrylic acid;
(Z)-2-Ethoxy-3-{6-[3-(3-heptyl-1-methylureido)phenyl]pyrid-3-yl}-N-hydroxyacrylamide;
(Z)-2-Ethoxy-3-{6-[3-(3-heptyl-1-methylureido)phenyl]pyrid-3-yl}-N-methoxyacrylamide;
(Z)-3-{6-[3-(3-Butyl-1-methylureido)phenyl]pyrid-3-yl}-2-methoxyacrylic acid;
(Z)-3-{6-[3-(3-Heptyl-1-methylureido)phenyl]pyrid-3-yl}-2-methoxyacrylic acid;
(Z)-2-Methoxy-3-{6-[3-(1-methyl-3-pentylureido)phenyl]pyrid-3-yl}acrylic acid;
(Z)-2-Ethoxy-3-[3'-(3-heptyl-1-methylureido)biphenyl-4-yl]-N-hydroxyacrylamide;
(Z)-2-Ethoxy-3-[3'-(3-heptyl-1-methylureido)biphenyl-4-yl]-N-methoxyacrylamide;
(Z)-3-[3'-(3-Butyl-1-methylureidomethyl)biphenyl-4-yl]-2-ethoxyacrylic acid;
(Z)-2-Ethoxy-3-(4-{6-[3-(4-methoxyphenyl)-1-ethylureido]pyrid-2-yl}phenyl)acrylic acid; and
(Z)-2-Ethylamino-3-{3'-[1-methyl-3-(3-phenylpropyl)ureido]biphenyl-4-yl}acrylic acid.

26. A method for activating PPARγ receptors, said method comprising contacting said receptors with a PPARγ activating amount of a biaromatic compound or salt thereof as defined by claim 1.

27. A pharmaceutical composition comprising at least one biaromatic compound as defined by claim 17, formulated into at least one pharmaceutically acceptable excipient.

28. The pharmaceutical composition as defined by claim 27, wherein the concentration of said biaromatic compound ranges from 0.001% to 10% by weight relative to the total weight of the composition.

29. The pharmaceutical composition as defined by claim 28, wherein the concentration of said biaromatic compound ranges from 0.01% to 1% by weight relative to the total weight of the composition.

30. A cosmetic composition comprising at least one biaromatic compound as defined 17, formulated into a physiologically acceptable support therefor.

31. The cosmetic composition as defined by claim 30, wherein the concentration of said biaromatic compound ranges from 0.001% to 3% by weight relative to the total weight of the composition.

32. A method for regulating and/or restoring skin lipid metabolism, said method comprising administering to a subject in need of such treatment, a thus effective amount of at least one biaromatic compound as defined by claim 17.

33. A process for preparing a biaromatic compound of formula (I) as defined by claim 17, from a compound of formula 8 below:

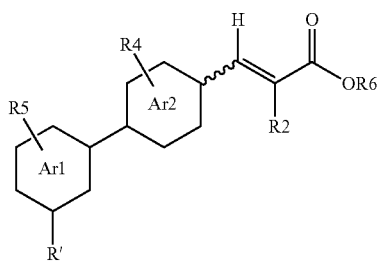

in which R2, R4, R5, R6, Ar1 and Ar2 are as defined in claim 1 and R' is —NO$_2$, —NR9G or —CH2—NR9G wherein G is an amine-protecting group or a hydrogen atom, comprising, first reducing the nitro group of 8 to an amino group or after deprotecting the amine of 8, and then performing the following steps:

a) adding the resultant compound to an isocyanate or to a thioisocyanate, or alternatively reacting the resultant compound with nitrophenyl chloroformate followed by reacting with an amine when R' is —NHR9;

or adding the resultant compound to a carboxylic acid halide or to a thiocarboxylic acid halide when R' is —CH2-NHR9;

b) optionally, saponifying the compound obtained in a) in the presence of sodium hydroxide; and c) optionally, reacting the compound obtained in b) with oxalyl chloride, followed by reacting with hydroxylamine or the O-substituted hydroxylamine.

34. A method for activating PPARγ receptors, said method comprising contacting said receptors with a PPARγ activating amount of a biaromatic compound or salt thereof as defined by claim 17.

* * * * *